(12) United States Patent
Bentsen et al.

(10) Patent No.: US 7,271,406 B2
(45) Date of Patent: Sep. 18, 2007

(54) ELECTRON TRANSPORT AGENTS FOR ORGANIC ELECTRONIC DEVICES

(75) Inventors: James G. Bentsen, North St. Paul, MN (US); Nicholas P. Goplen, North St. Paul, MN (US); Yingbo Li, Woodbury, MN (US); Ralph R. Roberts, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 175 days.

(21) Appl. No.: 10/413,653

(22) Filed: Apr. 15, 2003

(65) Prior Publication Data

US 2004/0214036 A1  Oct. 28, 2004

(51) Int. Cl.
*H01L 51/54* (2006.01)
*C07D 249/08* (2006.01)
*C07D 271/10* (2006.01)
*C07D 285/12* (2006.01)

(52) U.S. Cl. .................. 257/40; 313/504; 313/506; 428/690; 428/917; 548/136; 548/143; 548/145; 548/262.2; 548/269.4; 257/E51.047; 257/E51.049; 257/E51.05; 252/301.16

(58) Field of Classification Search ................ 428/690, 428/917; 313/504, 506; 257/40; 252/301.16; 548/136, 143, 145, 262.2, 269.4
See application file for complete search history.

(56) References Cited

U.S. PATENT DOCUMENTS

| | | | |
|---|---|---|---|
| 4,215,129 A | 7/1980 | Arrington et al. ........... 424/272 |
| 4,252,671 A | 2/1981 | Smith .......................... 252/430 |
| 5,061,569 A | 10/1991 | VanSlyke et al. ............. 428/457 |
| 5,166,024 A | 11/1992 | Bugner et al. ................. 430/70 |
| 5,256,506 A | 10/1993 | Ellis et al. ..................... 430/20 |
| 5,281,489 A * | 1/1994 | Mori et al. ................... 428/690 |
| 5,351,617 A | 10/1994 | Williams et al. ............. 101/467 |
| 5,408,109 A | 4/1995 | Heeger et al. ................. 257/40 |
| 5,508,136 A | 4/1996 | Shirota et al. ................. 430/73 |
| 5,536,588 A | 7/1996 | Naito .......................... 428/690 |
| 5,550,290 A | 8/1996 | Mizuta et al. ................. 564/309 |
| 5,621,131 A | 4/1997 | Kreuder et al. ............... 558/46 |
| 5,681,664 A | 10/1997 | Tamano et al. ............... 428/690 |
| 5,693,446 A | 12/1997 | Staral et al. .................. 430/201 |
| 5,695,907 A | 12/1997 | Chang ......................... 430/201 |
| 5,707,745 A | 1/1998 | Forrest et al. ................ 428/432 |
| 5,708,130 A | 1/1998 | Woo et al. ................... 528/397 |
| 5,710,097 A | 1/1998 | Staral et al. .................. 503/227 |
| 5,725,989 A | 3/1998 | Chang et al. ................. 430/201 |
| 5,728,801 A | 3/1998 | Wu et al. ..................... 528/422 |
| 5,792,557 A | 8/1998 | Nakaya et al. ............. 428/411.1 |
| 5,840,217 A | 11/1998 | Lupo et al. ................... 252/583 |
| 5,869,350 A | 2/1999 | Heeger et al. ................. 438/29 |
| 5,900,327 A | 5/1999 | Pei et al. ..................... 428/690 |
| 5,929,194 A | 7/1999 | Woo et al. ................... 528/229 |
| 5,945,502 A | 8/1999 | Hsieh et al. .................. 528/101 |
| 5,998,085 A | 12/1999 | Isberg et al. ................. 430/200 |
| 6,030,715 A | 2/2000 | Thompson et al. ......... 428/690 |
| 6,074,734 A | 6/2000 | Kawamura et al. ......... 428/220 |
| 6,114,088 A | 9/2000 | Wolk et al. ............... 430/273.1 |
| 6,132,641 A | 10/2000 | Rietz et al. ............. 252/301.16 |
| 6,150,043 A | 11/2000 | Thompson et al. ......... 428/690 |
| 6,169,163 B1 | 1/2001 | Woo et al. ................... 528/397 |
| 6,194,119 B1 | 2/2001 | Wolk et al. .................. 430/200 |
| 6,203,933 B1 | 3/2001 | Nakaya et al. .............. 428/690 |
| 6,214,520 B1 | 4/2001 | Wolk et al. ............... 430/273.1 |
| 6,221,543 B1 | 4/2001 | Guehler et al. ................ 430/7 |
| 6,221,553 B1 | 4/2001 | Wolk et al. .................. 430/200 |
| 6,228,543 B1 | 5/2001 | Mizuno et al. ................ 430/17 |
| 6,228,555 B1 | 5/2001 | Hoffend, Jr. et al. ....... 430/200 |
| 6,242,115 B1 | 6/2001 | Thomson et al. ........... 428/690 |
| 6,242,152 B1 | 6/2001 | Staral et al. ................. 430/201 |
| 6,284,425 B1 | 9/2001 | Staral et al. ................. 430/201 |
| 6,329,082 B1 | 12/2001 | Kreuder et al. ............. 428/690 |
| 6,358,664 B1 | 3/2002 | Nirmal et al. ............... 430/200 |
| 6,485,884 B2 | 11/2002 | Wolk et al. .................. 430/200 |
| 6,521,324 B1 | 2/2003 | Debe et al. .................. 428/195 |
| 6,664,111 B2 | 12/2003 | Bentsen et al. ................ 436/68 |
| 7,094,902 B2 * | 8/2006 | Roberts et al. .............. 548/128 |
| 2002/0158574 A1 | 10/2002 | Wolk et al. .................. 313/504 |
| 2003/0068525 A1 | 4/2003 | Bellmann et al. ........... 428/690 |
| 2003/0105343 A1* | 6/2003 | Taylor et al. ................ 549/462 |
| 2003/0124265 A1 | 7/2003 | Bellmann et al. ........... 427/536 |
| 2004/0062930 A1 | 4/2004 | Roberts et al. ............ 428/411.1 |

(Continued)

FOREIGN PATENT DOCUMENTS

| | | |
|---|---|---|
| DE | 3610649 | 10/1987 |
| EP | 0 553 950 A2 | 8/1993 |
| EP | 0650955 | 5/1995 |
| EP | 0827367 | 3/1998 |
| EP | 0879868 | 11/1998 |
| EP | 0891121 | 1/1999 |
| EP | 0953624 | 11/1999 |
| EP | 0968175 B | 1/2000 |
| EP | 1 013 740 A2 * | 6/2000 |
| EP | 1170273 | 1/2002 |
| GB | 2 348 316 | 9/2000 |

(Continued)

OTHER PUBLICATIONS

Machine assisted-translation for JP 2002-308855 A (Oct. 2002).*

(Continued)

*Primary Examiner*—Marie Yamnitzky
(74) *Attorney, Agent, or Firm*—Jean A. Lown

(57) ABSTRACT

Compounds and compositions are provided that can be used as electron transport agents in organic electronic devices such as organic electroluminescent devices. The compounds are non-polymeric and have an aromatic core conjugated to end capping groups. The aromatic core contains a phenylene group arylene or naphthalene group arylene having a pendant heteroaryl group that includes a —C═N— unit.

47 Claims, 2 Drawing Sheets

U.S. PATENT DOCUMENTS

| | | | |
|---|---|---|---|
| 2004/0106004 A1 | 6/2004 | Li | 428/690 |
| 2006/0051611 A1* | 3/2006 | Brunner et al. | 428/690 |

FOREIGN PATENT DOCUMENTS

| | | | |
|---|---|---|---|
| JP | 63-295695 | | 2/1988 |
| JP | 2-191694 | | 7/1990 |
| JP | 3-792 | | 1/1991 |
| JP | 5-152072 | | 6/1993 |
| JP | 5-202011 | | 8/1993 |
| JP | 6-096860 | | 4/1994 |
| JP | 10-195063 | | 7/1998 |
| JP | 2000-195673 | | 7/2000 |
| JP | 2001-97949 | | 4/2001 |
| JP | 2002-308855 | A * | 10/2002 |
| WO | WO98/06773 | | 2/1998 |
| WO | WO98/55561 | | 12/1998 |
| WO | WO99/32537 | | 7/1999 |
| WO | WO99/40655 | | 8/1999 |
| WO | WO 00/18851 | | 4/2000 |
| WO | WO 00/70655 | | 11/2000 |
| WO | WO 01/39234 | | 5/2001 |
| WO | WO 01/41512 | | 6/2001 |
| WO | WO 02/22374 | | 3/2002 |
| WO | WO 03/019179 | | 3/2003 |
| WO | WO 2004/055129 | | 7/2004 |

OTHER PUBLICATIONS

Amashukeli et al., *J. Phys. Chem. A.*, 106(33) 7593-7598 (2002), published on Web Apr. 10, 2002.
Bailey, T.R., *Tetrahedron Lett.*, 27, 4407-4410 (1986).
Barton et al., *Tetrahedron Lett.*, 24 (15) 1601-1604 (1983).
Bettenhausen et al., *Synthetic Metals*, 91, 223-228 (1997).
Bokova et al., *J. Org. Chem. USSR* (Engl. Transl.), 5, 1103-1106 (1969).
Brownstein, S.K., et al., *J. Org. Chem.*, 67, 663 (2002), published on Web Jan. 15, 2002.
Bumagin, N.A. et al., *J. Organomet. Chem.*, 364, 231-234 (1989).
Chen, C.H., et al., "Recent Developments in Molecular Organic Electroluminescent Materials," *Macromolecular Symposia*, 125, 1-48 (1997).
Clayden, J., et al., *J. Chem. Soc., Perkin Trans*, 1, 7 (1995).
Creason, S.C., et al., *J. Org. Chem.* 37, 4440-4446 (1972).
Fischer, *Chem Ber.*, 25, 2826-2846 (1892).
Friend, R.H., et al., "Electroluminescence in Conjugated Polymers", *Nature*, 121, 397 (Jan. 1999).
Fritsch, et al., *Chem Ber.*, 125, 849-855 (1992).
Fujikawa, et al., *Synthetic Metals*, 91, 161-162 (1997).
Gautun et al., *Acta Chem. Scand.*, 45(6), 609-615 (1991).
Goodbrand et al., *J. Org. Chem.* 64, 670-674 (1999), published on Web Dec. 31, 1998.
Grazulevicius, J.V. et al., "Charge-Transporting Polymers and Molecular Glasses", *Handbook of Advanced Electronic and Photonic Materials and Devices*, H. S. Nalwa (ed.), 10, 233-274 (2001).
Grekov et al., *J. Gen. Chem. USSR* (Engl. Transl) 30, 376303766 (1960).
Halls, J.J.M., et al., "Light-emitting and Photoconductive Diodes Fabricated with Conjugated Polymers," *Thin Solid Films*, 276, 13-20 (1996).
Huntress et al., *J. Am. Chem. Soc.*, 55, 4262-4270 (1933).
Ishiyama et al., *J. Org. Chem.*, 60, 7508-7510 (1995).
Kajino et al., *Chem. Pharm. Bull*, 39 (11), 2888-2895 (1991).
Kido, J., "Organic Electroluminescent Devices Based on Polymeric Materials," *Trends in Polymer Science*, 2, 350-355 (Oct. 1994).
Klingsberg, E, *J. Org. Chem.*, 23, 1086-1087 (1958).
Koene, B.E., et al., *Chem. Mater.*, 10, 2235-2250 (1998), published on Web Jul. 21, 1998.
Kraft, et al., *Angew. Chem. Int. Ed.*, 37, 402-428 (1998).
Kreger, K. et al., *Synthetic Metals*, 119, 163-164 (2001).
Kristensen et al., *Org. Lett.*, 10, 1435-1438 (2001), published on Web Apr. 25, 2001.
Meng, et al., *J. Am. Chem. Soc.*, 123(37), 9214-9215 (2001).
Miyaura, N., et al., *Chemical Reviews*, 95, 2457-2483 (1995).
Moss, et al., *J. Chem. Soc. Perkin Trans*, 1(9), 1999-2006 (1982).
Myznikov et al., *J. Gen. Chem. USSR* (Engl. Transl.), 62(6), 1125-1128 (1992).
Namkung et al., *J. Med. Chem. Soc.*, 8, 551-554 (Jul. 1965).
Otera, J., et al., *Bull. Chem. Soc. Jpn*, 54, 2964-2967 (1981).
Park, M., et al., *Tetrahedron*, 42, 12707-12714 (1998).
Pei, et al., *J. Org. Chem.*, 67, 4924-4936 (2002), published on Web Jun. 7, 2002.
Pei, Q., et al., "Polymer Light-Emitting Electrochemical Cells: In Situ Formation of Light-Emitting p-n Junction," *Journal of the American Chemical Society*, 118, 3922-3929 (1996).
Pilgram, K., et al., *J. Heterocycl. Chem*, 7, 629-633 (Jun. 1970).
Prudchenko, A.T., et al., *J. Gen. Chem. USSR* (Engl. Transl.), 37, 2082-2084 (1967).
Ranger, M., et al., *Can. J. Chem.*, 76, 1571-1577, 1998.
Ranger, M., et al., *Chem. Commun.*, 1597-1598 (1997).
Rule et al., *J. Chem. Soc.*, 1096-1101 (1937).
Salbeck et al., Low Molecular Organic Glasses for Blue Electroluminescence, *Synthetic Metals*, 91, 209-215 (1997).
Sanechika et al., *Bull. Chem. Soc. Jpn.*, 57, 752-755 (1984).
Schidlo et al., *Chem Ber.*, 96, 2595-2600 (1963).
Shen, Z., et al., "Three-Color, Tunable, Organic Light-Emitting Devices," *Science*, 276, 2009-2011 (Jun. 1997).
Strohriegl, P., "Charge Transporting Molecular Glasses," *Adv. Mat.*, 14, 1439 (Oct. 2002).
Strukelj et al., *Science*, 267, 1969-1972 (Mar. 1995).
Takahashi et al., *Synthesis*, 627-630 (Aug. 1980).
Hendrickson et al., J. Org. Chem., 52(18), 4137-4139 (1987).
Tamoto, et al., *Chem. Mater.*, 1077-1085 (1997).
Tanaka et al., *Chem. Commun.*, 2175-2176 (1996).
Tokito et al., *Appl. Phys. Lett.*, 70(15), 1929-1931 (Apr. 1997).
Tokito et al., *Polym. Prep.* (Am. Chem. Soc. Div. Polym. Chem.) 38(1), 388-389 (1997).
Tokito et al., *Synthetic Metals*, 111-112, 393-396 (2000).
Weber, E, et al., *J. Chem. Soc. Perkin Trans*, 2, 1251-1258 (1988).
Weil et al., *J. Amer. Chem. Soc.*, 123(33), 8101-8108 (2001), published on Web Aug. 15, 2001.
Widdowson, D.A., et al., *Tetrahedron*, 42, 2111-2116 (1986).
Yoon et al., *J. Chem. Soc., Chem. Commun.*, 13, 1013-1014 (1987).
Zinke, A., et al., *Chem. Ber.*, 74, 107-112 (1941).
Ayabe et al., "Construction of Monomeric and Polymeric Porphyrin Compartments by a Pd(II)-Pyridine Interaction and Their Chiral Twisting by a BINAP Ligand", *Journal of Organic Chemistry*, vol. 68, No. 3, pp. 1059-1066 (2003), published on Web Jan. 3, 2003.
Ikeda et al., "A Novel Self-Assembled Porphyrin Polymer Constructed by a Pd(II)-Pyridine Interaction", *Chemical Letters*, vol. 11, pp. 1138-1139 (2001).
Tomizaki et al., "Practical Synthesis of Perylene-Monoimide Building Blocks That Possess Features Appropriate For Use In Porphyrin-Based Light-Harvesting Arrays", *Tetrahedron*, vol. 59, No. 8, pp. 1191-1207 (2003).
Tomizaki et al., "Synthesis and Photophysical Properties of Light-Harvesting Arrays Comprised of a Porphyrin Bearing Multiple Perylene-Monoimide Accessory Pigments", *Journal of Organic Chemistry*, vol. 67, pp. 6519-6534 (2002), published on Web Aug. 14, 2002.
Cha et al., "Synthesis and Luminescence Properties of Four-Armed Conjugated Structures Containing 1,3,4-oxadiazole Moieties", *Journal of Materials Chemistry*, vol. 13, No. 8, pp. 1900-1904 (2003).
Nam et al., "Photoluminescence and Electroluminescence Properties of Poly(9-vinylcarbarzole) Doped With Anthracence Derivatives Containing bis(ethynylphenyl oxadiazole) or bis(vinylphenyl oxadiazole) Substituents", *Synthetic Metals*, vol. 130, No. 3, pp. 271-277 (2002).

Shi, Wei et al., "Synthesis And Insecticidal Activities of Novel 2-Fluorophenyl-5-arl/cyclopropyl-1,3,4-oxadiazoles," J. Fluorine Chem. (2000) vol. 106, pp. 173-179.

Detert et al., "Synthesis of Substituted 1,4-divinylbenznes by Heck Reactions With Compressed Ethene," Journal Fuer Praktische Chemie (1999), vol. 341(4), pp. 358-362, Abstract in CAPLUS, Accession No. 1999:337278.

Dutta et al., "Studies on Biologically active heterocycles. Part I . . . " J. Het. Chem, (1986), vol. 23(3), pp. 793-795, Abstract in CAPLUS, Accession No. 1987:138340.

Mazzone et al., "Some aroylhydrazones of halobenzaldehydes and halo-subst. 2,5-diaryl-1,3,4-oxadiazoles." Farmaco, Edizione Scientifica (1978), vol. 33 (12), pp. 963-971, Abstract in CAPLUS, Accession No. 1979:152086.

Rulliere et al., "Kryton Fluoride Laser Pumps New Dyes in the 3500 A Spectral Range," Optics Communications (1977), vol. 20(3), pp. 339-341, Abstract in CAPLUS, Accession No. 1977:180337.

* cited by examiner

ELECTRON TRANSPORT AGENTS FOR ORGANIC ELECTRONIC DEVICES

TECHNICAL FIELD

This invention relates to compounds, compositions, organic electronic devices, and methods for preparing organic electronic devices. More particularly, the invention relates to compounds and compositions that can be used as electron transport agents in organic electronic devices such as organic electroluminescent devices.

BACKGROUND

Organic electroluminescent (OEL) devices such as organic light emitting diodes (OLEDs) are desirable for use in electronic media because of their thin profile, low weight, capability of obtaining a wide variety of emission colors, and low driving voltage. OLEDs have potential use in applications such as backlighting of graphics, pixelated displays, and large emissive graphics.

There is continuing research and development of electroluminescent materials, electroactive materials, and charge transporting materials suitable for such devices and methods for making the devices. In some instances, materials can be selected or developed which facilitate one or more of these device preparation methods. Pattern-wise thermal transfer of materials from donor sheets to receptor substrates has been proposed as one method for forming OEL devices. Selective thermal transfer of organic light emitters for formation of organic electroluminescent devices has been shown to be particularly useful.

Molecular oxadiazole and triazole derivatives have been used as electron transport/hole blocking materials in OLED devices. One oxadiazole derivative commonly used is 2-(4-biphenyl)-5-(4-t-butylphenyl)-1,3,4-oxadiazole (PBD). One triazole derivative commonly used is 3-(4-biphenylyl)-4-phenyl-5-(4-tert-butylphenyl)1,2,4-triazole (TAZ). However, OLED devices employing PBD or TAZ often exhibit short operating lifetimes due to recrystallization of or aggregate formation by the PBD or TAZ, leading to phase separation and formation of charge carrier traps that inhibit emission.

In an effort to mitigate these problems in blended polymer systems, several groups have reported bonding an electron transporting structure such as PBD to a flexible polymer chain, resulting in amorphous materials. For example, polymethylmethacrylates bearing oxadiazole side chains have been reported. However, operating lifetimes for devices based on these materials were found to be extremely short due to PBD aggregation (e.g., see Strukelj et al., *Science*, 267, 1969, (1995)).

SUMMARY OF THE INVENTION

This invention relates to compounds, compositions, organic electronic devices, and methods for preparing organic electronic devices. More particularly, the invention relates to compounds and compositions that contain an arylene group having a pendant heteroaryl group that includes a —C=N— unit. The compounds can be used as electron transport agents in organic electronic devices such as organic electroluminescent devices.

One aspect of the invention provides a compound having an aromatic core and two end capping groups that are conjugated to the aromatic core according to Formula I:

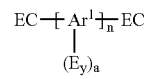

wherein
each $Ar^1$ is independently a phenylene group arylene or a naphthalene group arylene that is unsubstituted or substituted with one or more groups selected from alkyl, alkenyl, alkoxy, aryl, aryloxy, fluoro, fluoroalkyl, perfluoroalky, heteroalkyl, heteroaryl, and combinations thereof;
each a is independently 1 or 2;
each $E_y$ is independently a structure of Formula II or Formula III:

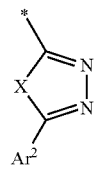

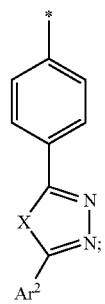

each X is independently O, S, or $NR^1$, where $R^1$ is alkyl, aryl, heteroaryl, heteroalkyl, or combinations thereof;
each $Ar^2$ is independently a carbocyclic aryl group that is unsubstituted or substituted with one or more groups selected from alkyl, alkenyl, alkoxy, aryl, aryloxy, fluoro, fluoroalkyl, perfluoroalkyl, heteroalkyl, heteroaryl, alkyl oxadiazolyl, aryl oxadiazolyl, alkyl triazolyl, aryl triazolyl, diarylamino, aryldiarylamino, and combinations thereof;
each asterisk (-*) indicates the location of a bond to another group in the compound;
n is an integer equal to 1 or 2; and
each end capping group (EC) is independently a carbocyclic aryl, heteroaryl, or tertiary amino aryl group that is unsubstituted or substituted with one or more groups selected from alkyl, alkenyl, alkoxy, aryl, aryloxy, fluoro, fluoroalkyl, perfluoroalkyl, heteroalkyl, heteroaryl, and combinations thereof, wherein no more than one EC is a group of Formula II or Formula III.

Another aspect of the invention provides a composition that includes a compound according to Formula I in combination with at least one other compound that is a charge transporting material, charge blocking material, light emitting material, color conversion material, polymeric binder, or combination thereof.

Yet another aspect of the invention provides an organic electronic device that includes a compound according to Formula I. In some embodiments, the organic electronic device is an organic electroluminescent device.

Additionally, the invention provides a method of making an organic electroluminescent device. The method includes (1) preparing a donor sheet that includes a transfer layer containing a compound according to Formula I and (2) transferring the transfer layer to a surface of a receptor substrate.

The above summary of the present invention is not intended to describe each disclosed embodiment or every implementation of the present invention. The Figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
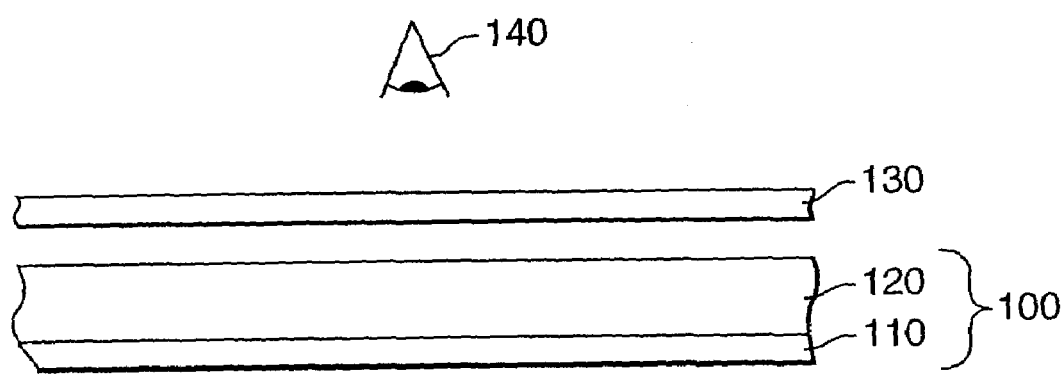
FIG. 1 is a schematic side view of an organic electroluminescent display construction.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

Definitions

As used herein, the terms "a", "an", and "the" are used interchangeably with "at least one" to mean one or more of the elements being described.

As used herein, the term "active" when used to refer to a compound means that the compound can transport holes, transport electrons, participate in electron/hole recombination, emit light, or a combination thereof.

As used herein, the term "amorphous" refers to a compound or composition that is not crystalline and that does not crystallize when removed from a solvent.

As used herein, the term "alkyl" includes both straight-chained, branched, and cyclic alkyl groups that are unsubstituted or substituted. The alkyl group typically has 1 to about 30 carbon atoms. In some embodiments, the alkyl group contains 1 to about 20 or 1 to about 10 carbon atoms. Examples of alkyl groups include, but are not limited to, methyl, ethyl, n-propyl, n-butyl, n-pentyl, tert-butyl, isopropyl, isobutyl, n-octyl, n-heptyl, and ethylhexyl.

As used herein, the term "alkenyl" refers to a monovalent radical of a straight-chained, branched, or cyclic alkene having one or more aliphatic carbon-carbon double bond and includes both unsubstituted and substituted alkenyl groups. The alkenyl groups typically include 2 to about 30 carbon atoms. In some embodiments, the alkenyl groups contain 2 to about 20 or 2 to about 10 carbon atoms. Examples of alkenyl groups include, but are not limited to, n-oct-3-enyl and n-hept-6-enyl. The alkenyl groups can have alternating double and single carbon-carbon bonds. For example, the alkenyl groups can be a diene or a triene with a single carbon-carbon bond between each carbon-carbon double bond.

As used herein, the term "alkylene" includes both straight-chained, branched, and cyclic divalent hydrocarbon radicals and includes both unsubstituted and substituted alkylene groups. The alkylene groups are typically include up to about 30 carbon atoms. In some embodiments, the alkylene groups contain up to about 20 or up to about 10 carbon atoms. Examples of "alkylene" as used herein include, but are not limited to, methylene, ethylene, propylene, butylene, and isopropylene, and the like.

As used herein, the term "alkoxy" refers to a group having an oxygen atom attached to an alkyl group. The alkoxy group typically has 1 to about 30 carbon atoms. In some embodiments, the alkoxy group contains 1 to about 20 or 1 to about 10 carbon atoms. Examples include methoxy, ethoxy, propoxy, butoxy, and the like. An alkoxy is a subset of a heteroalkyl group. Alkoxy groups can be unsubstituted or substituted.

As used herein, the term "aromatic" refers to both a carbocyclic aromatic compound or group, a silicon-containing aromatic compound or group, and a heteroaromatic compound or group. A carbocyclic aromatic compound is a compound that contains only carbon atoms in the aromatic ring structure. A silicon-containing aromatic compound is a compound that contains at least one Si in the aromatic ring structure. A heteroaromatic compound is a compound that contains at least one heteroatom selected from S, O, N and P in in the aromatic ring structure.

As used herein, the term "aryl" refers to monovalent unsaturated aromatic carbocyclic radicals or to monovalent unsaturated silicon-containing aromatic radicals having one to ten rings, multiple fused rings, or combinations thereof. That is, an aryl is a monovalent radical of a carbocyclic aromatic compound or a monovalent radical of a silicon-containing aromatic compound. In some embodiments, the aryl group has up to 10 rings, up to 8 rings, up to 6 rings, up to 4 rings, up to 3 rings, up to 2 rings, or one aromatic ring. The aryl group can contain, for example, up to about 60, up to about 50, up to about 40, up to about 30, or up to about 20 carbon atoms. Examples of and groups include, but are not limited to, phenyl, biphenyl. terphenyl, anthryl, naphthyl, acenaphthyl, phenanthryl, dihydrophenathrenyl, anthracenyl, fluorenyl, 9-silafluorenyl, tetrahydropyrenvi, perylenyl, spirobisfluorenyl, fluoranthenyl, pyrenyl, dihydropyrenyl, tetrahydropyrenyl, rubrenyl, chrysenyl, 5,6,12,13-tetrahydrodibeuzo[a,h]anthracenyl, 6,12-dihydroindeno[1,2-b]fluorenyl, 5,12-dihydro-6H-indeno[1,2-b]phenathrenyl, dihydrophenathrenyl, and benzo[g,h,I]pyrenyl.

As used herein, the term "arylene" refers to divalent unsaturated aromatic carbocyclic radicals or to divalent unsaturated silicon-containing aromatic radicals having one to ten rings, multiple fused rings, or combinations thereof. That is, an arylene is a divalent radical of a carbocyclic aromatic compound or a divalent radical of a silicon-containing aromatic compound. In some embodiments, the arylene group has up to 8 rings, up to 6 rings, up to 4 rings, up to 3 rings, up to 2 rings, or one aromatic ring. In some examples, the arylene group contains up to 60 carbon atoms, up to 50 carbon atoms, up to 40 carbon atoms, up to 30 carbon atoms, or up to 20 carbon atoms. Examples of arylene groups include, but are not limited to, divalent radicals of benzene, naphthalene, acenaphthene, phenanthrene, anthracene, fluorene, 9-silafluorene, fluoranthene, benzopyrene, aromatic corene, dihyrophenanthrene tetrahydropyrene, perylene, spirobisfluorene, pyrene, rubrene, and chrysene. Specific examples of arylene groups include benzene-1,3-diyl, benzene-1,4-diyl, naphthalene-2,7-diyl, naphthalene-2,6-diyl, naphthalene-1,4-diyl naphthalene-1,5-diyl, acenaphthene-diyl, phenanthren-3,8-diyl, 5,6-dihydrophenathren-3,8-diyl, 4,5,9,10-tetrahydropyren-2,7-diyl, pyren-2,7-diyl, fluoren-2,7-diyl, 9-silafluoren-2,7-diyl, anthracene-9,10-diyl, perylene-3,9 diyl, perylene-3,10-diyl, spirobisfluorene-diyl, 5,6,12,13-tetrahydrodibenzo[a,h]anthracene-3,10-diyl, fluoranthene-diyl, rubrene-diyl, chrysene-diyl, benzo[g,h,I]perylene-diyl, and the like.

As used herein, the term "aryloxy" refers to a group having an oxygen atom attached to an aryl group. An example includes, but is not limited to, phenoxy.

An asterisk (-*) in any formula infra indicates the location of a bond to another group in a molecule.

As used herein, the term "carbocyclic" refers to a ring formed of carbon atoms. There are no heteroatoms in the ring structure.

As used herein, the term "condensed polycyclic arylene" is a subset of the arylenes and refers to divalent arylene groups having 3 to about 10 fused rings. In some embodiments, the condensed polycyclic arylene contains up to about 8 fused rings, up to about 6 fused rings, up to about 4 fused rings, or 3 fused rings. Examples of condensed polycyclic arylene groups include, but are not limited to, divalent radicals of phenanthrene, anthracene, fluoranthene, pyrene, perylene, benzoperylene, rubrene, chrysene, aromatic corene, and the like.

As used herein, the term "conjugated" refers to unsaturated compounds having at least two carbon-carbon double or triple bonds with alternating carbon-carbon single bonds and carbon-carbon double or triple bonds. Likewise, the term "unconjugated" refers to unsaturated compounds that are not conjugated. For example, an unconjugated aromatic group can have two or more carbon-carbon single bonds interrupting alternating carbon-carbon single bonds and carbon-carbon double or triple bonds.

As used herein, the term "electroactive" refers a compound that transports holes, transports electrons, or participates in an electron/hole recombination.

As used herein, "electrochemically stable" is meant stable to electrochemical degradation such that any oxidation and/or reduction reactions entered into are reversible.

As used herein, the term "fluoroalkyl" refers to an alkyl group that has at least one hydrogen atom replaced with a fluorine atom.

As used herein, the term "heteroalkyl" includes both straight-chained, branched, and cyclic alkyl groups with one or more heteroatoms independently selected from S, O, N, P, or Si replacing a carbon atom. The heteroalkyl group typically contains 1 to about 30 carbon atoms and can have up to 10 heteroatoms. In some embodiments, the heteroalkyl group contains 1 to about 20 or 1 to about 10 carbon atoms. An alkoxy group is a subset of a heteroalkyl group. Examples of heteroalkyl groups include, but are not limited to, methoxy, ethoxy, propoxy, 3,6-dioxaheptyl, 3-(trimethylsilyl)-propyl, poly(oxyalkylene) groups having a segment of formula $-O(C_mH_{2m}O)_y-$ where m is an integer of 1 to 6 and y is an integer of 2 to 20, and poly(dialkylsiloxane) groups having a segment of formula $-[Si(C_wH_{2w+1})_2O]_y-$ where w is an integer of 1 to 10 and y is an integer of 2 to 20. Heteroalkyl groups can be unsubstituted or substituted.

As used herein, the term "heteroaryl" refers to a monovalent radical of a five to seven member aromatic ring that includes one or more heteroatoms independently selected from S, O, N and P in ring. That is, a heteroaryl is a monovalent radical of a heteroaromatic compound. Such a heteroaryl ring can be fused to one or more rings and can contain one to about 10 other rings selected from another heterocyclic ring(s), heteroaryl ring(s), aryl ring(s), cycloalkenyl ring(s), cycloalkyl rings, and combinations thereof. In some embodiments, the heteroaryl ring has to up to 8 other rings, up to 6 other rings, up to 4 other rings, up to 3 other rings, up to 2 other rings, or one other ring. The heteroaryl typically contains up to about 60 carbon atoms. In some embodiments, the heteroaryl contains up to about 50 carbon atoms, up to about 40 carbon atoms, up to about 30 carbon atoms, or up to about 20 carbon atoms. Examples of heteroaryl groups include, but are not limited to, furanyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, carbazoyl, benzoxazolyl, benzothiazolyl, benzimidazolyl, cinnolinyl, quinazolinyl, quinoxalinyl, phthalazinyl, benzothiadiazolyl, benzotriazinyl, phenazinyl, phenanthridinyl, acridinyl, and indazolyl, siloles, and the like.

As used herein, "heteroaryls having a —C═N— unit" is a subset of the heteroaryls and refers to heteroaryls that have a —C═N— unit in at least one heteroaromatic ring. Examples of suitable include, but are not limited to, oxadiazolyls, N-substituted-triazolyls, N-substituted imidazolyls, N-substituted pyrazolyls, oxazolyls, isooxazolyls, thiazolyls, isothiazolyls, pyridinyls, pyridazinyls, pyrimidinyls, pyrazinyls, triazinyls, tetrazenyls, benzoxazolyls, benzothiazolyls, benzothiadiazolyls, quinolinyls, isoquinolinyls, cinnolinyls, quinazolinyls, quinoxalinyls, phthalazinyls, benzotriazinyls, phenazinyls, phenanthridinyls, acridinyls, and the like.

As used herein, "heteroaryls that are electron rich" is a subset of the heteroaryls and refers to heteroaryls that can donate electron density from the heteroatom into a pi bonding system. Examples include, but are not limited to, monovalent radicals of diarylsilanolyls, thiophenyls, bithiophenyls, furanyls, N-alkyl carbazolyl, N-aryl carbazolyl, N-alkyl pyrrolyl, N-aryl pyrrolyl, and the like.

As used herein, the term "heteroarylene" refers to an aromatic divalent radical of a five to seven member aromatic ring that includes one or more heteroatoms independently selected from S, O, N, and P. That is, a heteroarylene is divalent radical of a heteroaromatic compound. Such a heteroaromatic ring can be fused to one or more rings and can contain 1 to about 10 other rings selected from another heterocyclic ring(s), heteroaryl ring(s), aryl ring(s), cycloalkenyl ring(s), cycloalkyl rings, and combinations thereof. In some embodiments, the heteroaromatic ring is fused to up to 8 other rings, up to 4 other rings, up to 3 other rings, up to 2 other rings, or one other ring. The heteroarylene typically contains up to about 60 carbon atoms. In some embodiments, the heteroarylene contains up to about 50 carbon atoms, up to about 40 carbon atoms, up to about 30 carbon atoms, or up to about 20 carbon atoms.

Examples of heteroarylene groups include, but are not limited to, divalent radicals of furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, carbazole, benzoaxazole, benzothizole, benzimidiazole, cinnoline, quinazoline, quinoxaline, phthalazine, benzothiadiazole, benzotriazine, phenazine, phenanthridine, acridine, indazole, and silones. Specific examples of heteroarylenes include, but are not limited to, furan-2,5-diyl, thiophene-2,4-diyl, 1,3,4-oxadiazole-2,5-diyl, 1,3,4-thiadiazole-2,5-diyl, 1,3-thiazole-2,4-diyl, benzo[ 1,2,5]thiadiazole-4,7-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, 1,1-dialkyl-1H-silole-2,5-diyl, and the like.

As used herein, "heteroarylenes having —C=N— units" is a subset of heteroarylenes and refers to heteroarylenes having a —C=N— unit in at least one heteroaromatic ring. Examples of heteroarylenes having —C=N— units include, but are not limited to, divalent radicals of oxadiazoles, N-substituted-triazoles, N-substituted imidazoles, N-substituted pyrazoles, oxazoles, isoxazole, thiazoles, isothiazoles, pyridines, pyridazines, pyrimidines, pyrazines, triazines, tetrazenes, benzoxazoles, benzothiazoles, benzothiadiazoles, quinolines, isoquinolines, cinnolines, quinazolines, quinoxalines, phthalazines, benzotriazines, phenazines, phenanthridines, acridines, and the like.

As used herein, "heteroarylenes that are electron rich" is a subset of heteroarylenes and refers to heteroarylenes that can donate electron density from the heteroatom into a pi bonding system. Suitable examples include divalent radicals of diarylsilanoles, thiophenes, bithiophenes, furans, N-alkyl carbazoles, N-aryl carbazoles, N-alkyl pyrroles, N-aryl pyrroles, and the like.

As used herein, the term "inactive" when used to refer to a compound means that the compound is not electroactive, not electroluminescent, or a combination thereof.

As used herein, the term "naphthalene group aryl" is a subset of an aryl group and refers to monovalent unsaturated aromatic carbocyclic radicals having a fused naphthalene ring structure. An unsubstituted naphthalene group aryl has two fused aromatic rings. Examples of naphthalene group aryl include naphthalen-2-yl, naphthalen-1-yl, naphthalen-7-yl, naphthalen-6-yl, naphthalen-4-yl, naphthalen-5-yl, acenaphthenyl, and the like.

As used herein, the term "naphthalene group arylene" is a subset of arylene groups and refers to divalent unsaturated aromatic carbocyclic radicals having a fused naphthalene ring structure. An unsubstituted naphthalene group arylene has two carbocyclic aromatic rings. Examples of naphthalene group arylenes include, but are not limited to, naphthalene-2,7-diyl, naphthalene-2,6-diyl, naphthalene-1,4-diyl, naphthalene-1,5-diyl, acenaphthene-diyl, and the like.

As used herein, the term "perfluoroalky" refers to an alkyl group that has all the hydrogen atoms replaced with fluorine atoms. A perfluoroalkyl is a subset of a fluoroalkyl.

As used herein, the term "phenylene group aryl" is a subset of aryl and refers to monovalent unsaturated aromatic carbocyclic radicals having one, two, or three conjugated phenyl or phenylene rings (e.g. phenyl, biphenyl, and terphenyl) that are optionally fused with divalent radicals of alkylene or di-substituted silylene (—Si(R)$_2$-) where each R is independently selected from a $C_{1-30}$ alkyl, $C_{2-30}$ alkenyl, $C_{1-30}$ alkoxy, $C_{6-20}$ aryl, $C_{6-20}$ aryloxy, $C_{1-30}$ heteroalkyl, $C_{3-20}$ heteroaryl, fluoro, $C_{1-30}$ fluoroalkyl, $C_{1-30}$ perfluoroalkyl, and combinations thereof. An unsubstituted phenylene group aryl has up to three carbocyclic aromatic rings. Examples of suitable phenylene group aryls include, but are not limited to, phenyl, biphenyl, terphenyl, 5,6-dihydrophenathrenyl, 4,5,9,10-tetrahydropyrenyl, fluorenyl, 9-silafluorenyl, spirobisfluorenyl, 6,12-dihydroindeno[1,2-b]fluorenyl, 5,12-dihydro-6H-indeno[1,2-b]phenathrenyl, 5,6,12,13-tetrahydrodibenzo[a,h]anthracenyl, and the like.

As used herein, the term "phenylene group arylene" is a subset of arylene groups and refers to divalent unsaturated aromatic carbocyclic radicals having one, two, or three conjugated phenylene rings (e.g. phenylene, biphenylene, and terphenylene) that are optionally fused with divalent radicals of alkylene or di-substituted silylene (—Si(R)$_2$-) where each R is independently a $C_{1-30}$ alkyl, $C_{2-30}$ alkenyl, $C_{1-30}$ alkoxy, $C_{6-20}$ aryl, $C_{6-20}$ aryloxy, $C_{1-30}$ heteroalkyl, $C_{3-20}$ heteroaryl, fluoro, $C_{1-30}$ fluoroalkyl, and $C_{1-30}$ perfluoroalkyl, and combinations thereof. An unsubstituted phenylene group arylene has up to three carbocyclic aromatic rings. Examples of phenylene group arylene include, but are not limited to, benzene-1,3-diyl, benzene-1,4-diyl, phenanthren-3,8-diyl, 5,6-dihydrophenathren-3,8-diyl, 4,5,9,10-tetrahydropyren-2,7-diyl, fluoren-2,7-diyl, 9-silafluoren-2,7-diyl, spirobisfluoren-2,7-diyl, 6,12-dihydroindeno[1,2-b ] fluorene-2,8-diyl, 5,12-dihydro-6H-indeno[1,2-b]phenathrene-3,10-diyl, 5,6,12,13-tetrahydrodibenzo[a,h]anthracene-3,10-diyl, and the like.

As used herein, the term "small molecule" refers to a compound that is non-polymeric (e.g., less than three repeating units when there are repeating units).

As used herein the term "solution processible" refers to a compound or composition that can be dissolved in a solution. In some embodiments, a compound or composition that is solution processible can be coated from a solution as a thin film. In other embodiments, a solution of the compound of composition can be applied to a substrate. For example, the solution can be printed or coated onto a substrate.

As used herein, the term "tertiary aromatic amine" refers to alkyl, alkenyl, alkoxy, aryl, aryloxy, heteroalkyl, heteroaryl, fluoro, fluoroalkyl, perfluoroalkyl, and the like. The various groups in Formula I can be substituted, for example, with one or more groups selected $C_{1-30}$ alkyl, $C_{2-30}$ alkenyl, $C_{1-30}$ alkoxy, $C_{6-20}$ aryl, $C_{6-20}$ aryloxy, $C_{1-30}$ heteroalyl, $C_{3-20}$ heteroaryl, fluoro, $C_{1-30}$ fluoroalkyl, and $C_{1-30}$ perfluoroalkyl.

As used herin, the term "tertiary aromatic amine" refers to a class of molecular compounds having one or more tertiary nitrogen centers and each nitrogen center is bonded to three aromatic carbon centers. Examples of tertiary aromatic amines include diarylanilines; alkyl carbazole; aryl carbazole; and tetranryldiamines such as, for example, N,N,N'N'-tetraarylbenzidines, N,N,N',N' tetraaryl-1,4-phenylenediamines, N,N,N'N' tetraryl-2,7-diaminofluorene derivatives such as those taught in patent applications EP 0 953 624 A1 and EP 0 879 868 A2, N,N'-bis(3-methylphenyl)-N,N'-bis(phenyl)benzidine (also known as TPD), N,N'-bis(3-naphthalen-2-yl)-N,N'-bis(phenyl)benzidine (also known as NPB), 1,4-bis(carbazolyl)biphenyl (also known as CBP), and other tetraaryldiamine derivatives such as those described in B. E. Koene et al., *Chem. Mater.,* 10, 2235-2250 (1998), U.S. Pat. No. 5,792,557, U.S. Pat. No. 5,550,290 and patent application EP 0 891 121 A1; peraryltriamine derivatives such as those described in U.S. Pat. No. 6,074,734 and patent application EP 0 827 367 A1; starburst amine derivatives such as 4,4',4"-tris(N,N-diarylamino)triphenylamines and 1,3,5-tris(4-diarylaminophenyl)benzenes, 4,4',4"-tris(N, N-diphenylamino)triphenylamine (also known as TDATA), 4,4',4"-tris(N-3-methylphenyl-N-phenylamino)triphenylamine (also known as mTDATA); 1,3,5-Tris(4-diphenylaminophenyl)benzencs (TDAPBs); and other dendridic and spiro amine derivatives as taught in patent application EP 0 650 955 A1, Tokito et al., *Polym. Prep.* (Am. Chem. Soc. Div. Polym. Chem.) 38(1), 388-389 (1997), Tanaka et al., Chem Commun., 2175-2176 (1996), and Tokito et al., *Phys. Lett,* 70(15), 1929-1931 (1997).

As used herein, the term "tertiary aromatic amino aryl" refers to a monovalent aromatic ring radical of a tertiary aromatic amine as defined above.

As used herein, the term "tertiary aromatic amino arylene" refers to a divalent unsaturated aromatic carbocyclic radical of a tertiary aromatic amine as defined above.

Compounds

One aspect of the invention provides compounds that have an aromatic core and two end capping groups (EC) that are conjugated to the aromatic core. The aromatic core contains a phenylene group arylene or a naphthalene group arylene having a pendant heteroaryl group that includes a —C=N— unit. The compounds can be used in organic electronic devices. For example, the compounds can be used as electron transport materials in organic electronic devices such as organic electroluminescent devices.

The compounds have a structure according to Formula I:

I wherein
each $Ar^1$ is independently a phenylene group arylene or a naphthalene group arylene that is unsubstituted or substituted with one or more groups selected from alkyl, alkenyl, alkoxy, aryl, aryloxy, fluoro, fluoroalkyl, perfluoroalky, heteroalkyl, heteroaryl, and combinations thereof;
each a is independently 1 or 2;
each $E_y$ is independently a structure of Formula II or Formula III:

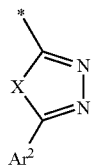

II

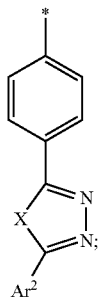

III each X is independently O, S, or $NR^1$, where $R^1$ is alkyl, aryl, heteroaryl, heteroalkyl, or combinations thereof;

each $Ar^2$ is independently a carbocyclic aryl group that is unsubstituted or substituted with one or more groups selected from alkyl, alkenyl, alkoxy, aryl, aryloxy, fluoro, fluoroalkyl, perfluoroalkyl, heteroalkyl, heteroaryl, alkyl oxadiazolyl, aryl oxadiazolyl, alkyl triazolyl, aryl triazolyl, diarylamino, aryldiarylamino, and combinations thereof;
each asterisk (-*) indicates the location of a bond to another group in the compound;
n is an integer equal to 1 or 2; and
each end capping group (EC) is independently a carbocyclic aryl, heteroaryl, or tertiary amino aryl group that is unsubstituted or substituted with one or more groups selected from alkyl, alkenyl, alkoxy, aryl, aryloxy, fluoro, fluoroalkyl, perfluoroalkyl, heteroalkyl, heteroaryl, and combinations thereof, wherein no more than one EC is a group of Formula II or Formula III.

As used herein, the term "aromatic core" refers to that portion of the compound of Formula I that is not an end capping group. The aromatic core can include carbocyclic arylene groups, heteroarylene groups, tertiary aromatic amino arylene groups, and combinations thereof. The term aromatic core does not imply any particular synthesis method or order of synthesis.

The compound of Formula I can be a compound of Formula IV or V:

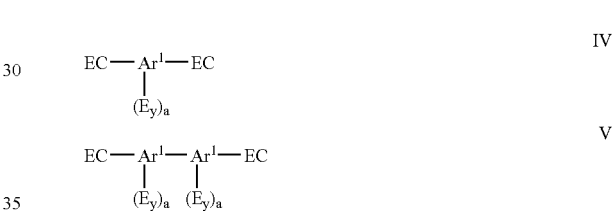

The end capping groups (EC) can be the same or different.

The compounds can be solution processible and formed into thin film for use in organic electronic devices. In some embodiments, the end capping groups and the aromatic core can be chosen to provide a compound that is amorphous.

The compounds of Formula I can be used as electron transport agents in organic electronic devices. The aromatic core contains at least one heteroaryl group having a —C=N— unit (i.e., Ey in Formula I). A —C=N— unit tend to be electron deficient compared to a carbon-carbon double bond. In some embodiments, the —C=N— unit can provide electron transport and electron injection properties to the compounds. The $Ar^1$ group and the end capping groups can be chosen to provide additional functions to the compounds. For example, in some embodiments, the compounds can be used as electron transport agents as well as hole transporting molecules. In other embodiments, the compounds can be used as electron transporting molecules as well as light emitting molecules.

Substituent groups can be on the $Ar^1$-$(E_y)_a$ group, the end capping groups, or a combination thereof. The substituents can be selected from alkyl, alkenyl, alkoxy, aryl, aryloxy, fluoro, fluoroalkyl, perfluoroalky, heteroalkyl, heteroaryl, and combinations thereof. In some embodiments, the compounds are substituted with a $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, and combinations thereof. For example, the compounds can be substituted with a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, a $C_{3-20}$ heteroaryl, and combinations thereof.

The substituent groups can enhance, for example, the solubility of the compounds in organic solvents, the compatibility of the compounds with other materials in a composition, the solution processibility, or a combination thereof. The substituents can modify the solubility parameter, modify the ionization potential, modify the electron affinity, reduce intramolecular or intermolecular interactions that can produce undesirable emissions, or any combination of these. For example, substituent groups can help suppress aggregation and phase separation of the compounds when the compounds are formed into thin films.

In some embodiments of the compounds of the invention, a substituent can include a divalent poly(oxyalkylene) soft segment of Formula VI

or a divalent poly(dialkylsiloxane) soft segment of Formula VII

where m is an integer of 1 to 6, y is an integer of 2 to 20, and w is an integer of 1 to 10. In some emdodiments, the poly(oxyalkylene) or poly(dialkylsiloxane) soft segment can be connected to an alkyl, aryl, or heteroaryl group. The substituent can, for example, have Formula VIII

where SS is a poly(oxyalkylene) or poly(dialkylsiloxane) soft segment, Ar is an arylene group, v is an integer of 0 or 1, and R" is an aryl, heteroaryl, or a alkyl. In some examples, R" is a sterically hindered group. Groups according to Formula VIII can reduce the formation of intermolecular or intramolecular configurations that produce undesirable excimer or exciplex emission.

In other embodiments, the compounds of the invention can be substituted with one or more groups selected from fluoro, $C_{1-30}$ fluoroalkyl, and $C_{1-30}$ perfluoroalky. These substituents can improve the solubility and the film forming properties of the compounds, can increase the ionization potential and electron affinity of the compounds, or a combination thereof. Compounds having an increased ionization potential and electron affinity can more easily inject electrons and block holes when used in organic electroluminescent devices. Fluoro, fluoroalkyl, or perfluoroalkyl substituents can also lower the vapor pressure of the compounds and make them easier to vapor deposit.

In some embodiments, substituents that are known to be photoluminescent quenchers, such as aryl carbonyls and nitro groups, may be undesirable because such groups can degrade the electroluminescent efficiency of organic electroluminescent devices. In some embodiments, substituents that are known to undergo electrochemical elimination reactions, such as alkyl amines, may be undesirable because such groups can degrade the operating lifetimes of organic electroluminescent devices. In some embodiments, substituents that contain titratable protons that can undergo electrochemical reactions, such as primary or secondary amines, phenols, alcohols, and the like, may be undesirable because such groups can be reduced to hydrogen during operation of an organic electroluminescent device. The generation of hydrogen can lead to delamination of the cathode and ultimate failure of the organic electroluminescent device. Chlorine, bromine, iodine, boronic acid, and boronic ester substituents can cause electrochemical instability in some embodiments. Such groups, if present in the compounds of the invention as impurities, should be present in amounts less than about 1000 parts per million (ppm) by weight. Additionally, groups such as parafluorophenyl may not be desirable in some applications because such groups are susceptible to irreversible electrochemical degradation. However, any of these groups can be included if other desirable characteristics can be obtained.

The compounds of the invention contain one or two groups of Formula IX

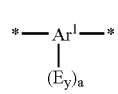

in the aromatic core. Each group of Formula IX is independently a phenylene group arylene or naphthalene group arylene. Suitable groups of Formula IX include, but are not limited to, a divalent radical of

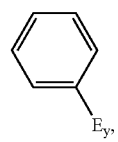

X

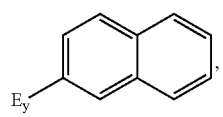

XI

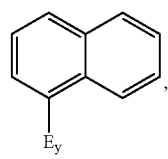

XII

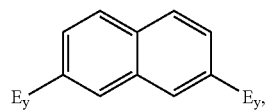

XIII

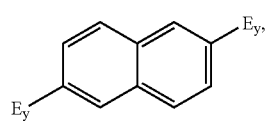

XIV

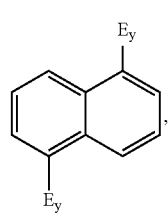

XV

-continued
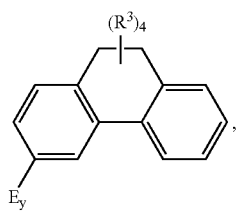, XVI
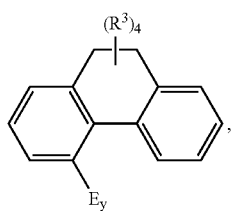, XVII
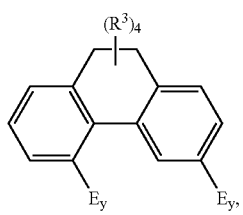, XVIII
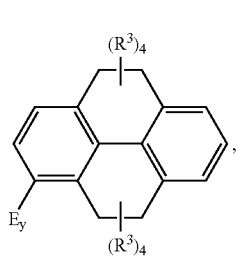, XIX
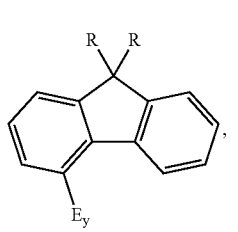, XX
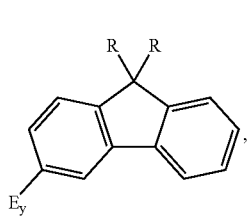, XXI
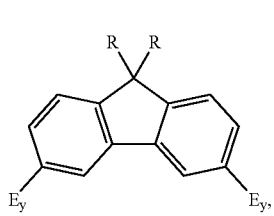, XXII
-continued
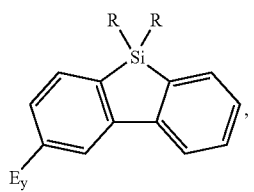, XXIII
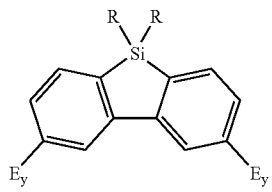, XXIV
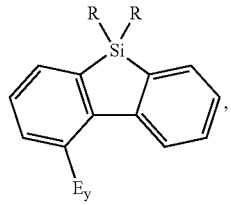, XXV
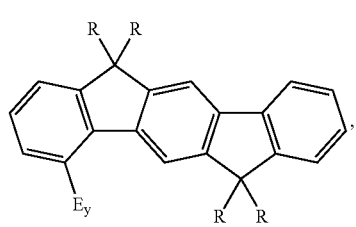, XXVI
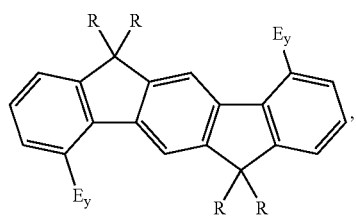, XXVI-a
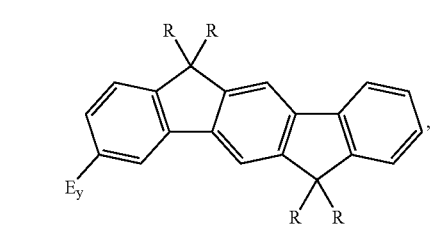, XXVII
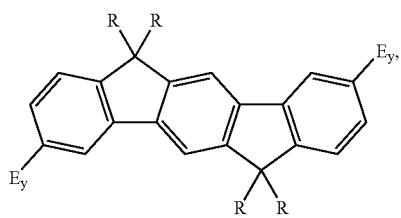, XXVIII -continued

XXIX

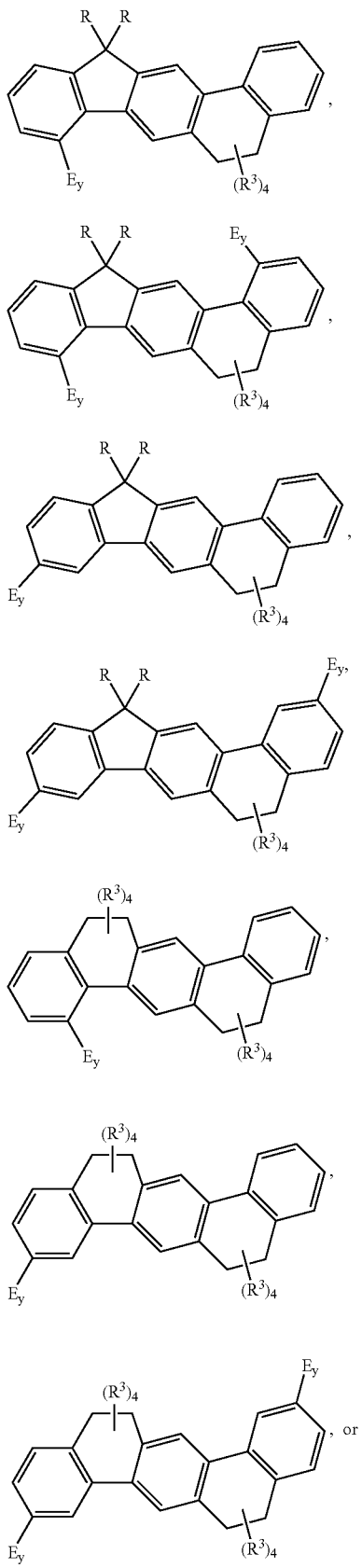

XXX

XXXI

XXXII

XXXIII

XXXIV

XXXV

-continued

XXXVI

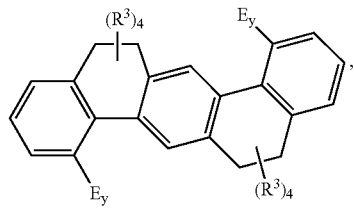

that is unsubstituted or substituted with one or more groups selected from a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently a $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl, $C_{1-30}$ heteroalkyl, and combinations thereof. Each $R^3$ is independently selected from hydrogen, $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl, $C_{1-30}$ heteroalkyl, and combinations thereof.

Any R or $R^3$ group in the aromatic core can include a divalent poly(oxyalkylene) soft segment of Formula VI $$*\!-\!O(C_mH_{2m}O)_y\!-\!* \qquad \text{VI}$$

or a divalent poly(dialkylsiloxane) soft segment of Formula VII $$*\!-\![\!-\!Si(C_wH_{2w+1})_2O\!-\!]_y\!-\!*, \qquad \text{VII}$$

where m is an integer of 1 to 6, y is an integer of 2 to 20, and w is an integer of 1 to 10. In some embodiments, the poly(oxyalkylene) or poly(dialkylsiloxane) soft segment can be connected to an alkyl, aryl, or heteroaryl group. The substituent can, for example, have Formula VIII $$*\!-\![\!-\!Ar\!-\!]_v\!-\!SS\!-\!R'' \qquad \text{VIII}$$

where SS is a poly(oxyalkylene) or poly(dialkylsiloxane) soft segment, Ar is an arylene group, v is an integer of 0 or 1, and R" is an aryl, heteroaryl, or a alkyl. In some examples, R" is a sterically hindered group. Groups according to Formula VIII can reduce the formation of intermolecular or intramolecular configurations that produce undesirable excimer or exciplex emission.

In some compounds, at least one divalent radical of Formula IX can be selected from

XXXVII

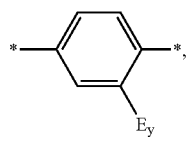

XXXVIII

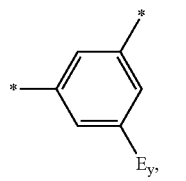

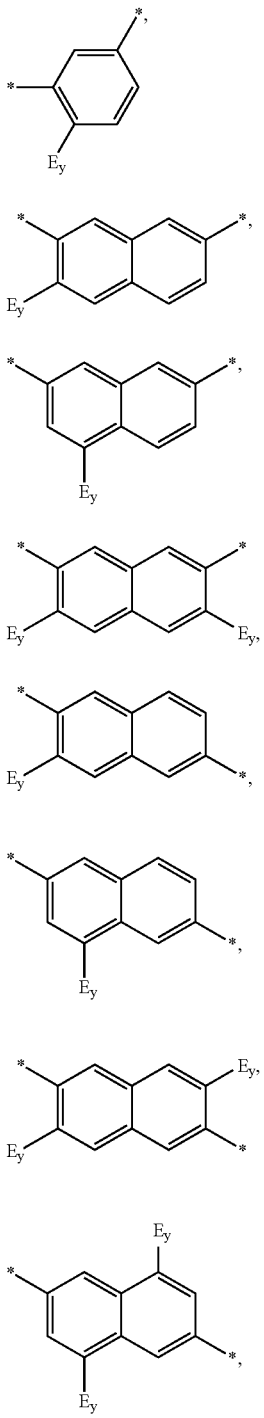
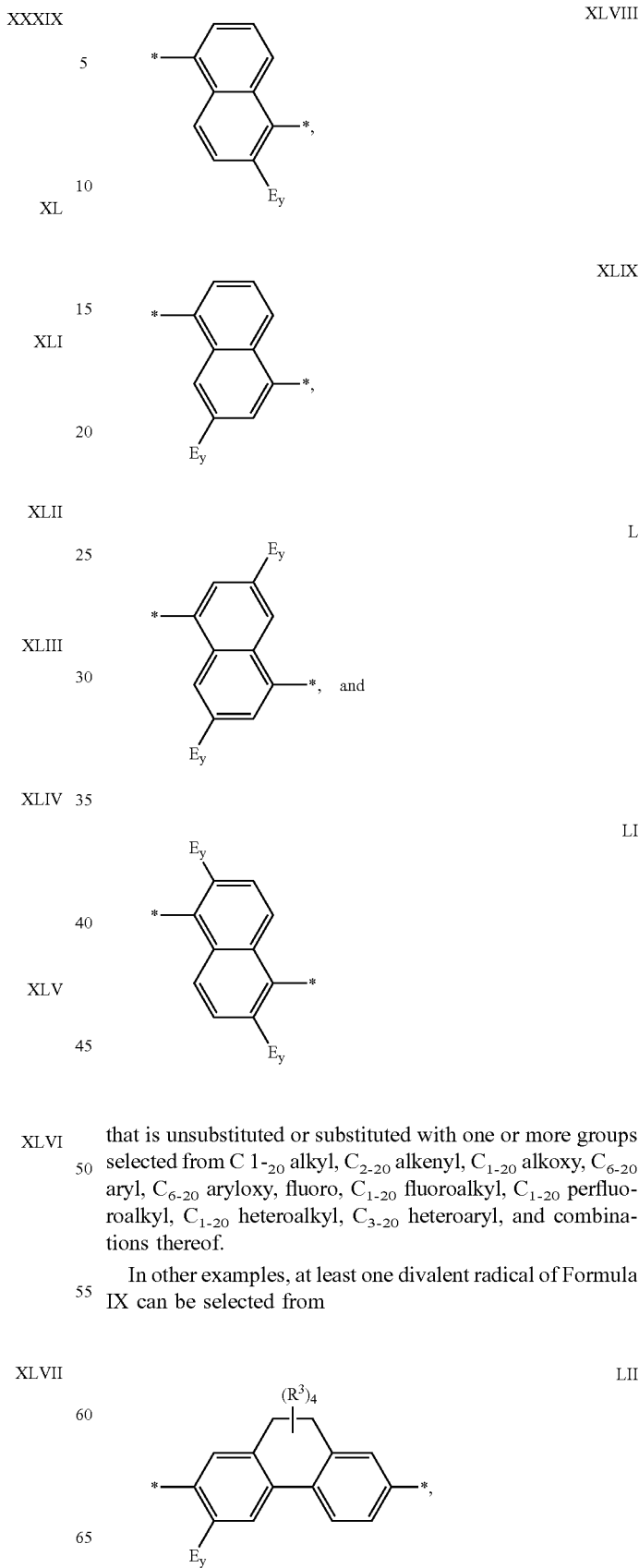
that is unsubstituted or substituted with one or more groups selected from C$_{1-20}$ alkyl, C$_{2-20}$ alkenyl, C$_{1-20}$ alkoxy, C$_{6-20}$ aryl, C$_{6-20}$ aryloxy, fluoro, C$_{1-20}$ fluoroalkyl, C$_{1-20}$ perfluoroalkyl, C$_{1-20}$ heteroalkyl, C$_{3-20}$ heteroaryl, and combinations thereof.
In other examples, at least one divalent radical of Formula IX can be selected from -continued

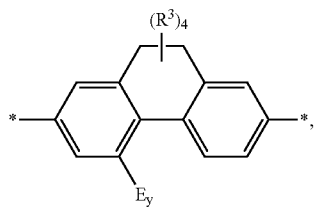
LIII

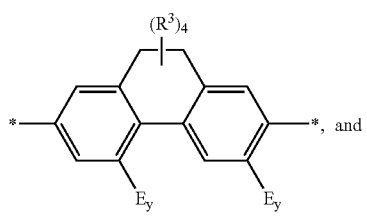
LIV

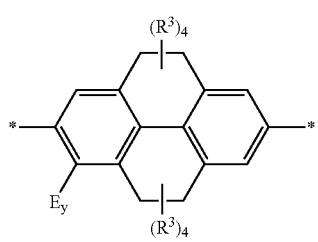
LV that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each $R^3$ is independently selected from hydrogen, $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl, $C_{1-30}$ heteroalkyl, and combinations thereof.

In yet other examples, at least one divalent radical of Formula IX is selected from

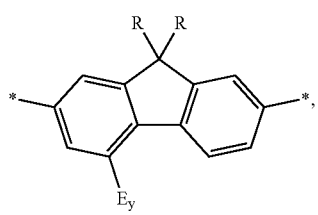
LVI

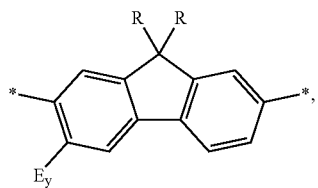
LVII

-continued

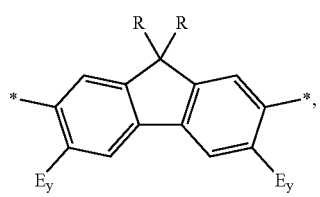
LVIII

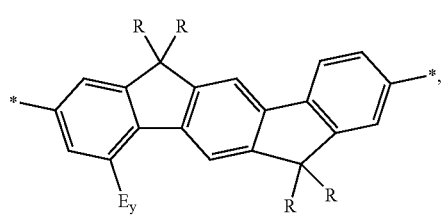
LIX

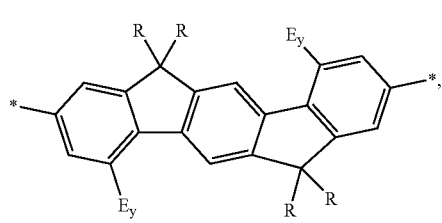
LX

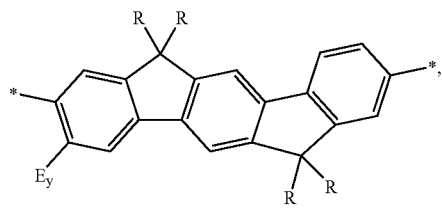
LXI

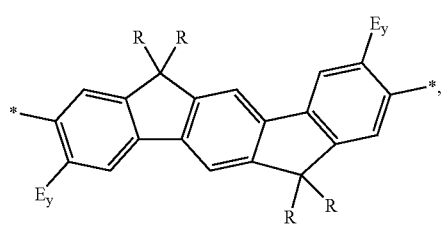
LXII

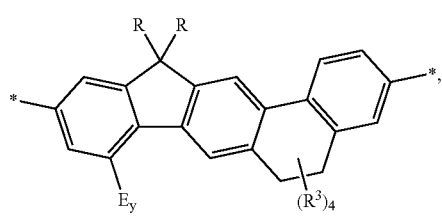
LXIII

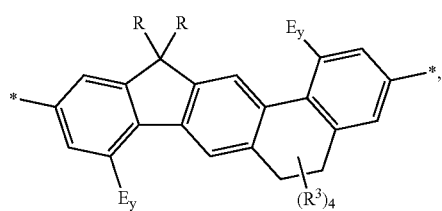
LXIV

-continued

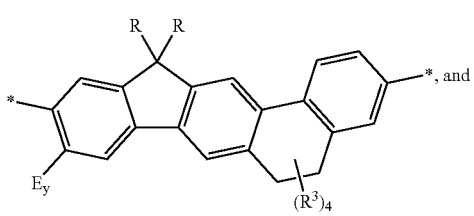

LXV

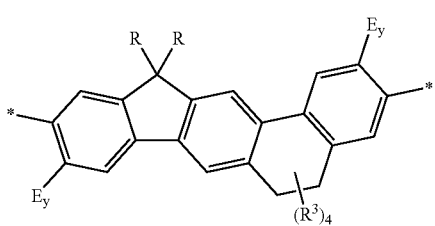

LXVI that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently selected from $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl, $C_{1-30}$ heteroalkyl, and combinations thereof. Each $R^3$ is independently selected from hydrogen, $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl, $C_{1-30}$ heteroalkyl, and combinations thereof.

Each $E_y$ in Formula I is a monovalent radical of Formula II or Formula III:

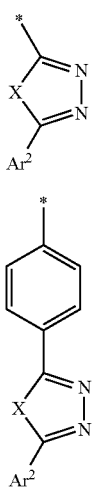

where each X is independently O, S, or NR', where R' is an alkyl, aryl, heteroaryl, heteroalkyl, or combinations thereof. Each $Ar^2$ in Formula II and Formula III is independently a carbocyclic aryl group. The $Ar^2$ group is typically a $C_{6-40}$ carbocyclic aryl group. The $Ar^2$ groups are bonded to the rest of $E_y$ through a carbocyclic aromatic ring included in Ar. That is, $Ar^2$ is conjugated to the heterocyclic ring in Formula II and Formula III.

In some embodiments, $Ar^2$ is an aryl group selected from phenyl, biphenyl, terphenyl, anthryl, naphthyl, acenaphthyl, phenanthryl, dihydrophenathrenyl, anthracenyl, fluorenyl, 9-silafluorenyl, tetrahydropyrenyl, perylenyl, spirobisfluorenyl, fluoranthenyl, pyrenyl, dihydropyrenyl, tetrahydropyrenyl, rubrenyl, chrysenyl, 5,6,12,13-tetrahydrodibenzo[a,h] anthracenyl, 6,12-dihydroindeno[1,2-b]fluorenyl, 5,12-dihydro-6H-indeno [1,2-b]phenathrenyl, dihydrophenathrenyl, and benzo[g,h,I]perylenyl that is unsubstituted or substituted with one or more $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, $C_{3-30}$ alkyl oxadiazolyl, $C_{3-30}$ aryl oxadiazolyl, $C_{3-20}$ alkyl triazolyl, $C_{3-30}$ aryl triazolyl, $C_{3-30}$ diarylamino, $C_{3-30}$ diarylaminoaryl, and combinations thereof.

Some embodiments of $Ar^2$ are substituted with one or more $C_{1-20}$ alkyl, $C_{1-20}$ alkoxy, $C_{6-20}$ aryl, $C_{6-20}$ aryloxy, $C_{1-20}$ fluoroalkyl, $C_{3-20}$ heteroaryl, $C_{3-30}$ alkyl oxadiazolyl, $C_{3-30}$ aryl oxadiazolyl, $C_{3-30}$ alkyl triazolyl, or $C_{3-30}$ aryl triazolyl. Examples of substituted $Ar^2$ groups include, for example, monovalent radicals of

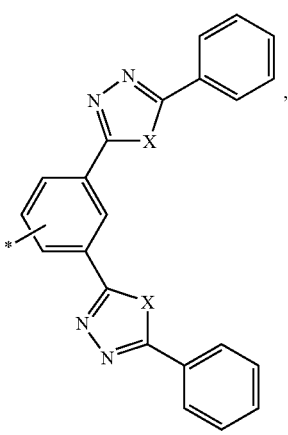

LXVII

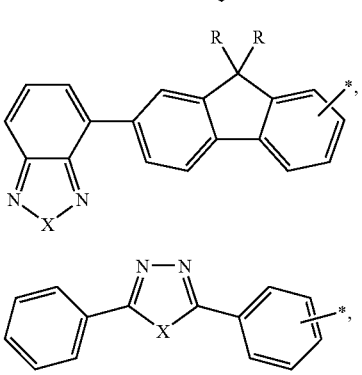

LXVIII

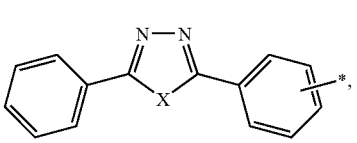

LXIX

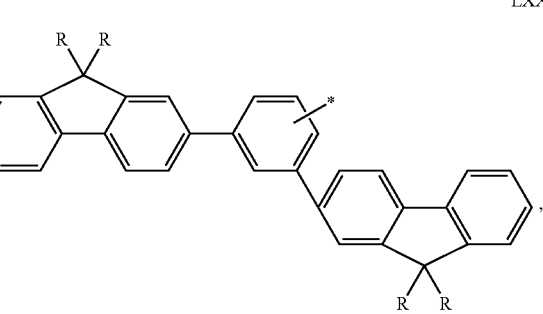

LXX and the like. Each X is independently O, S, or NR¹, where R¹ is a $C_{1-30}$ alkyl, $C_{6-20}$ aryl, $C_{3-30}$ heteroaryl, $C_{1-30}$ heteroalkyl, or combinations thereof. Each R is independently selected from $C_{1-30}$ alkyl, $C_{2-30}$ alkenyl, $C_{1-30}$ alkoxy, $C_{6-20}$ aryl, $C_{6-20}$ aryloxy, $C_{3-20}$ heteroaryl, $C_{1-30}$ heteroalkyl, and combinations thereof.

In some embodiments, X is in the heterocyclic ring of Formula II or Formula III is sulfur or oxygen.

Specific examples of the divalent radical

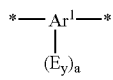

IX in Formula I include, but are not limited to,

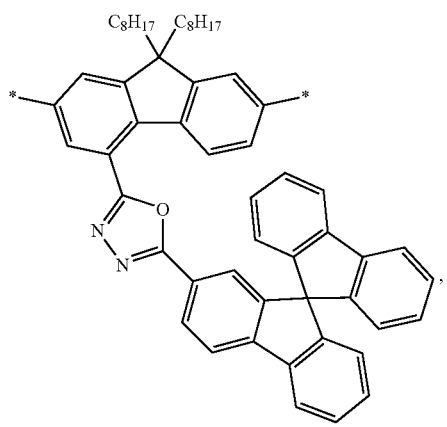

LXXI

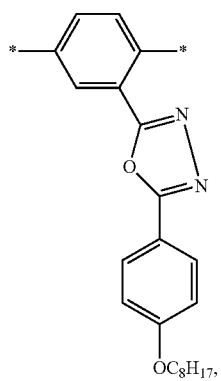

LXXII

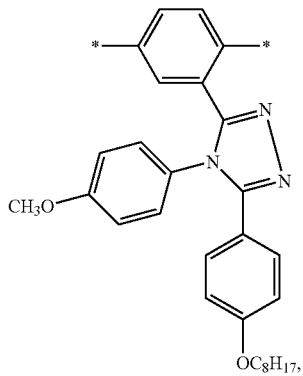

LXXIII

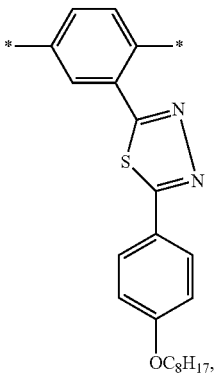

LXXIV

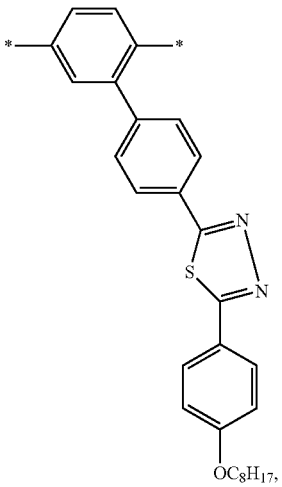

LXXV

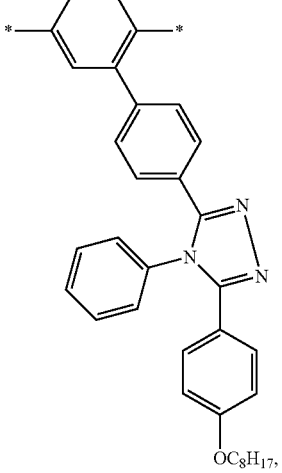

LXXVI

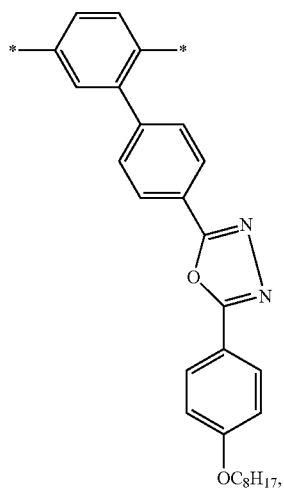
LXXVII
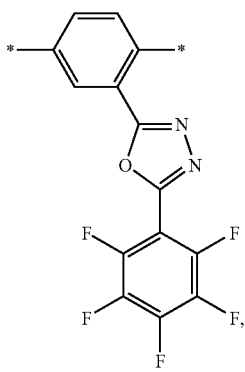
LXXX
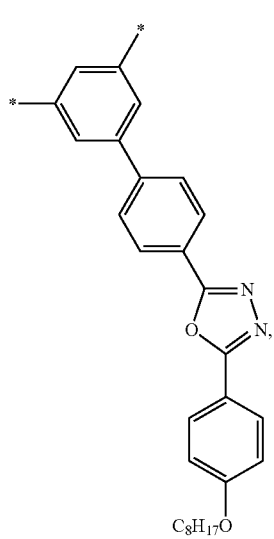
LXXVIII
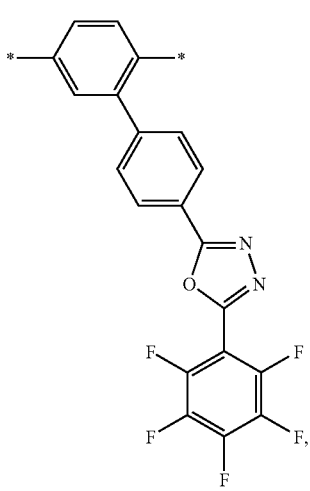
LXXXI
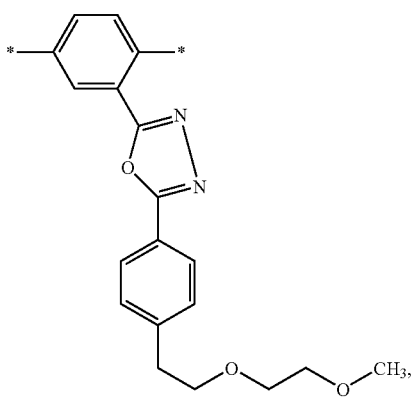
LXXIX
LXXXII -continued
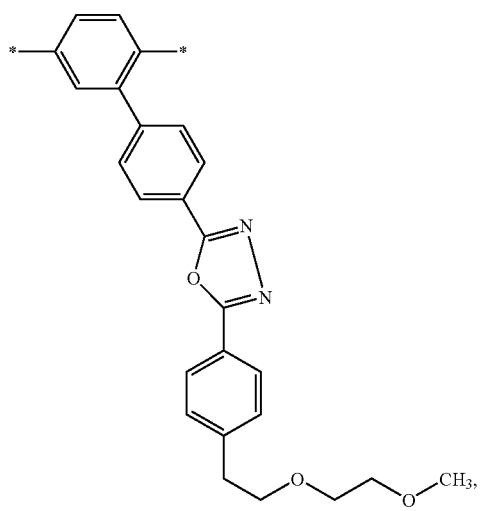
LXXXIII
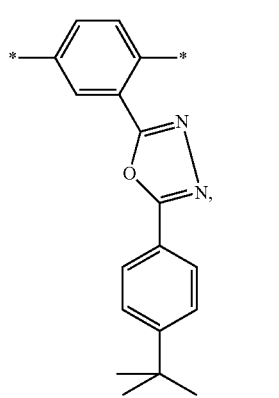
LXXXIV
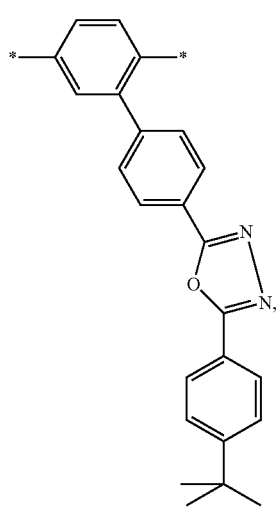
LXXXV
-continued
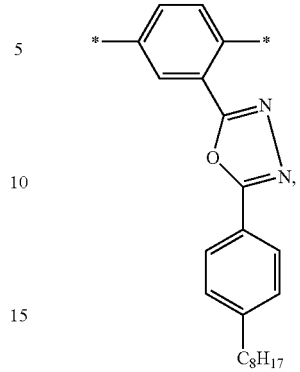
LXXXVI
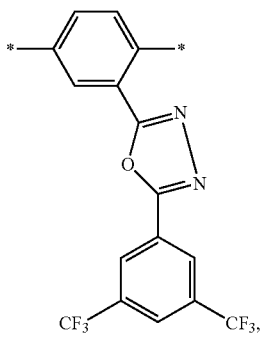
LXXXVII
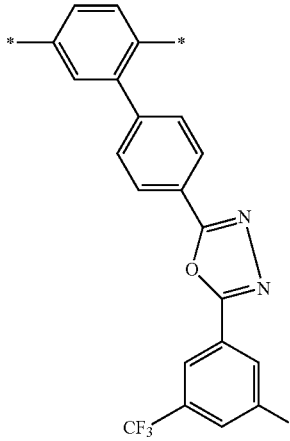
LXXXVIII
LXXXIX

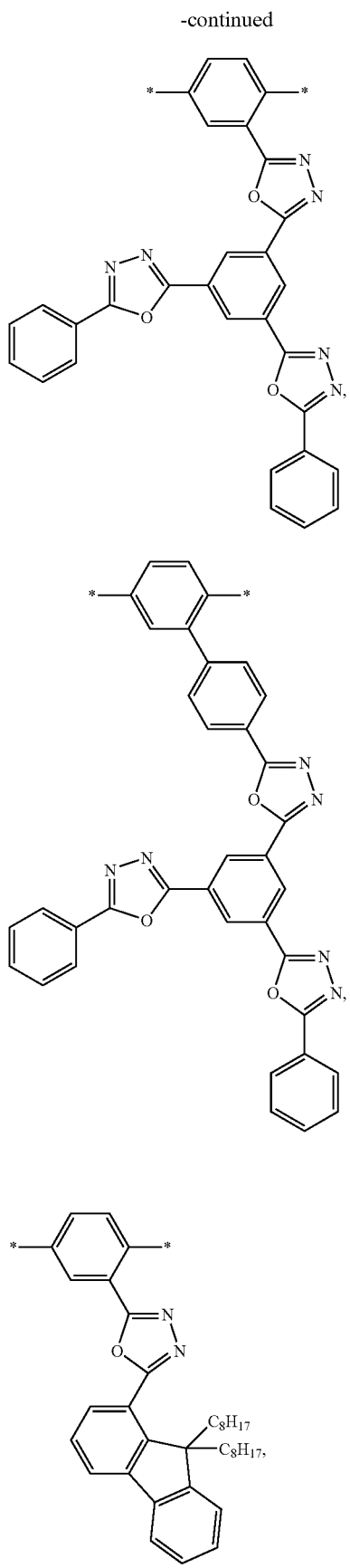
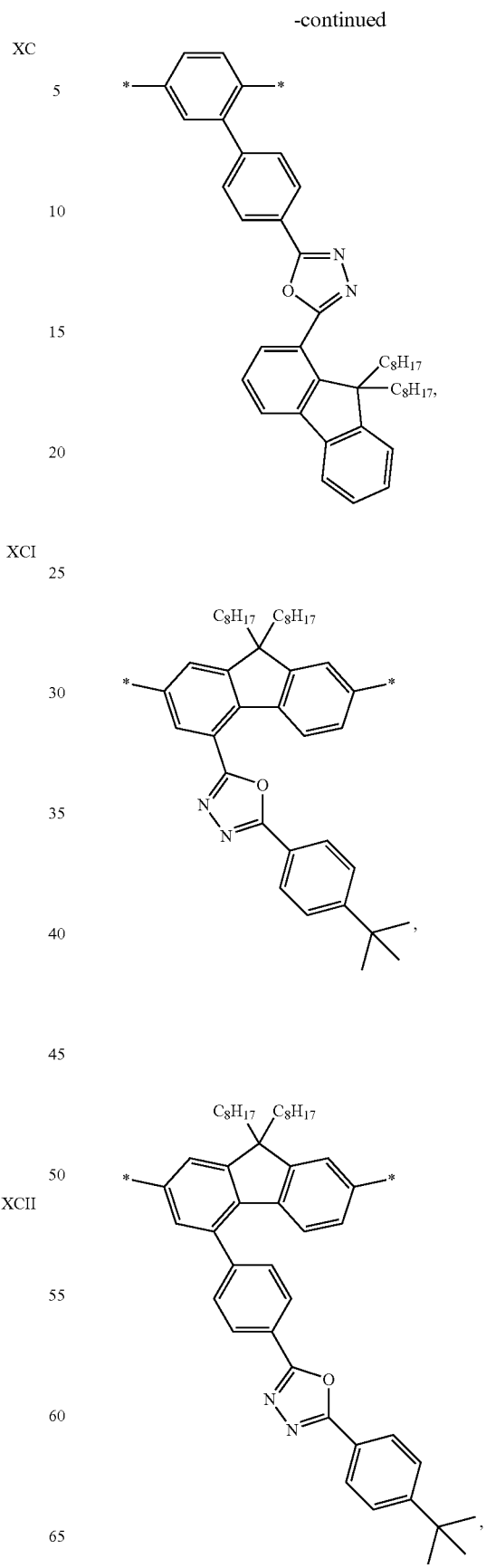

-continued
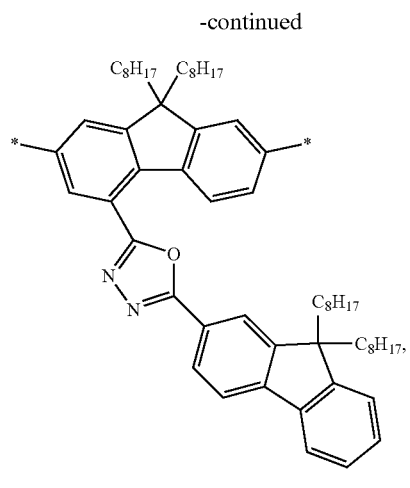
XCVI
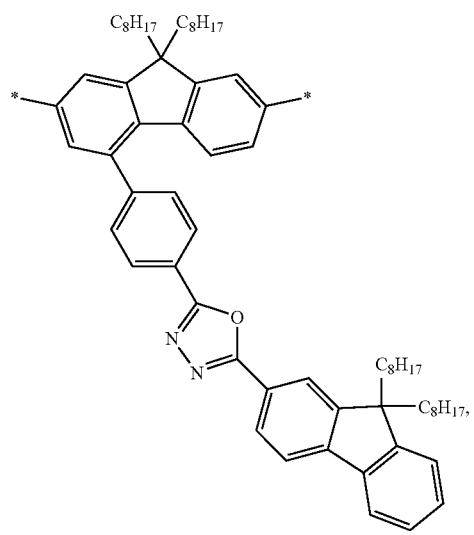
XCVII
XCVIII
XCIX
C
CI
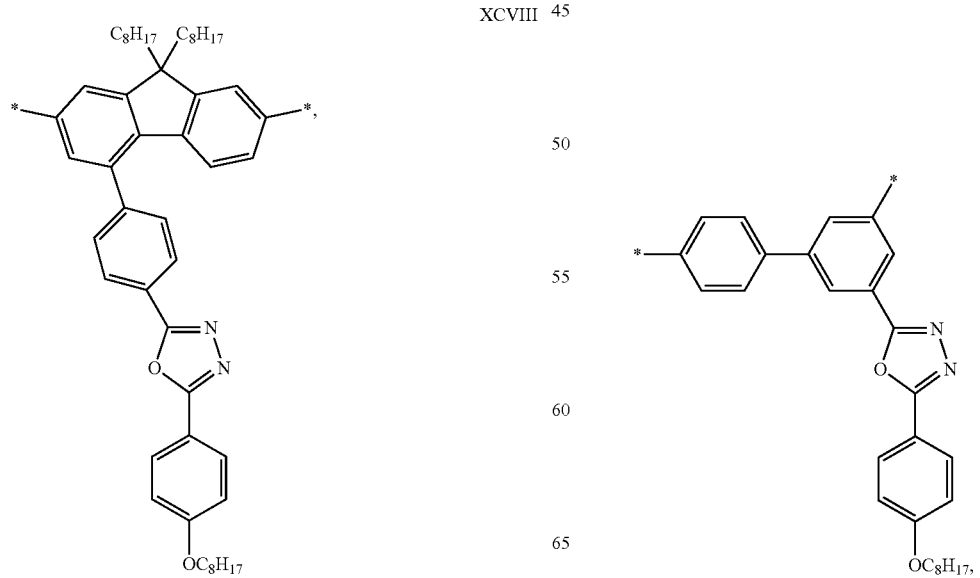

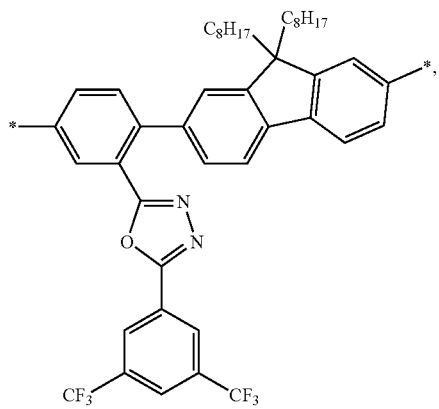

or the like.

The end capping (EC) groups in Formula I are each independently selected from a carbocyclic aryl, heteroaryl, or tertiary amino aryl group that is unsubstituted or substituted with one or more groups selected from alkyl, alkenyl, alkoxy, aryl, aryloxy, fluoro, fluoroalkyl, perfluoroalkyl, heteroalkyl, heteroaryl, and combinations thereof. The end capping groups are typically a $C_{6-40}$ carbocyclic aryl, $C_{3-40}$ heteroaryl, or $C_{12-60}$ tertiary aromatic amino aryl that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof.

The number of carbon atoms specified for the end capping group does not include the carbon atoms that may be present in a substituent group. For example, an end capping group that is a phenyl substituted with an butyl group would be considered to be a six carbon carbocyclic aryl. Thus, a carbocyclic aryl end capping group could have more than 40 carbon atoms in total. Likewise, a heteroaryl end capping group could have more than 40 carbon atoms in total and a tertiary aromatic amino aryl end capping group could have more than 60 carbon atoms in total.

No more than one end capping group is of Formula II or Formula III. In some embodiments, neither end capping group is of Formula II or Formula III. The end capping groups are both conjugated to the aromatic core. The bond between each end capping group and the aromatic core is typically a single carbon-carbon bond linking an aromatic ring of the aromatic core with an aromatic ring of each end capping group.

Suitable $C_{6-40}$ carbocyclic aryl end capping groups include, but are not limited to, a phenyl, biphenyl, terphenyl, anthryl, naphthyl, acenaphthyl, phenanthryl, dihydrophenathrenyl, anthracenyl, fluorenyl, 9-silafluorenyl, tetrahydropyrenyl, perylenyl, spirobisfluorenyl, fluoranthenyl, pyrenyl, dihydropyrenyl, tetrahydropyrenyl, rubrenyl, chrysenyl, or benzo[g,h,i]perylenyl that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof.

Suitable end $C_{3-40}$ heteroaryl capping groups include, but are not limited to, a furanyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, carbazoyl, benzoxazolyl, benzothiazolyl, benzimidazolyl, cinnolinyl, quinazolinyl, quinoxalinyl, phthalazinyl, benzothiadiazolyl, benzotriazinyl, phenazinyl, phenanthridinyl, acridinyl, indazolyl, or siloles that is unsubstituted or substituted with one or more groups selected from $C_{1\text{-}20}$ alkyl, $C_{2\text{-}20}$ alkenyl, $C_{1\text{-}20}$ alkoxy, $C_{6\text{-}20}$ aryl, $C_{6\text{-}20}$ aryloxy, fluoro, $C_{1\text{-}20}$ fluoroalkyl, $C_{1\text{-}20}$ perfluoroalkyl, $C_{1\text{-}20}$ heteroalkyl, $C_{3\text{-}20}$ heteroaryl, and combinations thereof.

Suitable $C_{12\text{-}60}$ tertiary aromatic amino aryl end capping groups include, but are not limited to, a monovalent radical of diarylaniline, alkyl carbazole, aryl carbazole, tetraaryldiamine, startburst amines, peraryltriamine, dendridic amines, spiroamines, and the like that is unsubstituted or substituted with one or more groups selected from $C_{1\text{-}20}$ alkyl, $C_{2\text{-}20}$ alkenyl, $C_{1\text{-}20}$ alkoxy, $C_{6\text{-}20}$ aryl, $C_{6\text{-}20}$ aryloxy, fluoro, $C_{1\text{-}20}$ fluoroalkyl, $C_{1\text{-}20}$ perfluoroalkyl, $C_{1\text{-}20}$ heteroalkyl, $C_{3\text{-}20}$ heteroaryl, and combinations thereof. For example, the tertiary aromatic amino aryl groups can be monovalent radicals of N,N,N'N'-tetraarylbenzidine, N,N,N',N'-tetraaryl-1,4-phenylenediamine, N,N,N'N'-tetraaryl-2,7-diaminofluorene, N,N'-bis(3-methylphenyl)-N,N'-bis(phenyl)benzidine, N,N'-bis(1-naphthyl)-N,N'-bis(phenyl)benzidine, 1,4-bis(carbazolyl)biphenyl, 4,4',4"-tris(N,N-diarylamino)triphenylamine, 1,3,5-tris(4-diarylaminophenyl)benzene, 4,4',4"-tris(N,N-diphenylamino)triphenylamine, 4,4',4"-tris(N-3-methylphenyl-N-phenylamino)triphenylamine, 1,3,5-tris(4-diphenylaminophenyl)benzene, and the like.

In some embodiments of Formula I, the end capping groups can provide a high bandgap between the highest occupied molecular orbital (HOMO) and the lowest unoccupied molecular orbital (LUMO). As used herein, high bandgap refers to an energy difference between the HOMO and LUMO of at least 2.5 eV. In some embodiments, the energy difference is at least 3 eV. A high bandgap tends to make the compound suitable for use as a light emitting molecule.

Some carbocyclic aryl end capping groups (e.g., phenylene group aryls, naphthalene group aryls, and condensed polycyclic aryls) can provide an electron affinity for the highest occupied molecular orbital (HOMO) and an ionization potential for the lowest unoccupied molecular orbital (LUMO) that are well matched to the aromatic core. This energy match and a large bandgap between the HOMO and LUMO are particularly advantageous when a high bandgap molecule is desired for use as an electron transport agent, as a hole blocker, as a molecular host for molecular or polymeric blue emitters, or as a blue emitting electroluminescent molecule. In addition, some carbocyclic aryl end capping groups can be sufficiently sterically hindering to reduce the formation of intermolecular or intramolecular configurations that produce excimer or exciplex emission that can cause color shifting of the electroluminescence.

Some end capping group can function to transport holes or block the transport of electrons. Such end capping groups can include, for example, heteroaryl groups that are electron rich and tertiary aromatic amino aryl groups. The use of such end capping groups can balance the hole and electron transport efficiencies, or tune the ionization potential and/or electron affinity of the compounds of the invention. Such end capping groups can enhance or modify the band gap and/or electroluminescent character of the compound. The end capping groups can be used, for example, to tune the color of the emitting light of the compound or other compounds in a composition. Certain heteroaryl and tertiary aromatic amino aryl end capping groups can provide compounds that have emissions in the red, green, or blue regions of the visible spectrum.

Condensed polycyclic arylenes in combination with heteroarylenes having —C=N— units can be included in the end capping groups to provide, in some compounds, centers for exciton recombination and emission. In some compounds, the introduction of condensed polycyclic arylene or aryl groups in combination with a heteroarylene or heteroaryl group that has a —C=N— unit can provide color tuning. For example, the condensed polycyclic arylenes or aryls derived from anthracene, perylene, and pyrene can be combined with an adjacent heteroarylene or heteroaryl derived from benzothiadiazole.

In other embodiments, the end capping groups can function to transport electrons or block the transport of holes. Such end capping groups can include; for example, a radical of heterocyclic compound having a —C=N— units such as, for example, radicals of oxadiazoles, N-substituted-triazoles, N-substituted imidazoles, N-substituted pyrazoles, oxazoles, isoxazole, thiazoles, isothiazoles, pyridines, pyridazines, pyrimidines, pyrazines, triazines, tetrazenes, benzoxazoles, benzothiazoles, benzothiadiazoles, quinolines, isoquinolines, cinnolines, quinazolines, quinoxalines, phthalazines, benzotriazines, phenazines, phenanthridines, acridines, and the like.

In some compounds of Formula I, both end capping groups are independently selected from a monovalent radical of

CVI

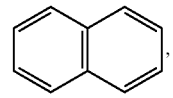

CVII

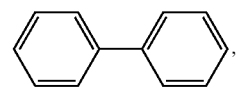

CVIII

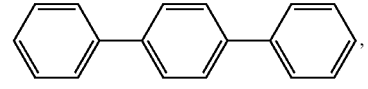

CIX

CX

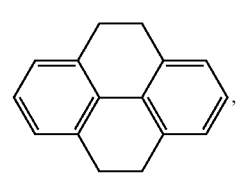

CXI

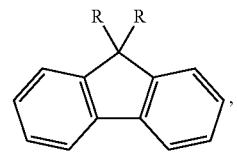

CXII

-continued
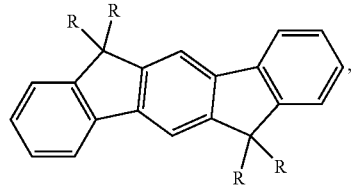
CXIII
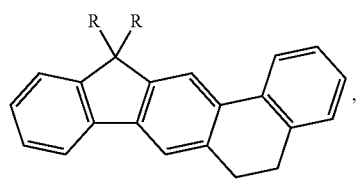
CXIV
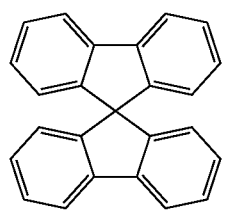
CXV
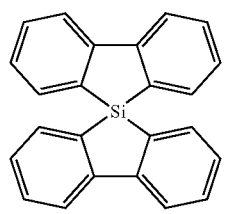
CXVI
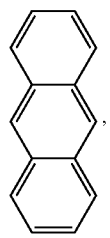
CXVII
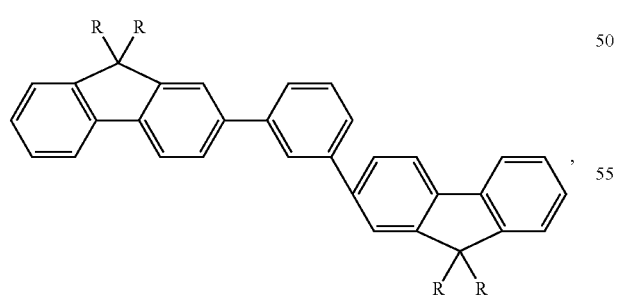
CXVIII
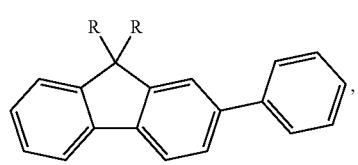
CXIX
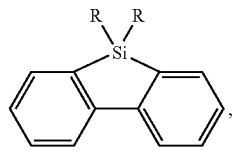
CXX
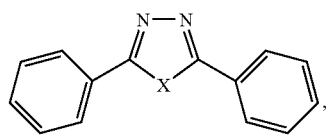
CXXI
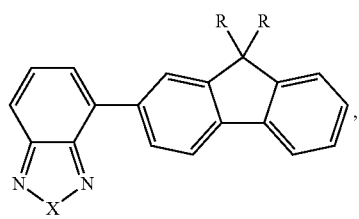
CXXII
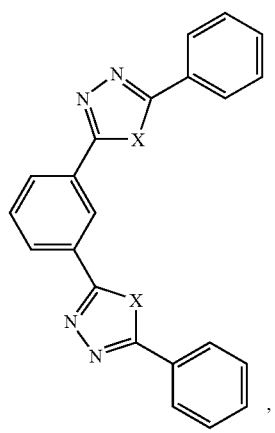
CXXIII
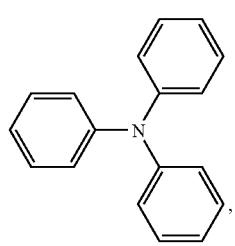
CXXIV
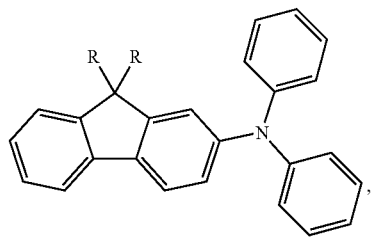
CXXV

CXXVI

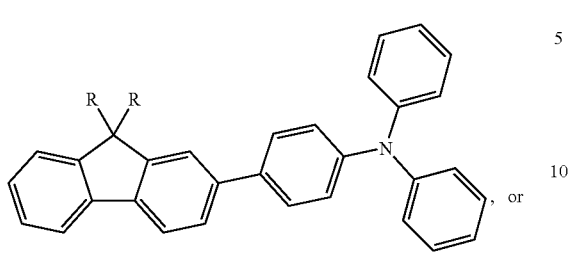

, or

CXXVII

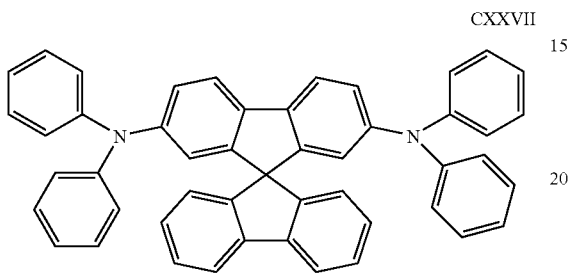

that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently selected from $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl, $C_{1-30}$ heteroalkyl, and combinations thereof. Each X is independently O, S, or $NR^1$, where $R^1$ is a $C_{1-30}$ alkyl, $C_{6-20}$ aryl, $C_{3-30}$ heteroaryl, $C_{1-30}$ heteroalkyl, or combinations thereof.

In some embodiments of an end capping group, a carbocyclic arylene group is conjugated to the groups of Formula CVI to CXXVII. The carbocyclic arylene group is between the aromatic core and the groups of Formula CVI to CXXVII. For example, group of Formula CVI to CXXVII can be conjugated to a divalent radical of

CXXVIII

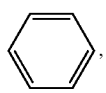

,

CXXIX

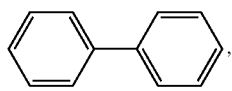

,

CXXX

,

CXXXI

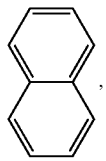

,

CXXXII

,

CXXXIII

,

CXXXIV

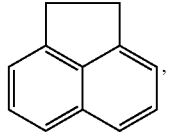

,

CXXXV

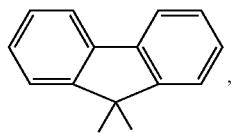

,

CXXXVI

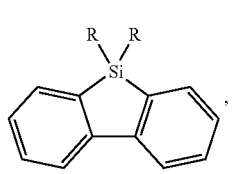

,

CXXXVII

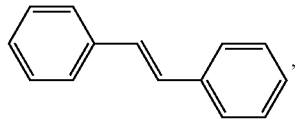

,

CXXXVIII

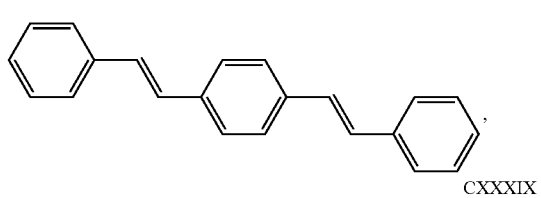

,

CXXXIX

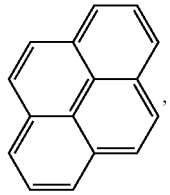

,

CXL

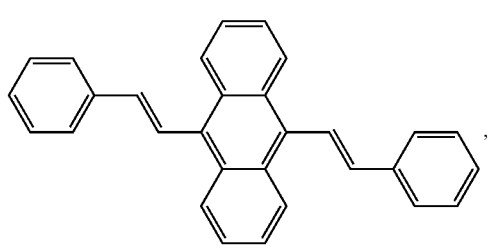

,

-continued
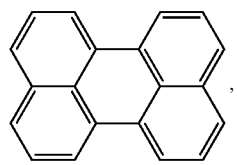
CXLI
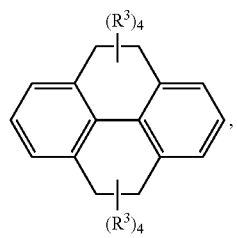
CXLII
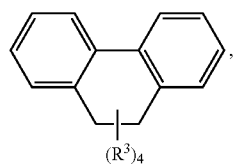
CXLIII
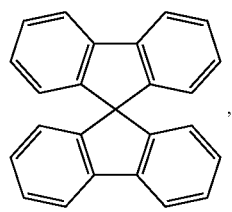
CXLIV
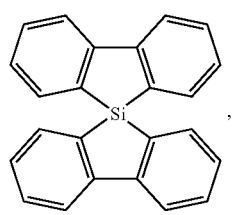
CXLV
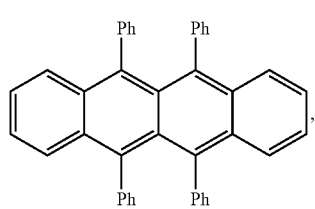
CXLVI
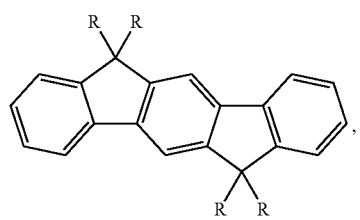
CXLVII
-continued
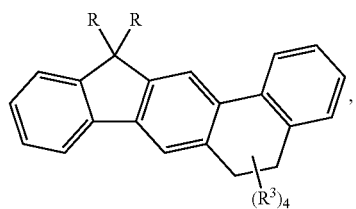
CXLVIII
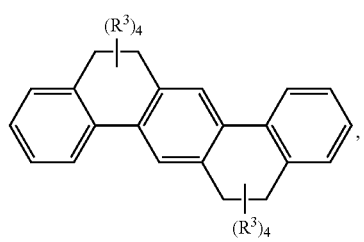
CXLIX
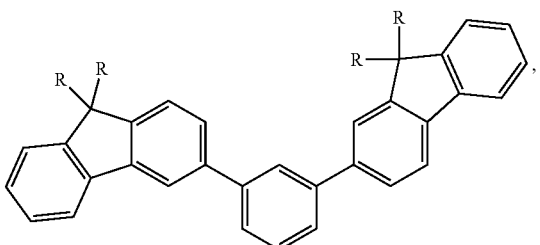
CL
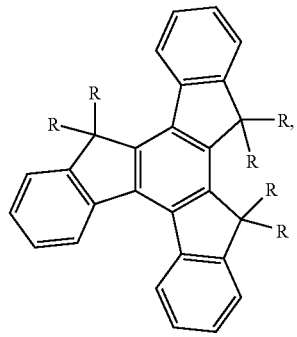
CLI
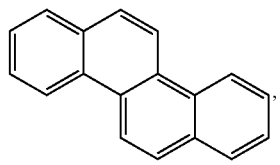
CLII

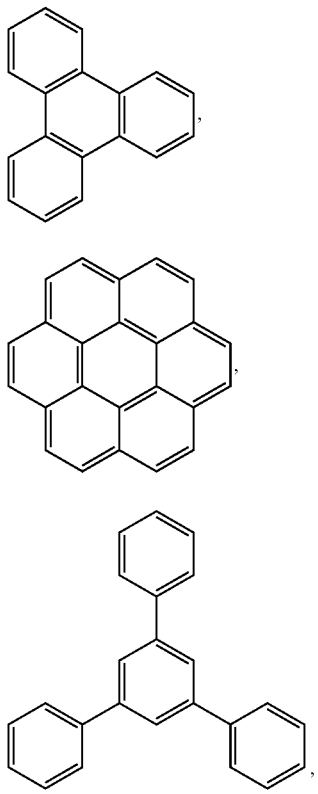

or the like that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. In these formulas, the symbol Ph refer to a phenyl ring. Each R is independently selected from $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl, $C_{1-30}$ heteroalkyl, and combinations thereof. Each $R^3$ is independently selected from hydrogen, $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl, $C_{1-30}$ heteroalkyl, and combinations thereof.

In other embodiments of a monovalent end capping group, a group according to Formula CVI to CXXVII can be conjugated to a group having a —C=N— unit. The group having the —C=N— unit is between the aromatic core and the group of Formula CVI to CXXVII. For example, a group of Formula CVI to CXXVII can be conjugated to a divalent radical of

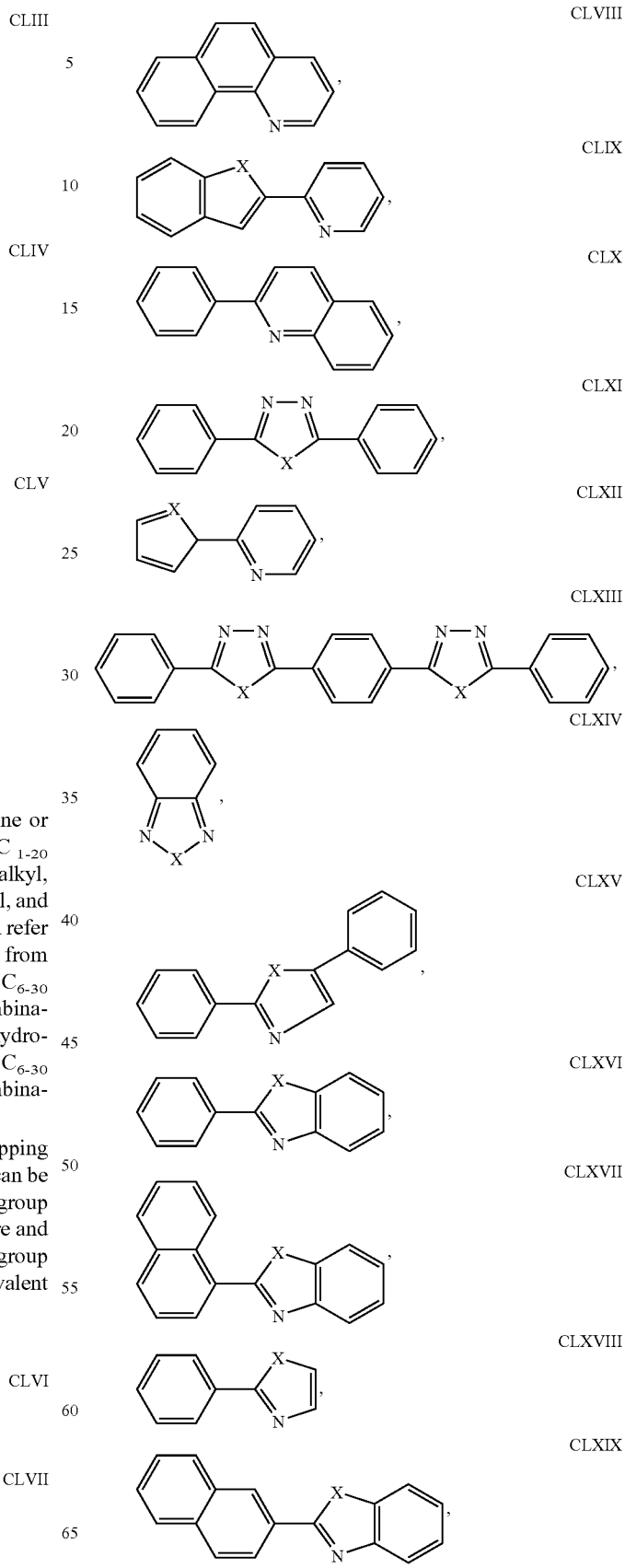

-continued

CLXX
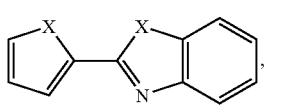

CLXXI

CLXXII
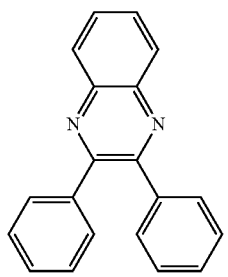

CLXXIII
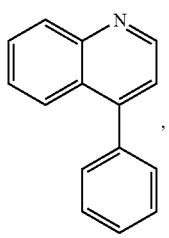

CLXXIV
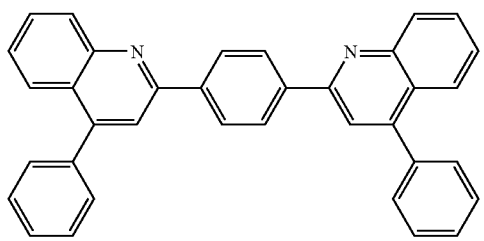

CLXXV
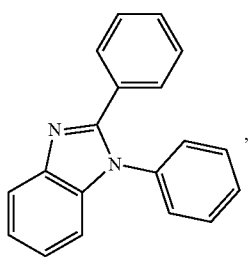

or the like that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each X is independently O, S, or $NR^1$, where $R^1$ is a $C_{1-30}$ alkyl, $C_{6-20}$ aryl, $C_{3-30}$ heteroaryl, $C_{1-30}$ heteroalkyl, or combinations thereof.

In yet other embodiments of a monovalent end capping group, a group according to Formula CVI to CXXVII can be conjugated to a heteroarylene that is electron rich or to a tertiary aromatic amino arylene. The heteroarylene or tertiary aromatic arylene is positioned between the aromatic core and a group of Formula CVI to CXXVII. For example, a group of Formula CVI to CXXVII can be conjugated to a radical of CLXXVI
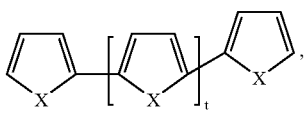

CLXXVII
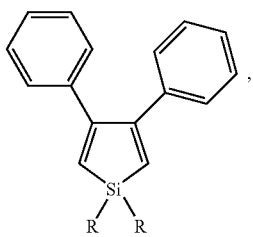

CLXXVIII
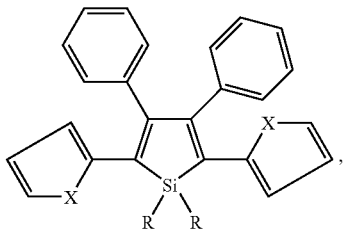

CLXXIX
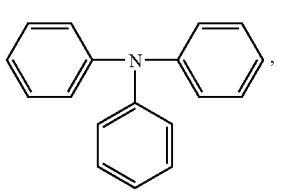

CLXXX
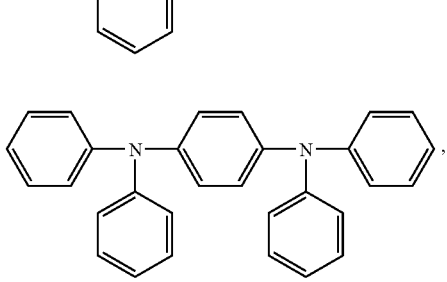

CLXXXI
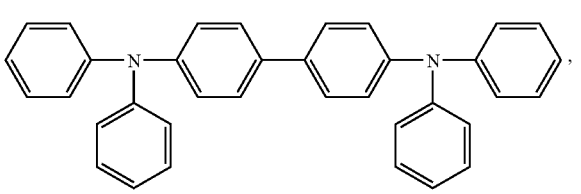

CLXXXII
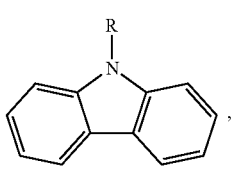

-continued

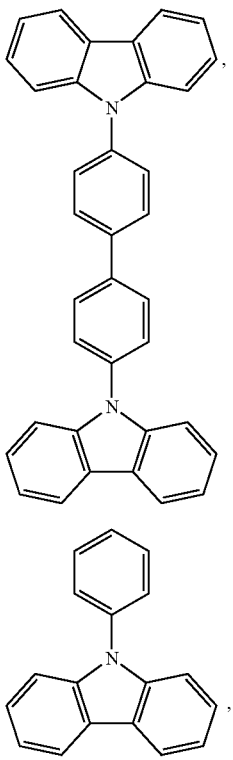
CLXXXIII

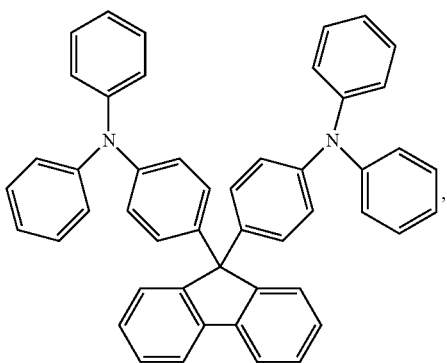
CLXXXIV

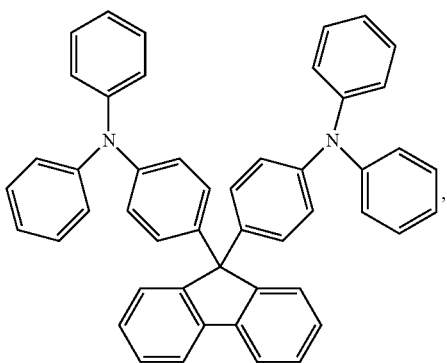
CLXXXV or the like that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently selected from $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl, $C_{1-30}$ heteroalkyl, and combinations thereof. Each X is independently O, S, or $NR^1$, where $R^1$ is a $C_{1-30}$ alkyl, $C_{6-20}$ aryl, $C_{3-30}$ heteroaryl, $C_{1-30}$ heteroalkyl, or combinations thereof. Each t is an integer equal to 0 to 4.

When a group of Formula CVI to CXXVII is combined with another group to form the end capping group, no order of synthesis or method of synthesis is implied to prepare the compound of Formula I. The second group (e.g., a group of Formula CXXVIII to CLXXXV) can be attached to the aromatic core before attachment to the group of Formula CVI to CXCVII or the second group can be attached to the rest of the end capping group (e.g., a group of Formula CVI to CXXVII) before attachment to the aromatic core.

Any group R or $R^3$ on an end capping group can include a divalent poly(oxyalkylene) soft segment of Formula VI $$*-O(C_mH_{2m}O)_y-* \qquad \text{VI}$$

or a divalent poly(dialkylsiloxane) soft segment of Formula VII $$*-[-Si(C_wH_{2w+1})_2O-]_y-* \qquad \text{VII}$$

where m is an integer of 1 to 6, y is an integer of 2 to 20, and w is an integer of 1 to 10. In some embodiments, the poly(oxyalkylene) or poly(dialkylsiloxane) soft segments can be connected to an alkyl, aryl, or heteroaryl group. The substituent can, for example, have the Formula VIII $$*-[-Ar-]_v-SS-R'' \qquad \text{VIII}$$

where SS is a poly(oxyalkylene) or poly(dialkylsiloxane) soft segment, Ar is an arylene group, v is an integer of 0 or 1, and R" is an aryl, heteroaryl, or a alkyl. In some examples, R" is a sterically hindered group. Groups such as those included in Formula VIII can reduce the formation of intermolecular or intramolecular configurations that produce undesirable excimer or exciplex emission.

In some methods of preparing organic electroluminescent devices, a compound of the invention is thermally transferred from a donor substrate to a receptor substrate. Compounds having, for example, a poly(oxyalkylene) or poly(dialkylsiloxane) soft segment can provide suitable solubility parameter matching to a receptor substrate. In addition or alternatively, these soft segments can alter other properties useful to thermal transfer and film stability such as, for example, molecular weight, melting temperature, glass transition temperature, percent crystallinity and tendency to crystallize or form aggregates, viscosity, thin film morphology, rheological properties such as melt viscosity and relaxation time, excimer and exciplex formation, cohesive strength, and light emission frequency, if desired. The poly(oxyalkylene) groups or poly(dialkylsiloxane) soft segments can, in some compounds, improve thermal transfer and adhesion of the molecular film or blend to commercially available conducting ionic polymers such as PEDT and PANI, which are commonly used as anode buffer layers in organic electroluminescent device constructions.

In some compounds, the end capping groups can be substituted with one or more groups selected from fluoro, $C_{1-20}$ fluoroalkyls, $C_{1-20}$ perfluoroalkyls, and combinations thereof. These substituents can lower the vapor pressure of the compounds and make them more suitable for vapor deposition. These substituents can improve the solubility and film forming properties of the compounds. These substituents can, in some compounds, increase the ionization potential and electron affinity, thereby making it easier for the compounds to inject electrons and block holes.

The two end capping groups can be the same or different. In some embodiments of Formula I, both of the end capping groups (EC) are identical. In other embodiments, end capping groups have the same basic structure but substituents present on one end capping group can be absent on the other. In yet other embodiments, the two end capping groups have the same basic structure and each end capping group has the same type of substituent (e.g., alkyl, alkenyl, alkoxy, aryl, fluoro, fluoroalkyl, perfluoroalkyl, heteroalkyl, heteroaryl, or combinations thereof) but the substituents contain a different number of carbon atoms.

In some embodiments, both of the end capping groups are selected from
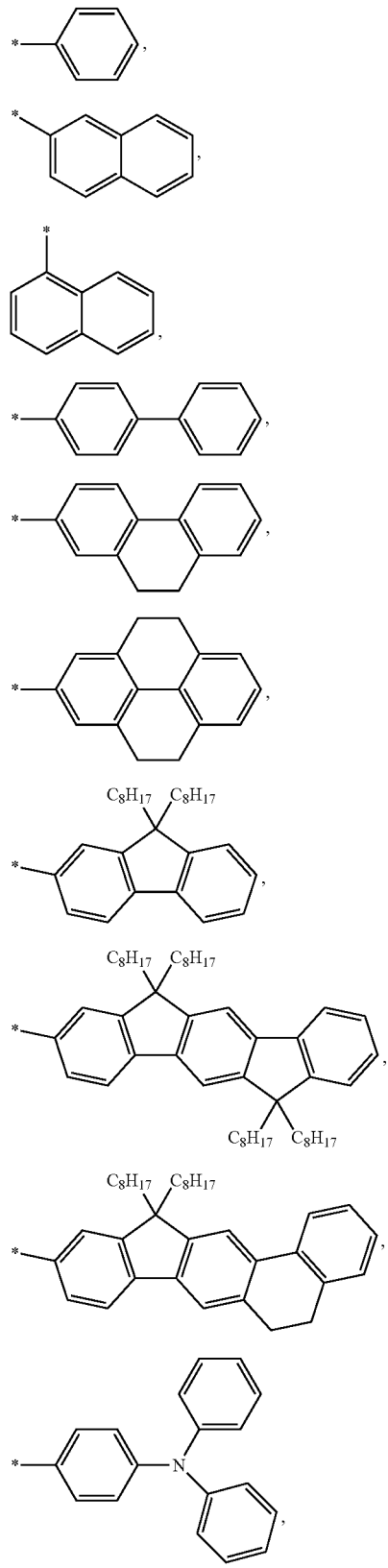
CLXXXVI, CLXXXVII, CLXXXVIII, CLXXXIX, CXC, CXCI, CXCII, CXCIII, CXCIV, CXCV
-continued
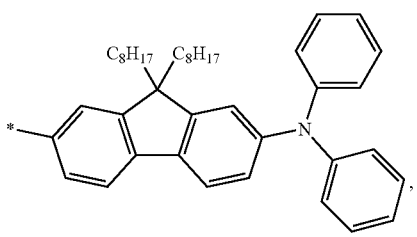
CXCVI
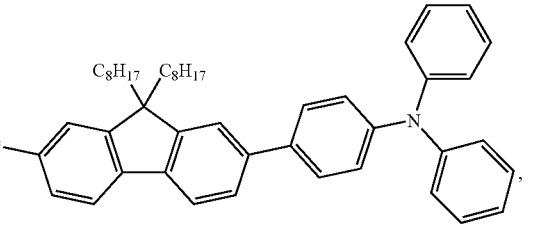
CXCVII
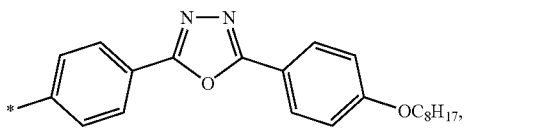
CXCVIII
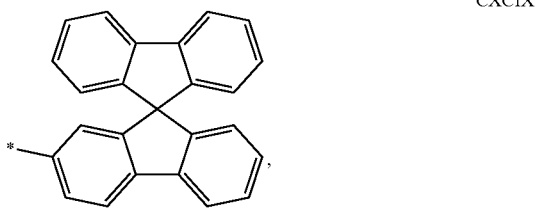
CXCIX
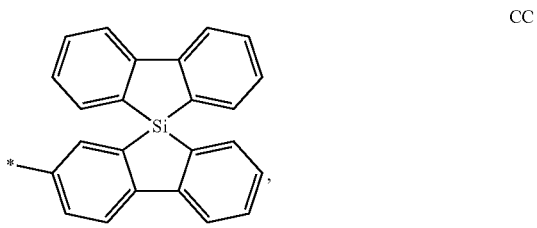
CC
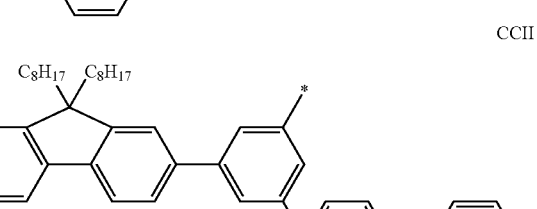
CCI
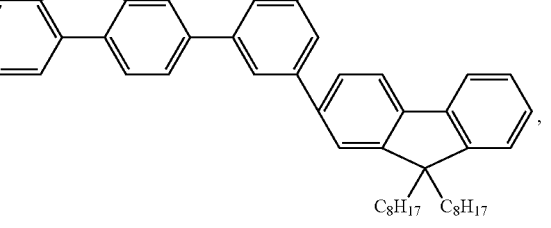
CCII -continued
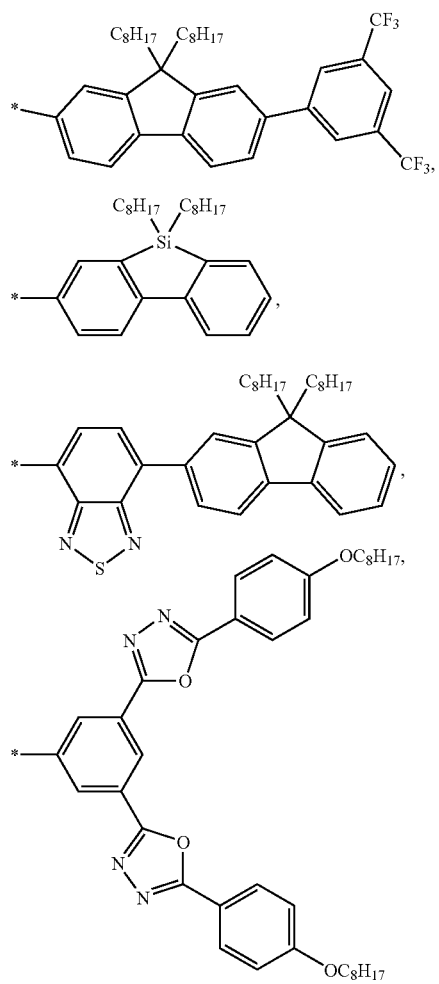
CCIII
CCIV
CCV
CCVI
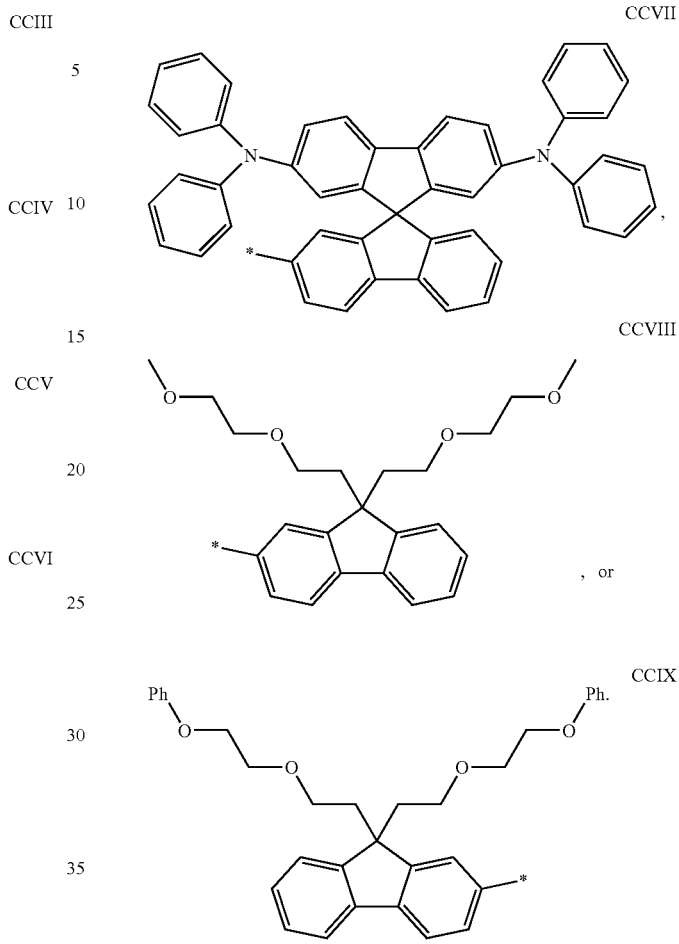
CCVII
CCVIII
, or
CCIX
Specific examples of compounds according to Formula I include, but are not limited to,
CCX
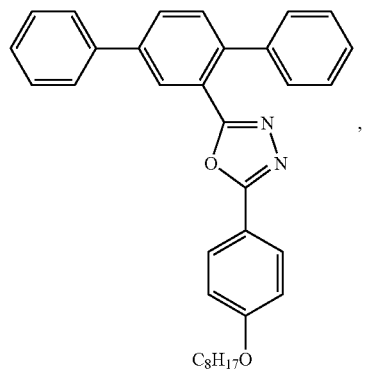
CCXI
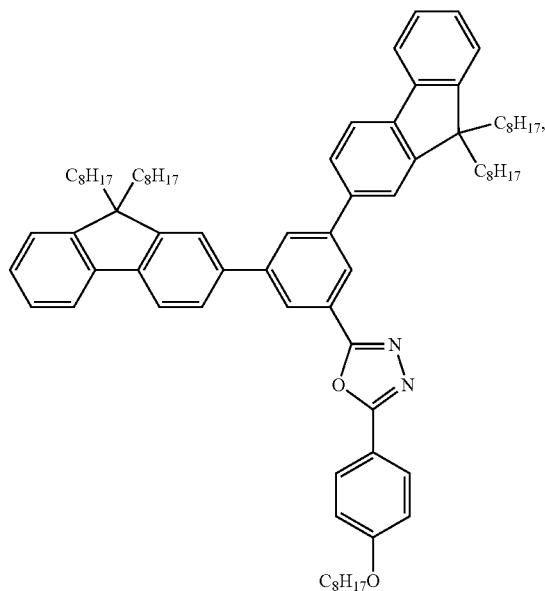

-continued
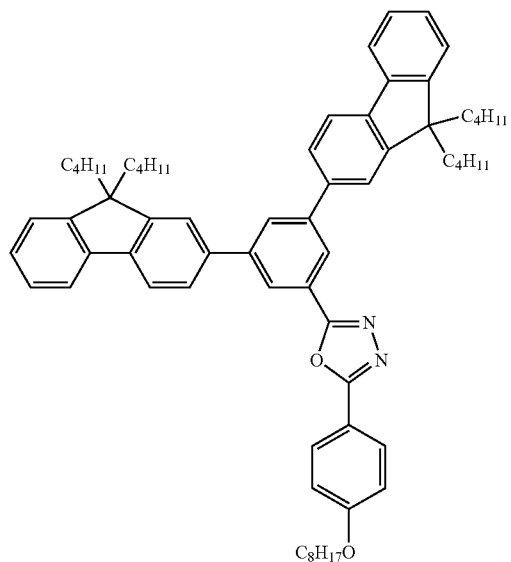
CCXII
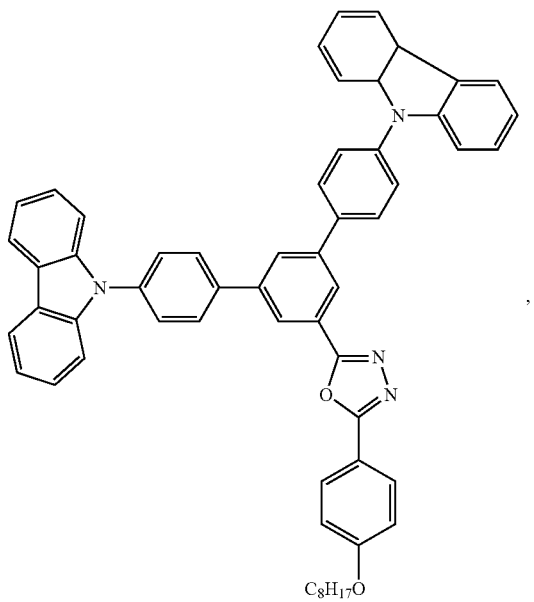
CCXIII
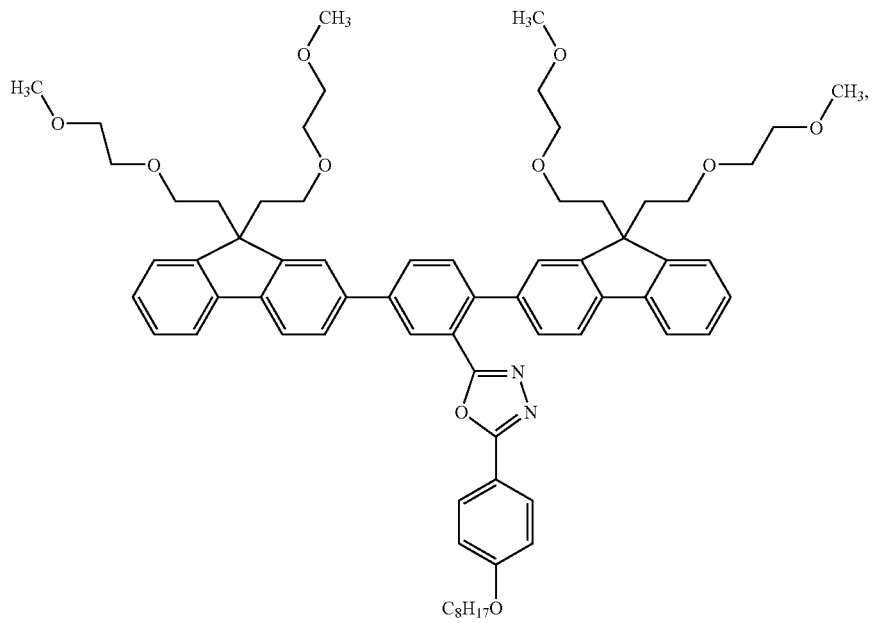
CCXIV

-continued
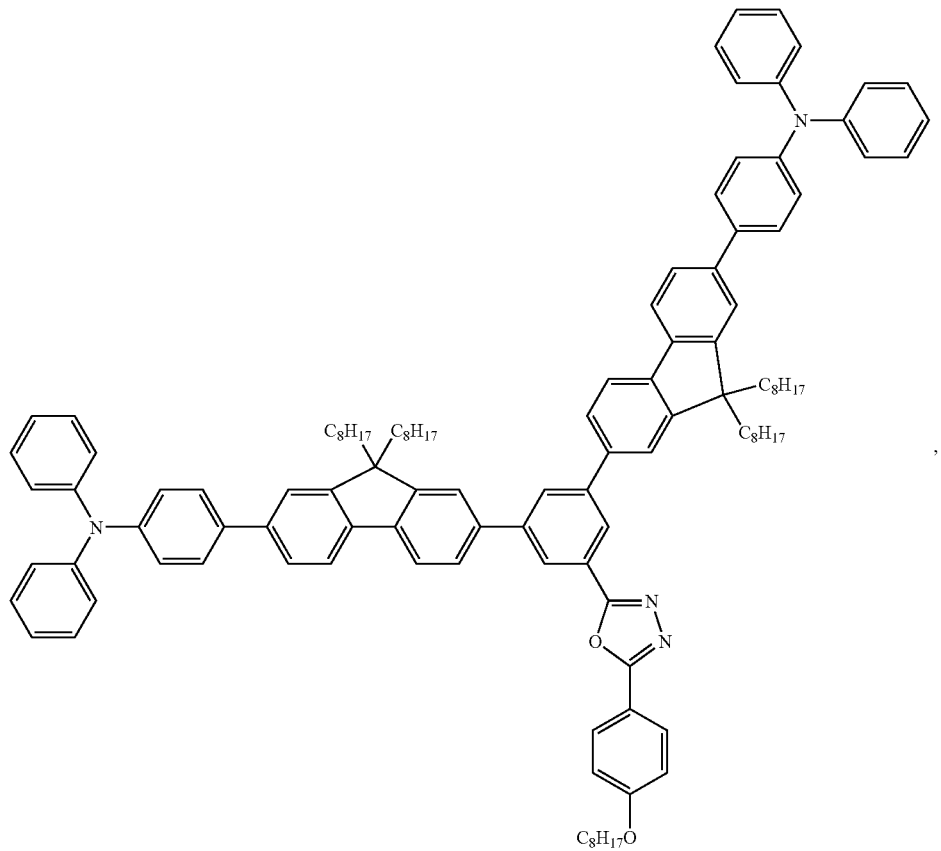
CCXV
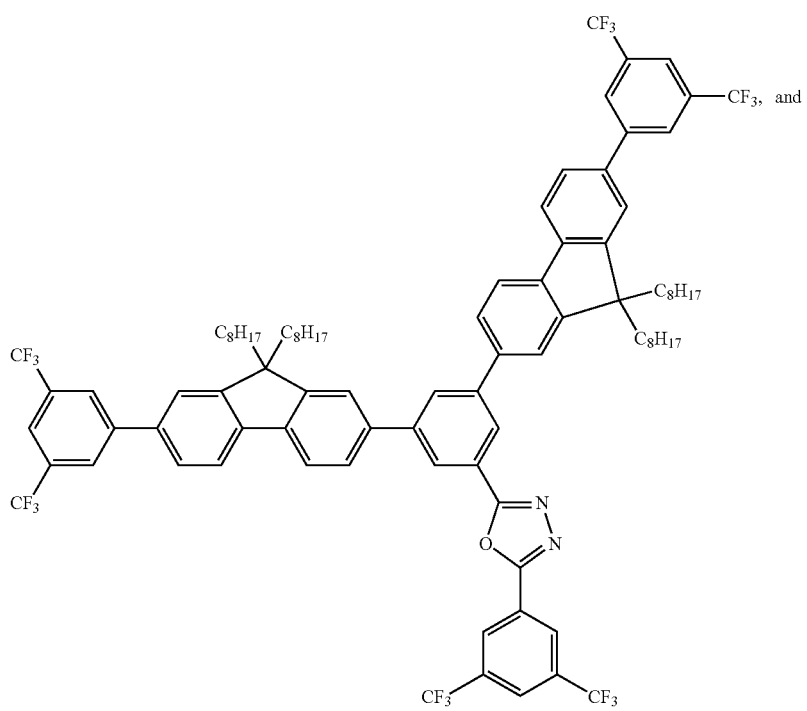
CCXVI, and

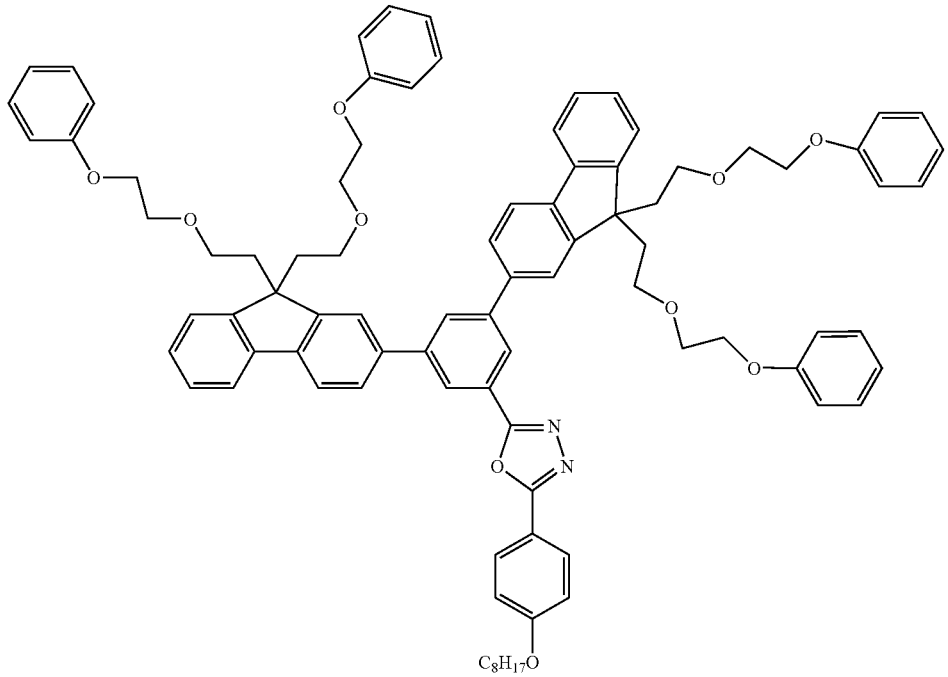

CCXVII

Compounds of Formula I can be prepared by any method known in the art. In some embodiments, the compounds are prepared by reacting a dibromide or dichloride intermediate of the aromatic core with a boronic acid or boronic ester intermediate of the end capping group under palladium catalyzed conditions using Suzuki coupling methods as taught by Miyaura et al., *Chemical Reviews*, 95, 2457-2483 (1995), herein incorporated by reference in its entirety.

The compounds of Formula I can also be prepared by reacting aryl dibromides or iodides with aryl Grignard reagents (see Widdowson, D. A., Zhang, Y., *Tetrahedron*, 42, 2111 (1986)) with aryltin compound (see Bailey, T. R., *Tetrahedron Lett.*, 27, 4407 (1986), herein incorporated by reference) and with arylmercury compounds (see Bumagin, N. A., More, P. G., Beletskaya, I. P., *J. Organomet. Chem.*, 364, 231 (1986), herein incorporated by reference). Aryl sulfone can be coupled with aryl Grignard reagents in the presence of a nickel catalyst (see Clayden, J., Cooney, J. J. A., Julia, M., *J. Chem. Soc., Perkin Trans.*, 1, 7 (1995), herein incorporated by reference). In some embodiment, EC can be coupled to the aromatic core one at a time. In some embodiments, the aromatic core can be coupled to part of the end capping group, and then the rest part of end capping group can be added in subsequent steps.

Diahalogenated intermediates of the aromatic core include the following:

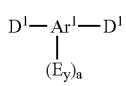

CCXL

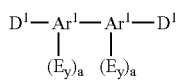

CCXLI where $D^1$ is a bromide or chloride and $Ar_1\text{-}(E_y)_a$ is as previously defined.

Dihalogenated 1,3,4-oxadiazole of Formula CCLII can be synthesized by the acylation of substituted tetrazoles as shown in Reaction Scheme I. A dihaloaroyl chloride of Formula CCL is reacted with a substituted tetrazole of Formula CCLI with heating for about 12 hours in an inert solvent such as pyridine (Myznikov et al., *J. Gen. Chem. USSR (Engl. Transl.)*, 62 (6), 1125-1128 (1992)) to form the dihalogenated oxadiazole intermediate of Formula CCLII. $D^1$ is a halogen and $R^z$ is an optional substituent selected from the group of alkyl, alkenyl, alkoxy, aryl, aryloxy, fluoro, fluoroalkyl, perfluoroalkyl, heteroalkyl, heteroaryl, alkyl oxadiazolyl, aryl oxadiazolyl, alkyl triazolyl, aryl triazolyl, diarylamino, aryldiarylamino, and combinations thereof. The tetrazole of Formula CCLI can be prepared by reaction of the corresponding nitrile with $NaN_3$ and $NH_4Cl$ in N,N-dimethylformamide (DMF) at reflux.

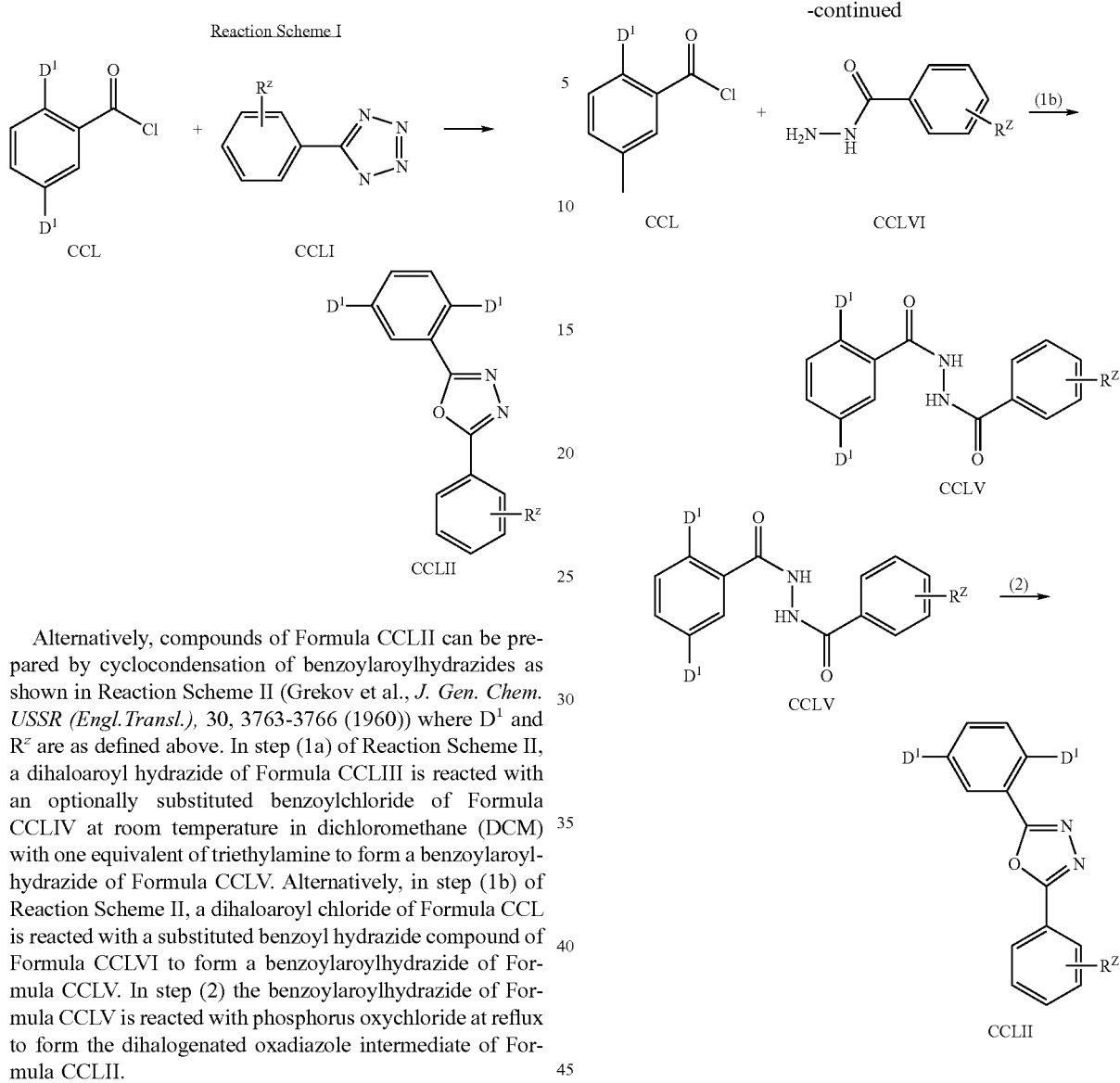

Alternatively, compounds of Formula CCLII can be prepared by cyclocondensation of benzoylaroylhydrazides as shown in Reaction Scheme II (Grekov et al., *J. Gen. Chem. USSR (Engl. Transl.)*, 30, 3763-3766 (1960)) where $D^1$ and $R^z$ are as defined above. In step (1a) of Reaction Scheme II, a dihaloaroyl hydrazide of Formula CCLIII is reacted with an optionally substituted benzoylchloride of Formula CCLIV at room temperature in dichloromethane (DCM) with one equivalent of triethylamine to form a benzoylaroylhydrazide of Formula CCLV. Alternatively, in step (1b) of Reaction Scheme II, a dihaloaroyl chloride of Formula CCL is reacted with a substituted benzoyl hydrazide compound of Formula CCLVI to form a benzoylaroylhydrazide of Formula CCLV. In step (2) the benzoylaroylhydrazide of Formula CCLV is reacted with phosphorus oxychloride at reflux to form the dihalogenated oxadiazole intermediate of Formula CCLII.

For example, electron transport intermediates 1, 2, 3, and 4 were made by condensation of the corresponding 2,5-dihalobenzoyl chloride with the appropriately substituted benzoyl hydrazide.

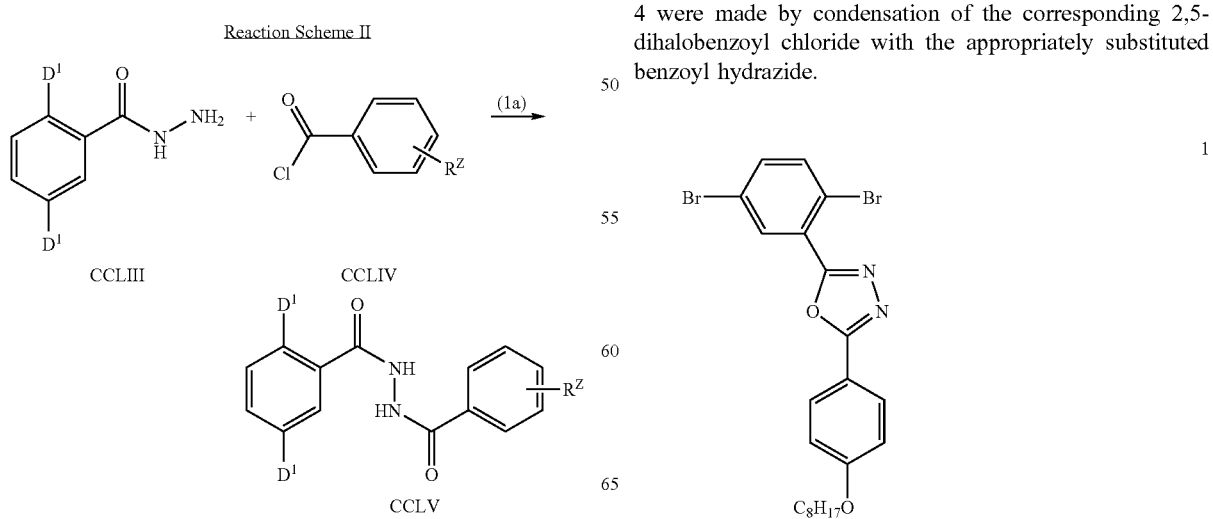

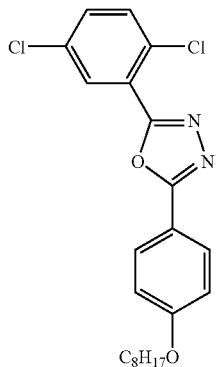

2

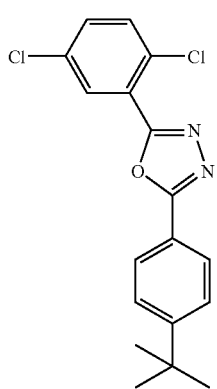

3

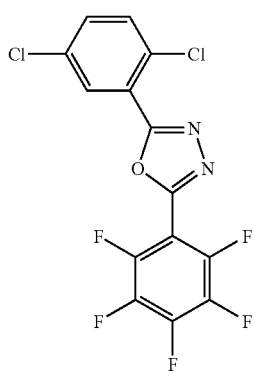

4

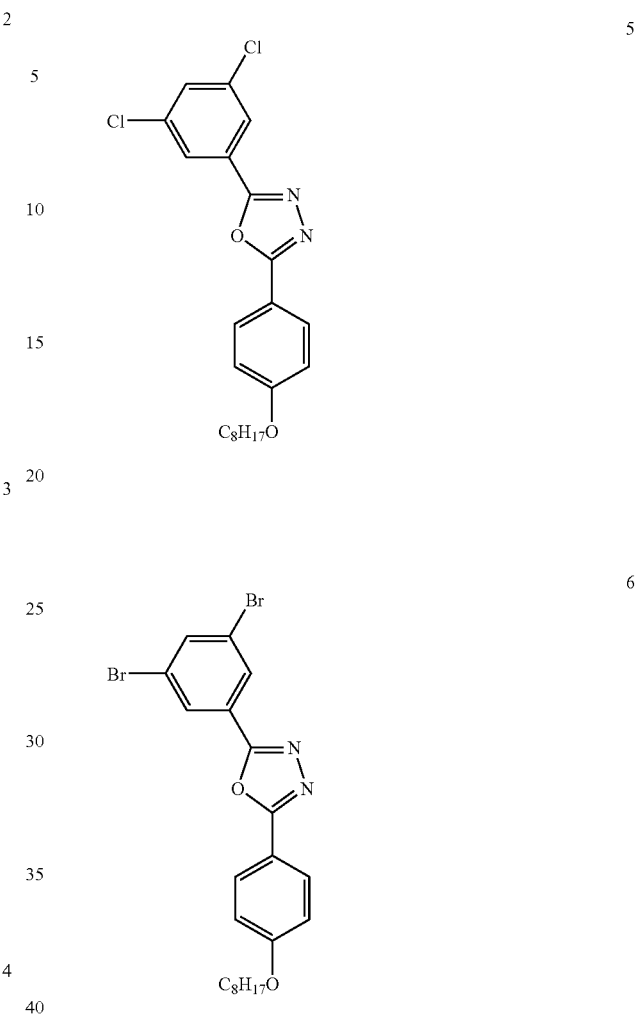

1,3-Dihalogenated intermediates are similarly prepared. For example, the electron transport intermediates 2-(3,5-dichlorophenyl)-5-[4-(octyloxy)phenyl]-1,3,4-oxadiazole (5 and 2-(3,5-dibromophenyl)-5-[4-(octyloxy)phenyl]-1,3,4-oxadiazole (6) were prepared by condensation of the corresponding 3,5-dihalobenzoyl chloride with 4-octyloxybenzoyl hydrazide, followed by cyclocondensation of the intermediate 3,5-dihalo-N'-[4-(octyloxy)benzoyl]-benzohydrazide. Monohalogenated 1,3,4-oxadiazole end capping group intermediates were similarly prepared from the corresponding monohalogenated precursors.

Dihalogenated 1,3,4-thiadiazole intermediates of Formula CCLVII can be prepared by cyclocondensation of the benzoylaroylhydrazide intermediates as shown in Reaction Scheme III (A. T. Prudchenko, *J. Gen. Chem. USSR (Engl. Transl.)*, 37, 2082-2084(1967)) where D' and RZ are as defined in Reaction Scheme I. In Reaction Scheme III the benzoylaroylhydrazide intermediate of Formula CCLV is reacted under metathesis conditions with $P_2S_5$ to provide the 1,3,4-thiadiazoles of Formula CCLVII.

Reaction Scheme III

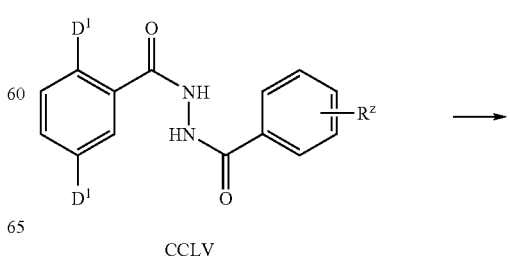

CCLV

-continued

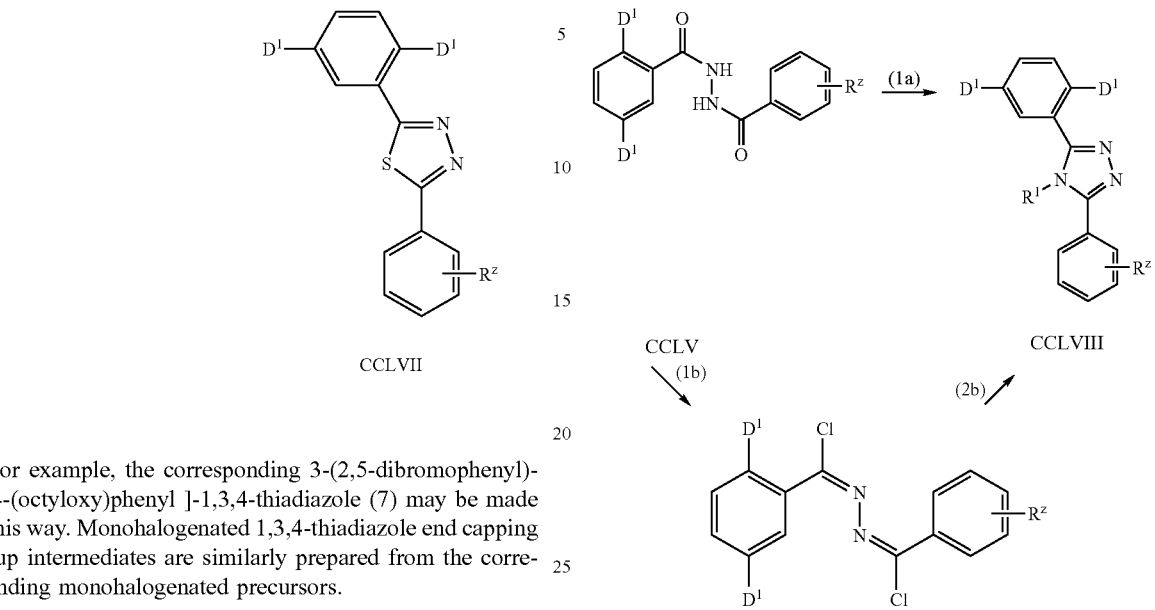

For example, the corresponding 3-(2,5-dibromophenyl)-5-[4-(octyloxy)phenyl ]-1,3,4-thiadiazole (7) may be made in this way. Monohalogenated 1,3,4-thiadiazole end capping group intermediates are similarly prepared from the corresponding monohalogenated precursors.

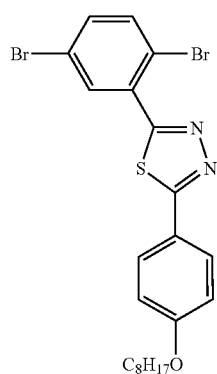

Dihalogenated 1,3,4-triazole intermediates of Formula CCLVIII can be prepared by cyclocondensation of the benzoylaroylhydrazide intermediates as shown in Reaction Scheme IV (E. Klingsberg, *J. Org. Chem.*, 23, 1086(1958)) where $D^1$ and $R^z$ are as defined in Reaction Scheme I, and $R^1$ is aryl, alkyl, heteroaryl, or heteroalkyl. In step (1a) of Reaction Scheme IV the benzoylaroylhydrazide intermediate of Formula CCLV is reacted with phosphorus trichloride at an elevated temperature, e.g., 150° C., in the presence of $R^1NH_2$, wherein $R^1$ is aryl or heteroaryl to provide the 1,3,4-triazole of Formula CCLVIII. Alternatively, in step (1b) of Reaction Scheme IV, the benzoylaroylhydrazide is reacted with chlorine in glacial acetic acid (Moss et al., *J. Chem. Soc. Perkin Trans.*, 1(9), 1999-2006 (1982)) or other non-reactive solvent to form the 1,4-dichloro-1,4-diphenyl compound of Formula CCLIX. In step (2b) of Reaction Scheme IV, the 1,4-dichloro-1,4-diphenyl compound of Formula CCLIX is reacted with $R'NH_2$ (Gautun et al., *Acta Chem. Scand.*, 45(6), 609-615 (1991)), wherein $R^1$ is alkyl or arylalkyl, to provide the corresponding 1,3,4-triazoles of Formula CCLVIII.

Reaction Scheme IV

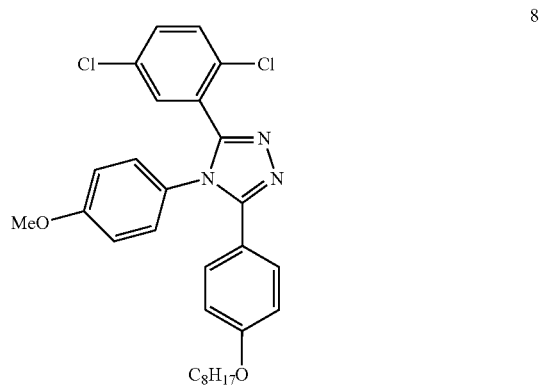

For example, the triazole derivative 3-(2,5-dichlorophenyl)-4-(4-methoxyphenyl)-5-[4-(octyloxy)phenyl ]-4H-1,2,4-triazole (8) was made by this method. Monohalogenated 1,3,4-triazole end capping group intermediates are similarly prepared from the corresponding monohalogenated precursors.

Dihalogenated 1,3,4-oxadiazole intermediates of Formula CCLX can be synthesized by Suzuki coupling of a monofunctional diaryloxadiazole with a monoboronic acid/ester of the dihaloarylene as shown in Reaction Scheme V. In Reaction Scheme V, where $R^z$ is as defined in Reaction Scheme I, 2,5-dichlorophenyl boronic acid is reacted with a monofunctional 2-(4-bromophenyl)-1,3,4-oxadiazole of Formula CCLXI in the presence of palladium bis(triphenylphosphine)dichloride and sodium carbonate in an inert solvent such as tetrahydrofuran with heat to form the dihalogenated 1,3,4-oxadiazole intermediate of Formula CCLX.

The 2,5-dichlorophenyl boronic acid can be prepared by reacting 1-bromo-2,5-dichlorobenzene with butyl lithium and then with trimethyl borate followed by acidification.

Reaction Scheme V

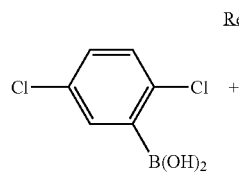

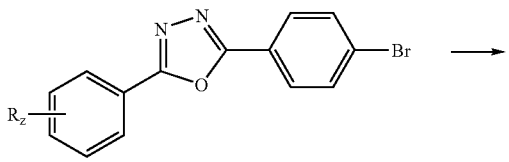

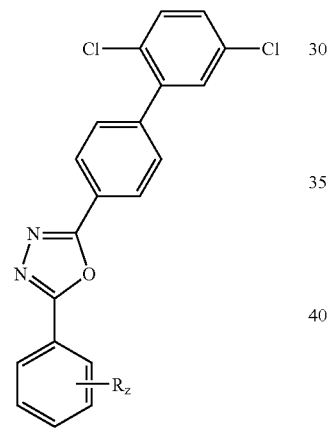

CCLX

For example, the electron transport intermediate 2-(2',5'-dichloro-1,1'-biphenyl-4-yl)-5-[4-(octyloxy)phenyl]-1,3,4-oxadiazole (9) can be prepared by reaction of 2,5-dichlorophenyl boronic acid with 2-(4-bromophenyl)-5-[4-(octyloxy)phenyl]-1,3,4-oxadiazole under standard Suzuki coupling conditions. The corresponding 1,3,4-thiadiazole (11) may be similarly prepared by reaction of 2,5-dichlorophenyl boronic acid with 2-(bromophenyl)-5-[4-(octyloxy)phenyl]-1,3,4-thiadiazole under standard Suzuki coupling conditions. Also, the corresponding triazole compound (10) may be similarly prepared by reaction of 2,5-dichlorophenyl boronic acid with the monofunctional 3-(4-bromophenyl)-4-(4-phenyl)-5-[4-(octyloxy)phenyl]-4H-1,2,4-triazole intermediate. The dichloro intermediates of Formula CCLX can be converted to the corresponding dibromo intermediates by a halogen exchange, for example, by reaction with hydrogen bromide in the presence of a catalytic amount of FeBr$_3$ (Yoon et al., *J. Chem. Soc., Chem. Commun.*, 13, 1013-1014 (1987)).

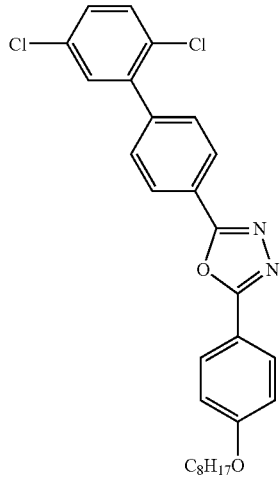

9

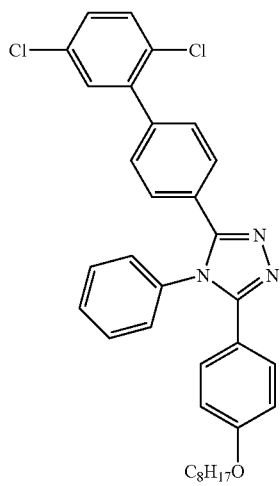

10

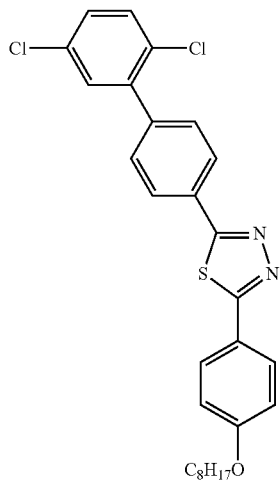

11

In one useful embodiment of Formula I, the $Ar^1$-$(E_y)_a$ group is a fluorene. These can be made, for example, using the diaroylhydrazide cyclocondensation route according to Reaction Scheme VI where RZ is as defined in Reaction Scheme I and where $R^3$ is independently in each case hydrogen, $C_{1-30}$ alkyl, $C_{1-30}$ alkenyl, $C_{6-20}$ aryl, $C_{3-20}$ heteroaryl, or $C_{1-30}$ hydrocarbyl containing one or more S, N, O, P, or Si atoms. In step (1) of Reaction Scheme VI a 2,7-dibromofluorene of Formula CCLXII is converted to the 4-methyl ester of Formula CCLXIII by reaction with methoxycarbonyl chloride in the presence of aluminum chloride in an inert solvent such as carbon disulfide. In step (2), the 4-methyl ester of Formula CCLXIII is converted to the hydrazide of Formula CCLXIV by reaction with hydrazine with heating. In step (3) the hydrazide of Formula CCLXIV is converted to the benzoylaroylhydrazide of Formula CCLXV by condensation with an unsubstituted or substituted benzoyl chloride of Formula CCLIV in the presence of triethylamine. In step (4) the benzoylaroylhydrazide of Formula CCLXV is cyclocondensed with phosphorus oxychloride at reflux to provide the dibromofluorenyl-1,3,4-oxadiazole of Formula CCLXVI.

For example, the electron transport intermediate 2-(2,7-dibromo-9,9-dioctyl-9H-fluoren-4-yl)-5-[4-(octyloxy)phenyl]-1,3,4-oxadiazole can be made by this method. In this case, 2,7-dibromo-9,9-disubstituted fluorene intermediate is converted to the 4-methyl ester (Bokova et al., *J. Org. Chem. USSR (Engl.Transl.)*, 5, 1103-1106 (1969)); Schidlo et al., *Chem Ber.*, 96, 2595-2600 (1963)), reacted with hydrazine, and then condensed with 4-(octyloxy)benzoylchloride to give the 2,7-dibromo-N'-[4-(octyloxy)benzoyl]-fluorenoyl hydrazide intermediate which upon cyclocondensation gives the desired intermediate.

The corresponding thiadiazole and triazole may be made by reaction of the intermediate benzoylaroylhydrazide of Formula CCLXV with $P_2S_5$ under metathesis conditions as in Reaction Scheme III to provide the 1,3,4-thiadiazole, and with $R_1NH_2$ as in Reaction Scheme IV to provide the 1,3,4-triazole.

In Reaction Scheme VII below, the $Ar^1$-$(E_y)_a$ group can also be constructed through an Ulmann self coupling reaction in step (1) of an iodo-substituted benzoyloxy ester of Formula CCLXVII (wherein A is H, Cl, or Br and $R^1$ is $C_{1-4}$ alkyl) with copper/bronze (see Rule et al., *J. Chem. Soc.*

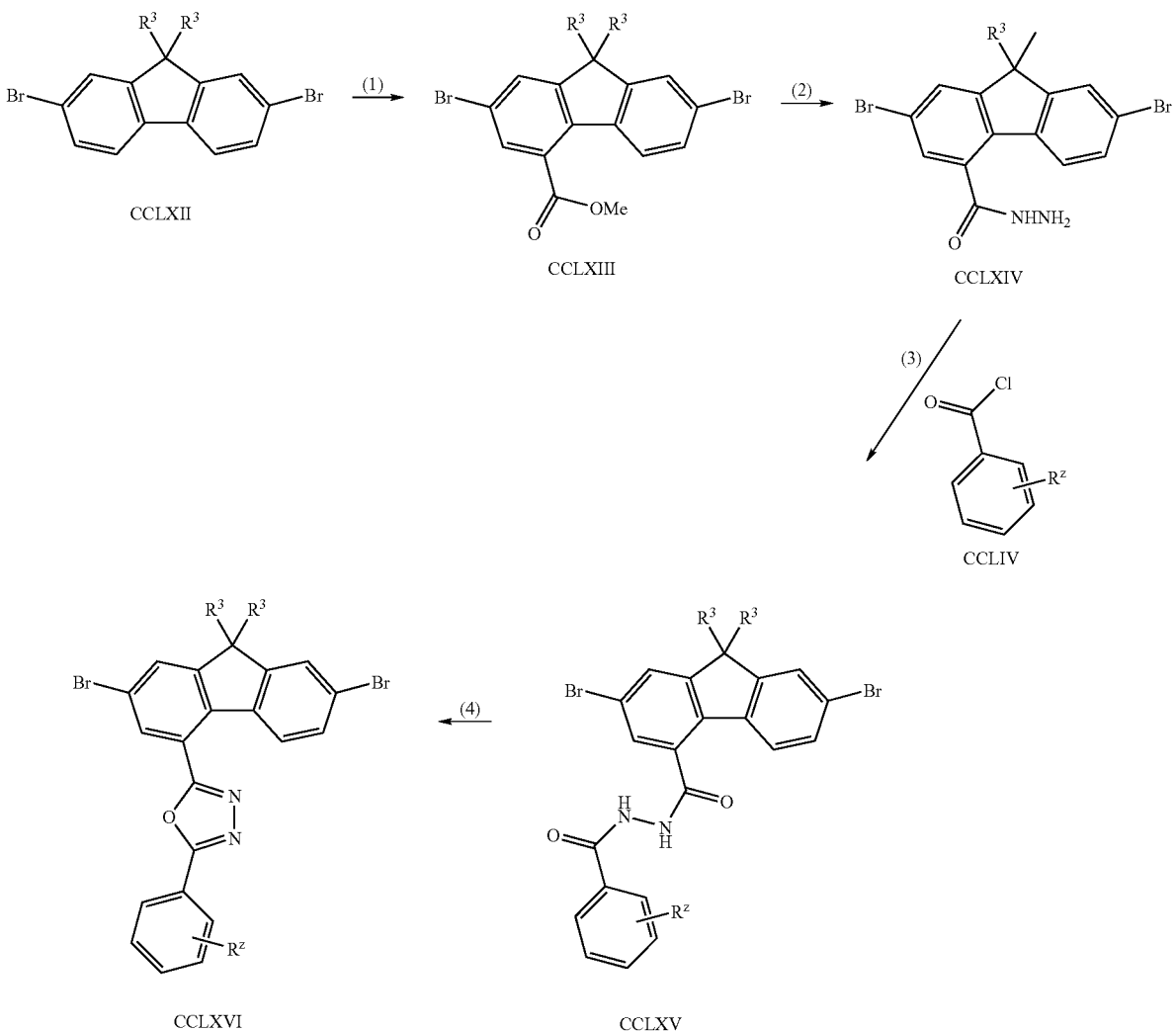

Reaction Scheme VI 1096-1101 (1937)); Namkung et al., *J. Med. Chem. Soc.*, 8, 551-554 (1965)) followed by acid promoted ring closure in step (2) of the resulting diphenic acid of Formula CCLXVIII (Huntress et al., *J. Am. Chem. Soc.*, 55, 4262-4270 (1933)), for example, with sulfuric acid at 170° C., to give the 9-fluorenone of Formula CCLXIX. Reduction of the 9-fluorenone with red phosphorus in step (3) provides the fluorene of Formula CCLXX, which can be alkylated at the 9-position in step (4) by reaction with butyl lithium followed by an $R^3$-halide or by phase transfer methods utilizing, for example, benzyltriethylammonium chloride in dimethylsulfoxide, followed by 50% aqueous sodium hydroxide and then $R^3$-Br. Halogenation of the resulting 9-alkylated fluorene of Formula CCLXXI, wherein A is H and R' is methyl, at the 2 and 7 positions can be done, for example, by reaction with chlorine in methyloxirane in step (5) to give the 2,7-dichloro fluorene of Formula CCLXXII, wherein R' is methyl (Schidlo et al., *Chem Ber.*, 2595-2600 (1963)). Treatment of the 2,7-dichloro fluorene of Formula CCLXXII with thionyl chloride in step (6) gives the reactive acyl chloride intermediate of Formula CCLXXIII. The oxadiazole, thiadiazole, or triazole may then be formed at the acyl chloride group of the acyl chloride intermediate via a benzohydrazide intermediate as in Reaction Schemes II-IV or by direct coupling with a tetrazole as in Reaction Scheme I.

The electron transport intermediate 2-[4-(2',7'-dichloro-9',9'-dioctyl-9'H-fluoren-4'-yl)phenyl ]-5-[4-(octyloxy)phenyl]-1,3,4-oxadiazole (12)

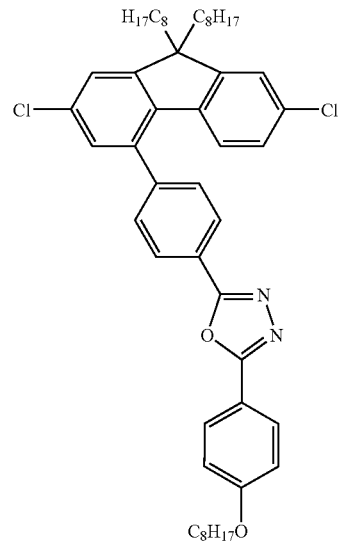

Reaction Scheme VII

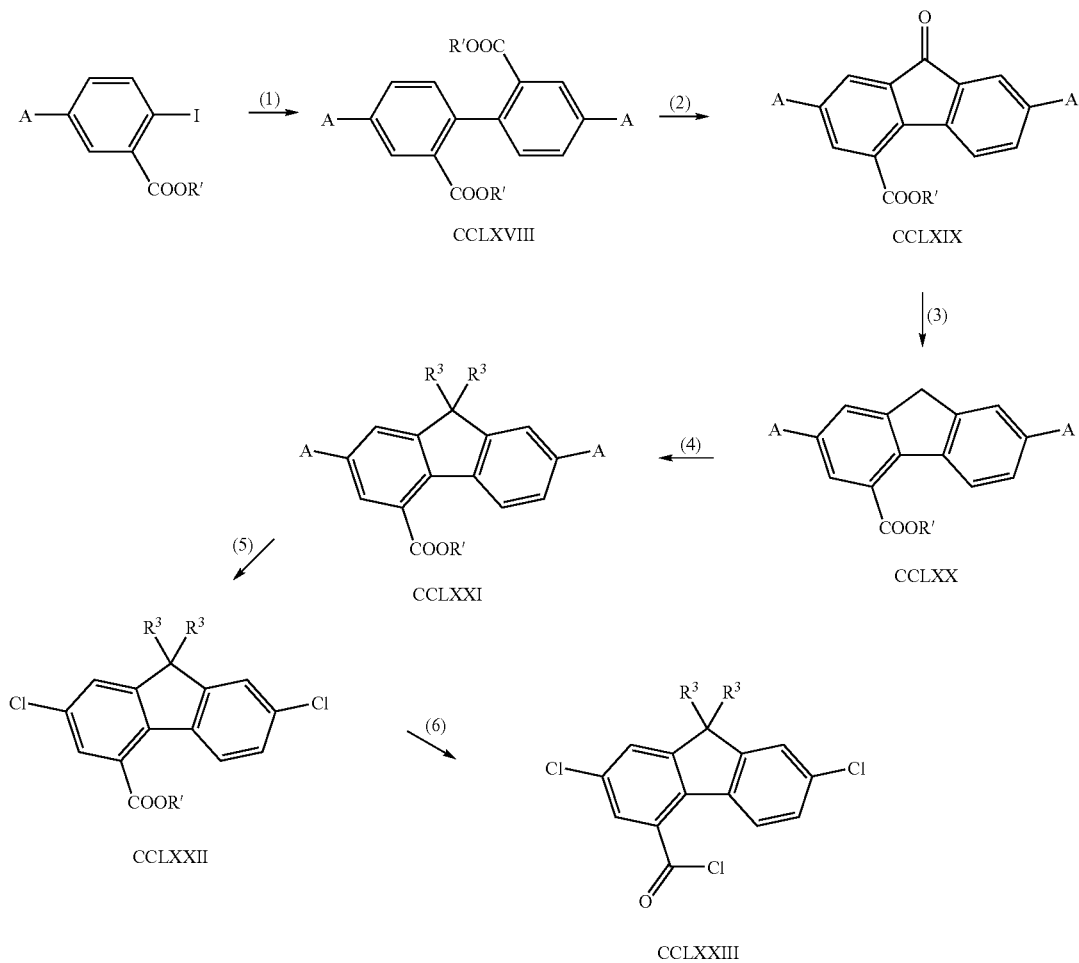

can be prepared by monobromination of 2,7-dichloro-9,9-dioctyl-9H-fluorene to give 4-bromo-2,7-dichloro-9,9-dioctyl-9H-fluorene, conversion to the corresponding dichloroboralane followed by reaction with 2-(4-bromophenyl)-5-[4-(octyloxy)phenyl]-1,3,4-oxadiazole under standard Suzuki coupling conditions.

Ar$^1$-(Ey)a groups that are based on 9,10-dihydrophenanthrene can be synthesized by the process shown in Reaction Scheme VIII below. In step (1), Suzuki coupling of the phenylborolane of Formula CCLXXV with the methyl cyanobromobenzoate of Formula CCLXXIV provides the cyanodiphenic ester of Formula CCLXXVI. In step (2), acyloin reduction (Fritsch et al., *Chem Ber.*, 125, 849-855 (1992)) can provide the cyano-9, 10-dihydrophenanthrene of Formula CCLXXVII. In step (3), dibromination with bromine, for example, in methylene chloride at room temperature, of CCLXXVII provides the dibromo-cyano-9,10-dihydrophenanthrene of Formula CCLXXVIII, the cyano group of which can be converted to a carboxylic acid group by treatment with base or to a tetrazole group by treatment with NaN$_3$ and NH$_4$Cl in DMF at reflux. An oxadiazolyl, thiadiazolyl, or triazolyl group can be formed from the carboxylic acid group by first halogenation with thionyl chloride or chlorine in methyloxirane, followed by formation of the oxadiazole, thiadiazole, or triazole group as in Reaction Schemes II, III, or IV. The tetrazole can be reacted with an aryloyl chloride as shown in Reaction Scheme II to form an oxadiazole.

nyl)-4,4,5,5-tetramethyl [1,3,2]dioxaborolane (CCLXXX) by treatment with butyl lithium and reaction of the lithiated intermediate with 2-isopropoxy-4,4,5,5-tetramethyl [1,3,2] dioxaborolane. In step (2), 2-(2,5-dimethylphenyl)fluoren-9-one (CCLXXXI) can be converted to 2-bromo-7-(4-bromo-2,5-dimethylphenyl)fluoren-9-one (CCLXXII) with bromine in chloroform at 0° C. Regiospecific bromination at the 4'-position of the phenyl ring is directed by the 5'-methyl and fluorene substituents. In step (3), 2-bromo-7-(4-bromo-2,5-dimethylphenyl)fluoren-9-one (CCLXXII) can undergo potassium permanganate oxidation to provide 2-bromo-5-(7-bromo-9-oxo-9H-fluoren-2-yl)-terephthalic acid (CCLXXIII). Ring closure, in step (4), to 2,8-dibromo-6,12-dioxa-6,12-dihydroindeno [1,2-b]fluorene-3-carboxylic acid (CCLXXXIV) is effected by treatment with sulfuric acid. Reduction of 2,8-dibromo-6,12-dioxa-6,12-dihydroindeno [1,2-b]fluorene-3-carboxylic acid (CCLXXXIV), in step (5), with red phosphorus provides 2,8-dibromo-6,12-dihydroindeno[1,2-b]fluorene-3-carboxylic acid (CCLXXXV). In step (6), alkylated by reaction with butyl lithium followed by an R$^3$-halide or by phase transfer methods utilizing, for example, benzyltriethylammonium chloride in dimethylsulfoxide, followed by 50% aqueous sodium hydroxide and then R$^3$-Br provides the indeno[1,2-b]fluorene derivative of Formula CCLXXXVI. Treatment of the indeno[1,2-b]fluorene of Formula CCLXXXVI with thionyl chloride gives the reactive acyl chloride intermediate of Formula CCLXXXVII. The oxadiazole, thiadiazole, or

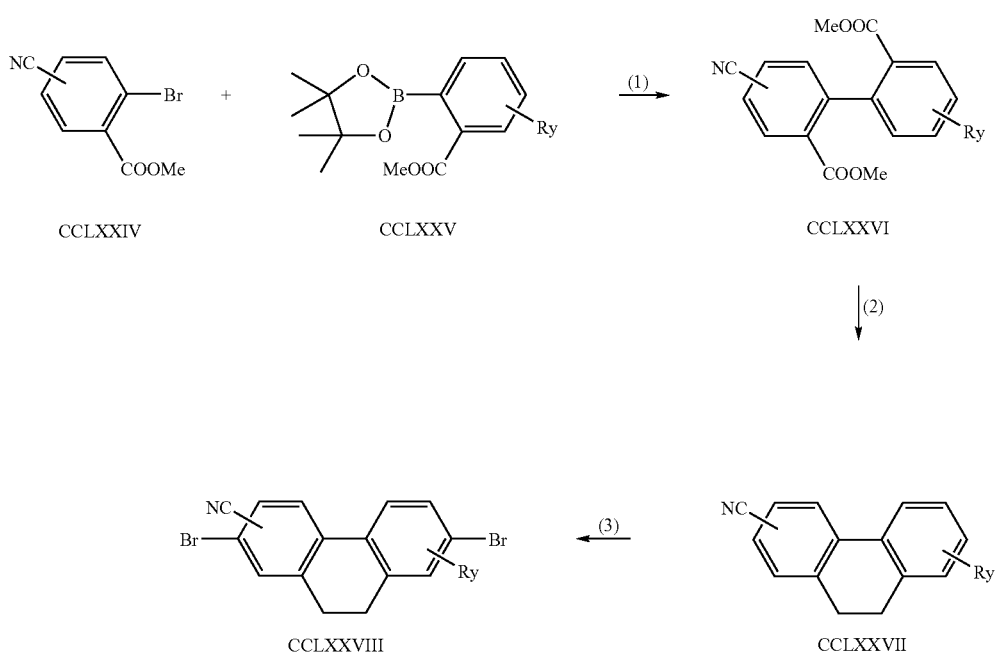

Groups of Ar$^1$-(E$_y$)$_a$ can be prepared by preparation of a 2,8-dibromo-6,12-dihydroindeno [1,2-b]fluorene using the process of Reaction Scheme IX. In step (1), Suzuki coupling of 2-(2,5-dimethylphenyl)-4,4,5,5-tetramethyl[1,3,2]dioxaborolane (CCLXXX) with commercially available 2-bromo-9-fluorenone (CCLXXIX) provides 2-(2,5-dimethylphenyl)fluoren-9-one (CCLXXXI). Commercially available 2-bromo-p-xylene is converted to 2-(2,5-dimethylphetriazole may be formed at the acyl chloride group of the acyl chloride intermediate via a benzhydrazide intermediate as in Reaction Schemes II-IV or by direct coupling with a tetrazole as in Reaction Scheme I. In step (8), for example, the oxadiazole of Formula CCLXXXVIII is provided by reaction of the acyl chloride intermediate of Formula CCLXXXVII with 5-(4-octyloxyphenyl)-1H-tetrazole as in Reaction Scheme I.

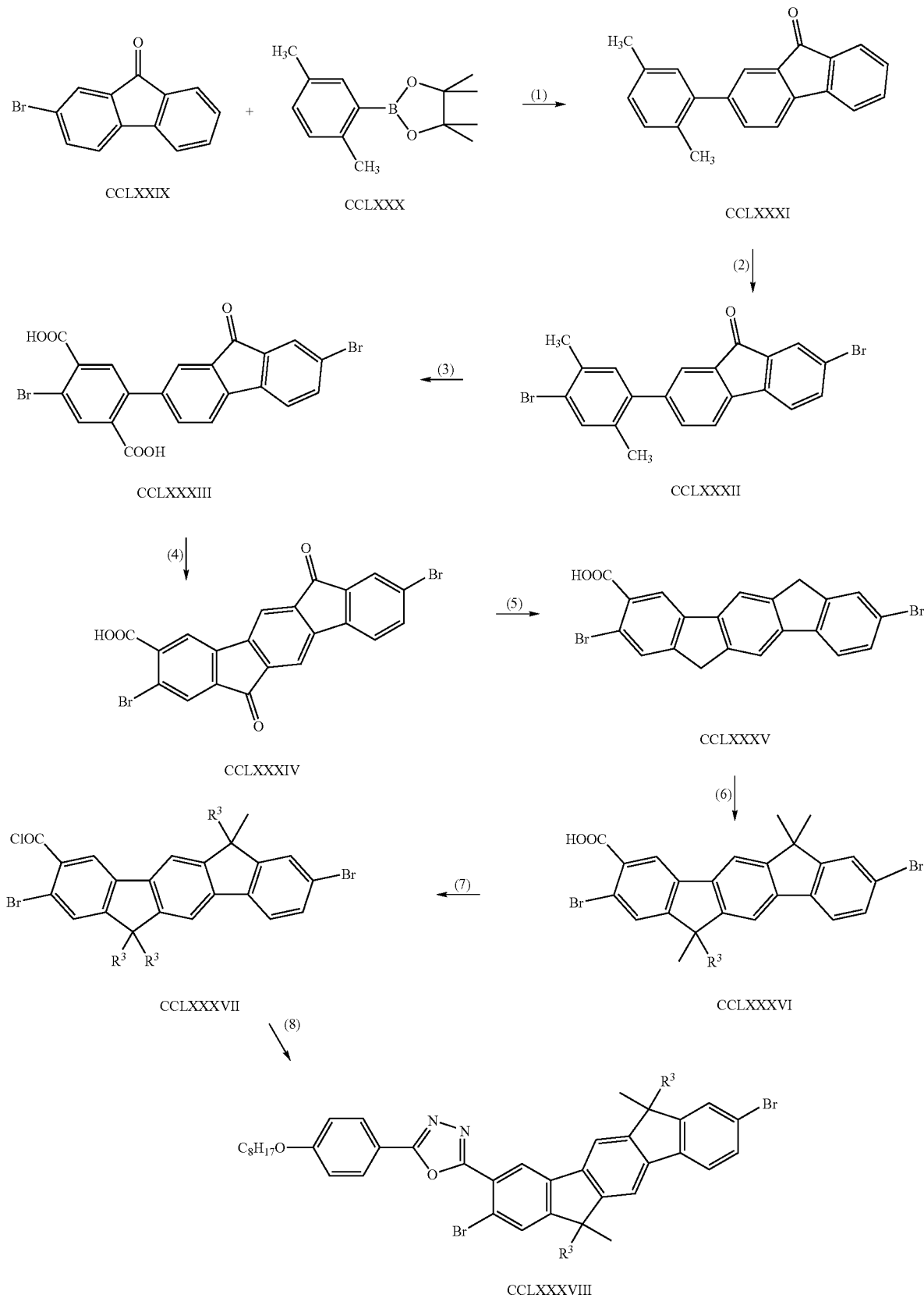
Reaction Scheme IX

Groups of $Ar^1$-$(E_y)_a$ having one or both terminal rings substituted with $E_y$, may be made by first making a dicarboxylic acid of 3,10-dibromo-5,6,12,13-tetrahydrodibenzo [a,h]anthracene as illustrated in Reaction Scheme X, below. In step (1), dimethyl 2,4-dibromoterephthalate (available from Maybridge Chemical Co., UK) is reacted with the cyanophenylborolane of Formula CCLXXXIX (see Kristensen et al., *Org. Lett.*, 10, 1435-1438 (2001)) to provide the cyano substituted triphenyl compound of Formula CCXC. Acyloin reduction (see Fritsch et al., *Chem Ber.*, 125, 849-855 (1992)) of the compound of Formula CCXC, in step (2), can give the dicyano substituted 5,6,12,13-tetrahydrodibenzo[a,h]anthracene of Formula CCXCI. Dibromination, for example, with bromine in chloroform at 0° C., in step (3), can provide the dicyano substituted 3,10-dibromo-5,6,12,13-tetrahydrodibenzo[a,h]anthracene of Formula CCXCII. Treatment of the compound of Formula CCXCII, in step (4), with base can give the dicarboxylic acid of Formula CCXCIII. In step (5), treatment of the compound of Formula CCXCIII with thionyl chloride can give the reactive acyl chloride intermediate of Formula CCXCIV.

As an alternative, the cyano groups of the dicyano substituted 3,10-dibromo-5,6,12,13-tetrahydrobenzo [a,h]anthracene or Formula CCXCII can be converted to tetrazole groups by treatment with $NaN_3$ and $NH_4Cl$ in DMF at reflux. The tetrazole can be reacted with an aryloyl chloride as shown in Reaction Scheme I to form an oxadiazole.

The monocyano substituted 5,6,12,13-tetrahydrodibenzo [a,h]anthracene of Formula CCXCV can be made through a sequential Suzuki coupling shown in Reaction Scheme XI. In step (1), the phenylborolane of Formula CCXCVI is reacted with excess (typically 5 equivalents) dimethyl 2,4-dibromoterephthalate to give the 4-bromobiphenyl of Formula CCXCVII as the major product. In step (2), after purification, the 4-bromobiphenyl of Formula CCXCVII is reacted with the cyanophenylborolane of Formula CCLXXXIX under similar Suzuki coupling conditions to give the monocyano substituted triphenyl of Formula CCXCVIII. In step (3), acyloin reduction as in Reaction Scheme X provides the monocyano substituted 5,6,12,13-tetrahydrodibenzo[a,h]anthracene of Formula CCXCV. Subsequent dibromination, for example, with bromine in chloroform at

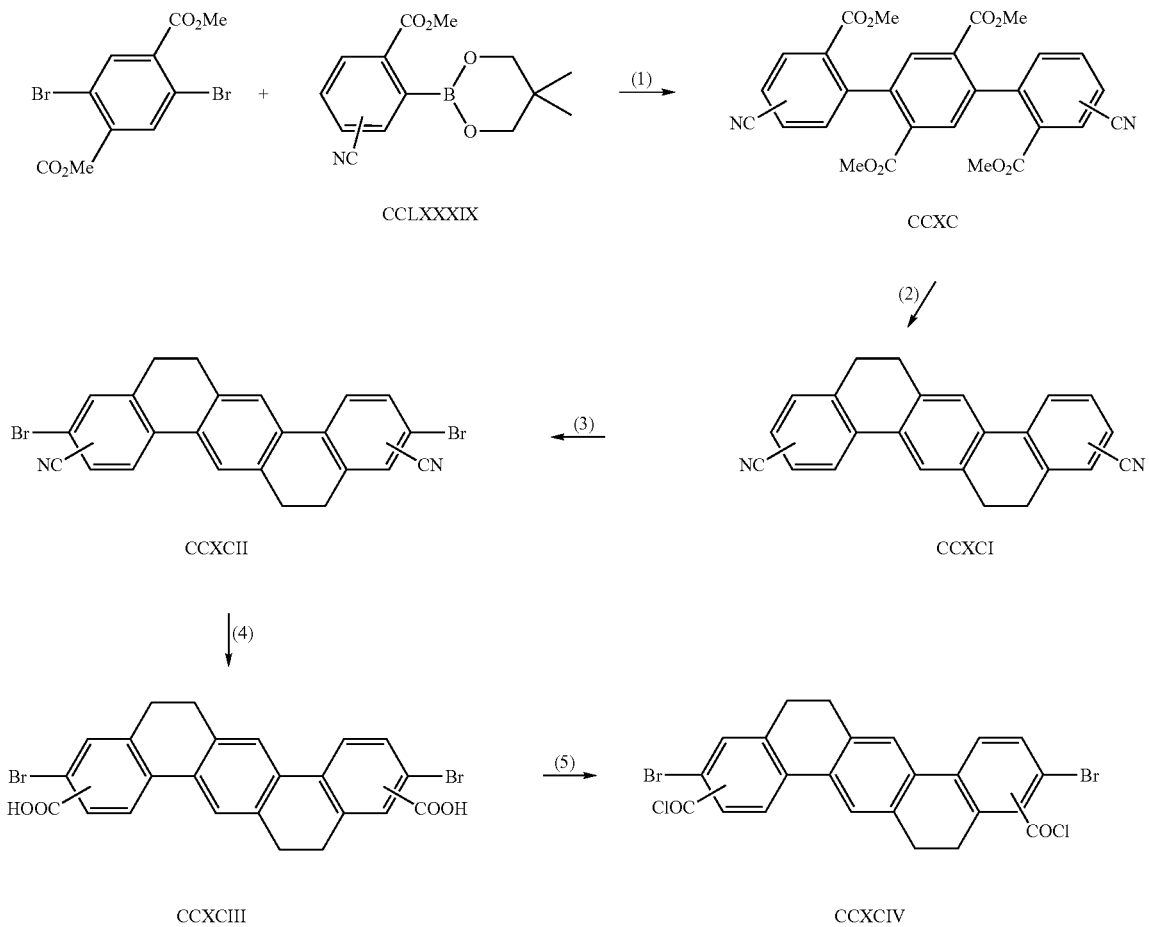

Reaction Scheme X

The oxadiazole, thiadiazole, or triazole may be formed at the acyl chloride groups of the acyl chloride intermediate of Formula CCXCIV via a benzoylaroylhydrazide intermediate as in Reaction Schemes II-IV or by direct coupling with a tetrazole as in Reaction Scheme I.

0° C., in step (4), may give the dibromo monocyano compound of Formula CCC. The dibromo monocyano compound of Formula CCC may be reacted with $NaN_3$ and $NH_4Cl$ in DMF at reflux, in step (5), to form the tetrazole of Formula CCCI, which can be reacted with an aroyl chloride, Ar²C(O)Cl, in step (6) to form the 5,6,12,13-tetrahydrodibenzo[a,h]anthracene bearing a pendant oxadiazole of Formula CCCII.

Alternatively, the cyano group on the compound of Formula CCC can be hydrolyzed to form the carboxylic acid, which can in turn be treated with thionyl chloride to form the acyl chloride intermediate. The acyl chloride intermediate may be reacted with an aroyl hydrazide as in Reaction Scheme II to form a benzoylaroylhydrazide, which can be converted to an oxadiazole, thiadiazole, or triazole as described in Reaction Schemes II-IV.

The dihalo intermediates prepared as described in the above reaction schemes can be converted to the corresponding diborolane by treatment with bis(pinacolato)diboron and potassium acetate catalyzed by [1,1'-bis(diphenylphosphino)ferrocene] dichloropalladium in dimethyl sulfoxide (Meng et al., *J. Am. Chem. Soc.*, 123(37), 9214-9215 (2001)) to give the diborolane derivative.

Compounds of Formula V can be synthesized by reacting the aryl boronic ester of a selected capping group with an excess of the dihalide of a selected aromatic core intermediate under Suzuki coupling conditions to generate an inter-

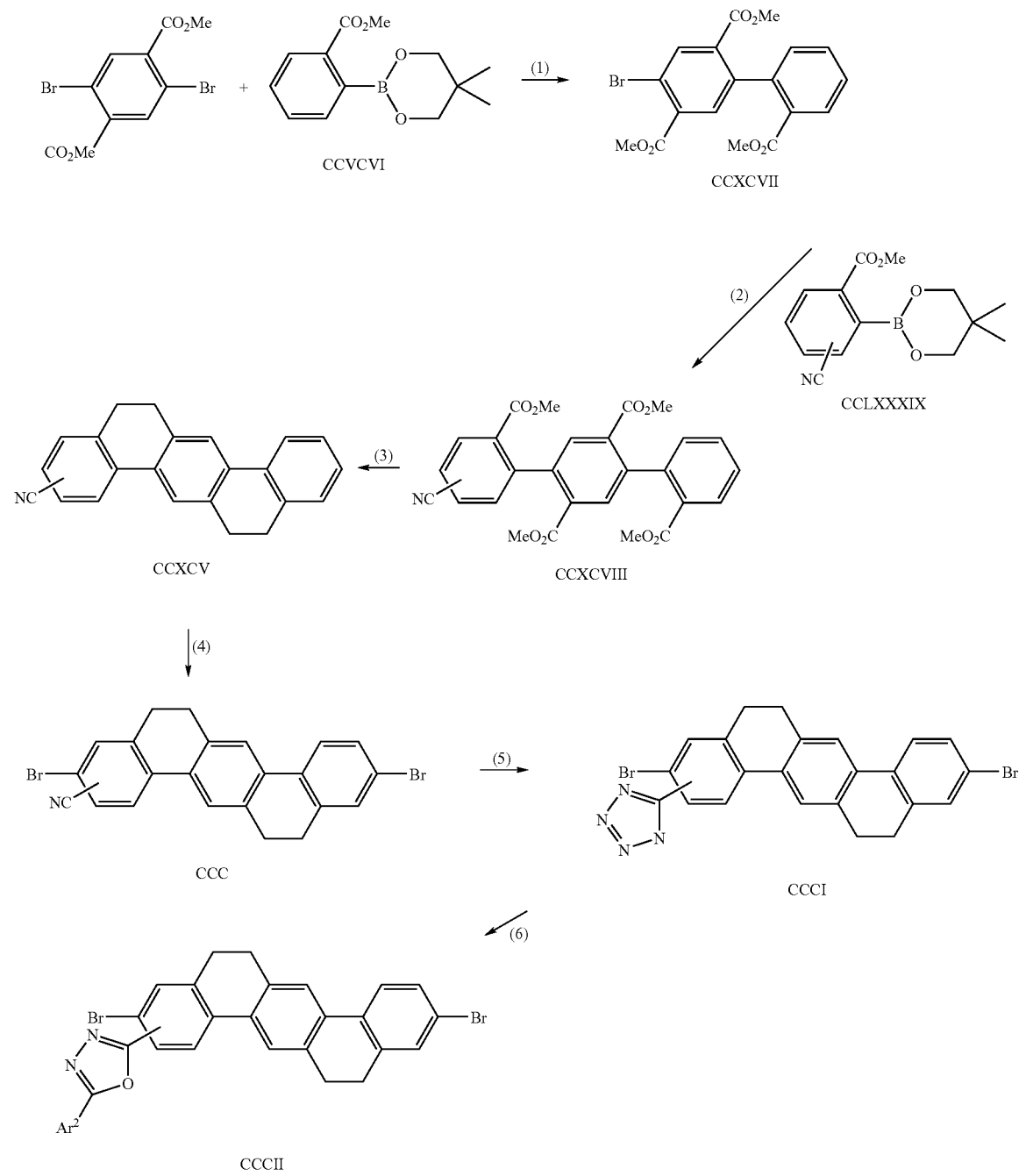

mediate having one capping group coupled to one monohalogenated aromatic core group. This intermediate can then be converted to the corresponding arylboronic ester intermediate by treatment with bis(pinacolato)diboron and potassium acetate catalyzed by [1,1'-bis(diphenylphosphino)ferrocene ]dichloropalladium in dimethyl sulfoxide (Ishiyama, et al in *J. Org. Chem.* 60, 7508-7510 (1995)). The arylboronic ester intermediate can be cross coupled with an end capped and monohalogented aromatic core of the same or different structure under Suzuki coupling conditions to arrive at the final compound of Formula V.

Compositions

There is a need in the art for solution processible electroluminescent compositions that can be uniformly coated or printed onto a substrate for the purpose of fabricating organic electroluminescent devices. OLED devices prepared from these compositions preferably should provide at least one of the following: low operating voltages, high external quantum efficiencies, proper color coordinates (e.g. red, green, and blue for display applications or white for backlight applications), long operating lifetimes, and compatibility with the printing process (e.g. inkjet printing, laser induced thermal imaging, gravure printing, etc).

One aspect of the invention provides compositions that can be used in organic electronic devices such as organic electroluminescent devices. The compositions include a compound according to Formula I that is blended with a charge transporting material, charge blocking material, light emitting material, color conversion material, polymeric binder, or a combination thereof. The charge transporting material can be either a small molecule or a polymeric material and can transport holes, electrons, or a combination thereof. The charge blocking material can be either a small molecule or a polymeric material and can block holes, electrons, or a combination thereof. The light emitting material and the color conversion material can be either a small molecule or polymeric material. Such blends can be prepared, for example, by blending the compounds in a solution or in a melt state. The compositions can be in the form of film prepared from the blended compounds.

Such compositions can be useful for making organic electronic devices by thermal patterning of the materials onto a receptor. They can also be useful for non-thermal printing, patterning, and transfer methods including, for example, inkjet printing, screen printing, and photolithographic patterning.

Hole transport agents useful in these compositions are preferably selected from tertiary aromatic amine derivatives as defined above, electron rich heteroarylene derivatives as defined above, electron rich inorganic and organometallic complexes, or polymers derived from these materials. Hole transport polymers useful in these blends include polyvinyl carbazoles, triaryl amine based polymer of the types taught in DE Patent No. 3,610,649, U.S. Pat. No. 5,681,664, patent application WO 99/32537, and patent application WO 98/06773, all of which are incorporated by reference. Other examples of hole transport agents include copper phthalocyanine (CuPC) and compounds such as those described in H. Fujikawa, et al., *Synthetic Metals*, 91, 161 (1997) and J. V. Grazuleviciua et al., "Charge-Transporting Polymers and Molecular Glasses", *Handbook of Advanced Electronic and Photonic Materials and Devices*, H. S. Nalwa (ed.), 10, 233-274 (2001), both of which are incorporated herein by reference.

Electron transport agents useful in these blended systems can be selected from polycyclic aromatic hydrocarbons, heteroaromatic compounds having —C═N— units, and electron deficient inorganic complexes. Suitable electron transport agents include oxadiazole derivatives such as 2-(4-biphenyl)-5-(4-t-butylphenyl)-1,3,4-oxadiazole (also known as PBD), 1,3-bis[5-(4-(1,1-dimethylethyl)phenyl)-1,3,4-oxadiazol-2-yl ]benzene (known as PBD dimer) as well as starburst and dendrimeric derivatives of oxadiazoles (Bettenhausen et al., *Synthetic Metals*, 91, 223 (1997)), incorporated herein by reference; N-substituted triazole derivatives such as 3-(4-biphenylyl)-4-phenyl-5-(4-tert-butylphenyl)1,2,4-triazole (also known as TAZ) as well as starburst and dendrimeric derivatives of triazoles; organometallic compounds such as tris(8-hydroxyquinolato) aluminum ($Alq_3$) and biphenylatobis(8-hydroxyquinolato)aluminum (Balq); and other compounds described in C. H. Chen et al., *Macromol. Symp.* 125, 1 (1997) and J. V. Grazulevicius et al., "Charge-Transporting Polymers and Molecular Glasses", *Handbook of Advanced Electronic and Photonic Materials and Devices*, H. S. Nalwa (ed.),10, 233 (2001), both of which are incorporated herein by reference.

Small molecule emitters useful in these blended systems are without restriction, but are typically selected from molecular emitters derived from fluorescent polynuclear arylene and heteroarylene derivatives, phosphorescent cyclometallated chelate complexes of Ir(III), Rh(III), Os(II), Ru(II), Ni(II) and Pt(II), and fluorescent chelate complexes of Zn(II) and Al(III). Examples of useful fluorescent polynuclear arylene emitters include molecules derived from perylene, benzo[g,h,i]perylene, anthracene, pyrene, decacyclene and fluorenes. Examples of useful fluorescent polynuclear heteroarylene derivatives include molecules derived from coumarins such as 10-(2-benzothiazolyl)-2,3,6,7-tetrahydro-1,1,7,7-tetramethyl-1H,5H,11H-[1]benzopyrano[6,7,8-ij]quinolizin-11-one (also known as Coumarin C545T), 3-(2-benzothiazolyl)-7-diethylaminocoumarin (also known as Coumarin 6 or Coumarin 540), and 3-thiophenyl-7-methoxycoumarin.

Examples of useful phosphorescent cyclometallated chelate complexes of Ir(III), Rh(III), Os(II), Ru(II), and Pt(II) include molecules derived from phosphorescent organometallic $L^1{}_3Ir$ (III), $L^1{}_3Rh$ (III), $L^1L^2Ir(III)X$, $L^1L^2Rh(III)X$, $L^1L^2Os(II)Y$, $L^1L^2Ru(II)Y$, $L^1L^2Pt(II)$ compounds where $L^1$ and $L^2$ can be the same or different in each instance and are optionally substituted cyclometallated bidentate ligands of 2-(1-naphthyl)benzoxazole, 2-phenylbenzoxazole, 2-phenylbenzothiazole, 2-phenylbenzimidazole, 7,8-benzoquinoline, coumarin, (thienylpyridine), phenylpyridine, benzothienylpyridine, 3-methyoxy2-phenylpyridine, thienylpyridine, tolylpyridine; X is selected from the group consisting of acetylacetonate ("acac"), hexafluoroacetylacetonate, salicylidene, picolinate, and 8-hydroxyquinolinate; Y is selected from charge neutral chelating compounds such as an optionally substituted derivatives of phenathroline or bipyridine. Cyclometallated Ir(III) chelate derivatives such as those taught in patent applications WO 00/70655 and WO 01/41512 A1 and cylcometalated Os(II) chelate derivatives such as those taught in U.S. Pat. No. 6,664,111 are herewith incorporated by reference. Platinum(II) porphyrins such as octaethyl porphyrin (also known as Pt(OEP)) are also useful.

Examples of useful fluorescent chelate complexes of Zn(II) and Al(III) include complexes such as bis(8-quinolinolato) zinc(II), bis(2-(2-hydroxyphenyl)benzoxazolate) zinc(II), bis(2-(2-hydroxyphenyl)benzothiazolate) zinc(II), bis(2-(2-hydroxyphenyl)-5-phenyl-1,3,4-oxadiazole) zinc (II), bis(8-quinolinolato) aluminum(III), and biphenylatobis (8-hydroxyquinolato)aluminum (BALq). Fluorescent Zn (II) chelates such as those taught by Tokito et al., *Synthetic*

*Metals,* 111-112, 393-396, (2000) and in patent application WO 01/39234 A2, all of which are incorporated by reference. Useful Al(III) chelates include those taught in U.S. Pat. No. 6,203,933B1, incorporated herein by reference.

Suitable light emitting polymers for use in these blends are polymers and copolymers of the polyfluorenes (PFs), polyparaphenylenes (PPPs), polyphenylenevinylenes (PPVs), and polyspirobisfluorenes.

In one embodiment, a compound according to Formula I is blended with one or more materials to provide a composition that can transport both holes and electrons. For example, a compound of Formula I that can transport electrons can be combined with either a small molecule or a polymeric hole transporting material. Such a composition can be charge balanced by virtue of the blend ratio and the compounds selected. Optionally, a light emitting polymer or electroluminescent small molecule can be added to the blend to form compositions that can be formed into an organic emissive element.

These types of compositions can be solution processible and can be spin coated to provide thin films that are electroluminescent. The compositions can be, for example, in the form of an amorphous film that can be thermally transferred from a donor substrate to a receptor substrate. The compositions can be thermally imaged to form pixilated arrays useful in OLED display manufacture and can be optimized to give rise to high quantum efficiency electroluminescence by varying the thickness of the film and the ratio of components within the ranges specified. The emission color can be varied by choice of the light emitting material. For example, perylene, bis(2-(2-hydroxyphenyl)benzoxazolate) zinc(II), or 3-thienyl-7-methoxy-coumarin give rise to blue emission; benzothienyl pyridine acetylacetonate iridium(III), or platinum octaethylporphyrin give rise to red emission; Coumarin 6, Coumarin C545T and Ir(ppy)$_3$ give rise to green emission; and t-butylated decacyclene gives rise to white emission.

The compositions can include a first compound according to Formula I and a second compound that has structural similarities to the first compound. A compound of Formula I has a aromatic core and two end capping groups that are attached to the aromatic core. The second compound can include a radical that includes the aromatic core of the first compound, a monovalent radical that includes the end capping group of the first compound, a divalent radical that includes a divalent radical of the end capping group of the first compound, or a combination thereof. The second compound can be, for example, a light emitting material, a color conversion material, a charge transporting material, a charge blocking material, a polymeric binder, or a combination thereof.

In this aspect, the second compound can be unsubstituted, can have a substituent of a same type that is present on the corresponding structure of the first compound, or can be substituted with a substituent that is absent on the corresponding structure of the first compound. In some embodiments, the substituent on a radical of the second compound can be identical to that on a corresponding structure of the first compound. The corresponding structure of the first compound can be the first aromatic core, the first end capping group, or a divalent radical of the first end capping group. Both the radical of the second compound and the corresponding structure of the first compound can be free of substituents. In a specific example, the first end capping group can be a radical of anthracene without any substituent group and the second compound includes a radical of anthracene without any substituent group. Similarly, both the radical of the second compound and the corresponding structure of the first compound can have identical substituents. In a specific example, the first end capping group can be a radical of anthracene with a methoxy substituent and the second compound includes a radical of anthracene with a methoxy substituent in the same position as in the first end capping group.

Additionally, the second compound can contain a radical that is similar to, but not identical to, a corresponding structure of the first compound. For example, a substituent on a radical of the second compound can be absent on a corresponding structure of the first compound. In a specific example, the first end capping group is a radical of anthracene without any substituent groups and the second compound includes a radical of anthracene with a methoxy substituent. Likewise, a substituent on a radical included in the first compound can be absent on a corresponding structure of the second compound. In another specific example, the first compound has an end capping group that is a spirobisfluorenyl group with a methyl substituent and the second compound has an end capping group that is an unsubstituted spirobisfluorenyl group.

A substituent on a radical of the second compound can be of the same type of substituent (e.g., alkyl, alkenyl, alkoxy, aryl, aryloxy, fluoro, fluoroalkyl, perfluoroalkyl, heteroalkyl, heteroaryl, or combinations thereof) present on the corresponding structure of the first compound but contain a different number of carbon atoms. In a specific example, the first end capping group is a radical of anthracene with a methoxy substituent and the second compound includes a radical of anthracene with an ethoxy substituent. In another specific example, the first compound has an end capping group that is a spirobisfluorenyl group substituted with a methyl group and the second compound contains an end capping group that is a spirobisfluorenyl group substituted with a tert-butyl group.

The substituents on the first compound and the second compound cannot be of a different type if they are substituted in the same position. In a specific example, if the first end capping group is a spirobisfluorenyl group substituted with a methyl group and the second compound has a spirobisfluorenyl group substituted with a phenyl group in the same position where the methyl group is located on the first end capping groups, then the groups are not considered to be structurally similar.

The second compound of the composition can be a small molecule (i.e., non-polymeric) or can be a polymeric material. In some embodiments, the composition includes both a hole transporting material and an electron transporting material. In other embodiments, the composition includes a hole transporting material, an electron transporting material, and a light emitting material.

In one embodiment of a composition of the invention, the first compound is a compound according to Formula I and has a first end capping group (e.g., the first compound can be represented, for example by the formula $Z_1$-A-$Z_1$ where A is the aromatic core and $Z_1$ are two identical end capping groups). The second compound can be polymeric or a small molecule (i.e., non-polymeric) and has a second end capping group that includes the first end capping group(e.g., the second compound has an end capping group $Z_2$; and $Z_2$ includes $Z_1$).

In a variation of this first embodiment, the first end capping group or the second end capping group has a substituent that is absent in the other moiety. In another variation, the first end capping group and the second end capping group have the same type of substituents (e.g., alkyl, alkenyl, alkoxy, aryl, aryloxy, fluoro, fluoroalkyl, perfluoroalkyl, heteroalkyl, heteroaryl, or combinations thereof) but the number of carbon atoms in the substituents are different.

In a second embodiment, the first compound is a compound according to Formula I and has a first aromatic core (e.g., the first compound can be represented, for example by the formula $Z-A_1-Z$ where $A_1$ is the first aromatic core and Z are two identical end capping groups). The second compound can be polymeric or a small molecule and contains a radical that includes the first aromatic core (e.g., the second compound contains a radical $A_2$ and $A_2$ includes $A_1$).

In a variation of the second embodiment, the first aromatic core or the corresponding radical in the second compound has a substituent that is absent in the other moiety. In another variation, the first aromatic core and the corresponding radical in the second compound have the same type of substituents (e.g., alkyl, alkenyl, alkoxy, aryl, aryloxy, fluoro, fluoroalkyl, perfluoroalkyl, heteroalkyl, heteroaryl, or combinations thereof) but the number of carbon atoms in the substituents are different.

In a third embodiment, the first compound is a compound according to Formula I and has a first end capping group (e.g., the first compound can be represented, for example, by the formula $Z_1-A-Z_1$ where A is the aromatic core and $Z_1$ are two identical first end capping groups). The second compound is a small molecule and has a second end capping group that includes the first end capping group (e.g., the second compound can be represented, for example, by the formula $Z_2-B-Z_2$ where B is the aromatic core and $Z_2$ are two identical second end capping groups; and $Z_2$ includes $Z_1$). Such a composition could be used, for example, to prepare a film that includes two small molecules with an active (i.e., electroactive or electroluminescent) aromatic core. The similar end capping groups can be used to enhance the compatibility of the two small molecules.

In a variation of the third embodiment, the first end capping group or the second end capping group can contain a substituent that is lacking in the other end capping group. In another variation, both the first and the second end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a fourth embodiment, the composition includes a first compound according to Formula I, a second compound that is a small molecule, and a third compound that is a light emitting polymer. The first compound has a first end capping group (e.g., the first compound can be represented, for example, by the formula $Z_1-A-Z_1$ where A is the aromatic core and $Z_2$ are two identical first end capping groups) and the second compound has a second end capping group that includes the first end capping group (e.g., the second compound can be represented, for example, by the formula $Z_2-B-Z_2$ where B is the aromatic core and $Z_2$ are two identical second end capping groups; and $Z_2$ includes $Z_1$). Such a composition could be used, for example, to prepare a film that includes a small molecule blend with a light emitting polymer where the end capping groups of the first and second compound can enhance the compatibility of the entire composition. The small molecules can include active aromatic cores.

In a variation of the fourth embodiment, the first end capping group or the second end capping group can contain a substituent that is lacking in the other end capping group. In another variation, both the first and the second end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a fifth embodiment, the composition includes a first compound according to Formula I, a second compound that is a small molecule, and third compound that is an electroactive polymer. The first compound has a first end capping group (e.g., the first compound can be represented, for example, by the formula $Z_1-A-Z_1$ where A is the aromatic core and $Z_1$ are two identical first end capping groups) and the second compound has a second end capping group that includes the first end capping group (e.g., the second compound can be represented, for example, by the formula $Z_2-B-Z_2$ where B is the aromatic core and $Z_2$ are two identical second end capping groups; and $Z_2$ includes $Z_1$). Such a composition could be used, for example, to prepare a film that includes a small molecule blend with an electroactive polymer where the end capping groups of the first and second compound can enhance the compatibility of the entire composition. The small molecules can include active aromatic cores.

In a variation of the fifth embodiment, the first end capping group or the second end capping group can contain a substituent that is lacking in the other end capping group. In another variation, both the first and the second end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a sixth embodiment, the composition include a first compound according to Formula I, a second compound that is a small molecule, and a third compound that is an inactive polymer. As used herein, the term "inactive polymer" refers to a polymer that is not electroactive and that is not a light emitting polymer. The inactive polymer can serve, for example, as a matrix for the first compound and the second compound. The first compound has a first end capping group (e.g., the first compound can be represented, for example, by the formula $Z_1-A-Z_1$ where A is the aromatic core and $Z_1$ are two identical first end capping groups) and the second compound has a second end capping group that includes the first end capping group (e.g., the second compound can be represented, for example, by the formula $Z_2-B-Z_2$ where B is the aromatic core and $Z_2$ are two identical second end capping groups; and $Z_2$ includes $Z_1$). Such a composition could be used, for example, to prepare a film that includes a small molecule blend in an inactive polymer matrix where the end capping groups of the first and second compound can enhance the compatibility of the entire composition. The small molecules can include active aromatic cores.

In a variation of this sixth embodiment, the first end capping group or the second end capping group can contain a substituent that is lacking in the other end capping group. In another variation, both the first and the second end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a seventh embodiment, the composition includes a first compound according to Formula I and a second compound that is a small molecule. The first compound has a first aromatic core (e.g., the first compound can be represented, for example, by the formula $Z-A_1-Z$ where $A_1$ is the first aromatic core and Z are two identical end capping groups) and the second compound contains a corresponding radical that includes the first aromatic core (e.g., the second compound can be represented, for example, by the formula Y-$A_2$-Y where $A_2$ is the second aromatic core and Y are two identical end capping groups; and $A_2$ includes $A_1$). Such a composition could be used, for example, to prepare a film that includes two small molecules with active (i.e., electroactive or electroluminescent) end capping groups. The similar aromatic cores can be used, for example, to enhance the compatibility of the two small molecules.

In a variation of the seventh embodiment, either the first aromatic core or the corresponding radical in the second compound contain a substituent that is lacking in the other moiety. In another variation, both the first aromatic core and the corresponding radical in the second compound have substituents that are of the same type (e.g., alkyl, alkenyl, alkoxy, aryl, aryloxy, fluoro, fluoroalkyl, perfluoroalkyl, heteroalkyl, heteroaryl, and combinations thereof) but the substituents can contain a different number of carbon atoms.

In an eighth embodiment, the composition includes a first compound according to Formula I, a second compound that is a small molecule, and a third compound that is a light emitting polymer. The first compound has a first aromatic core (e.g., the first compound can be represented, for example, by the formula Z-$A_1$-Z where $A_1$ is the first aromatic core and Z are two identical end capping groups) and the second compound contains a corresponding radical that includes the first aromatic core (e.g., the second compound can be represented, for example, by the formula Y-$A_2$-Y where $A_2$ is the second aromatic core and Y are two identical end capping groups; and $A_2$ includes $A_1$). Such a composition could be used, for example, to prepare a film that includes a small molecule blend with a light emitting polymer where the aromatic cores of the first and second compound can enhance the compatibility of the entire composition. The small molecules can include, for example, active end capping groups.

In a variation of the eighth embodiment, either the first aromatic core or the corresponding radical in the second compound can contain a substituent that is lacking in the other moiety. In another variation, both the first aromatic core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) .but the substituents can contain a different number of carbon atoms.

In a ninth embodiment, the composition includes a first compound according to Formula I, a second compound that is a small molecule, and a third compound that is an electroactive polymer. The first compound has a first aromatic core (e.g., the first compound can be represented, for example, by the formula Z-$A_1$-Z where $A_1$ is the first aromatic core and Z are two identical end capping groups) and the second compound contains a corresponding radical that includes the first aromatic core (e.g., the second compound can be represented, for example, by the formula Y-$A_2$-Y where $A_2$ is the second aromatic core and Y are two identical end capping groups; and $A_2$ includes $A_1$). Such a composition could be used, for example, to prepare a film that includes a small molecule blend with an electroactive polymer where the aromatic cores of the first and second compound can enhance the compatibility of the entire composition. The small molecules can include, for example, active end capping groups.

In a variation of the ninth embodiment, either the first aromatic core or the corresponding radical in the second compound can contain a substituent that is lacking in the other moiety. In another variation, both the first aromatic core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a tenth embodiment, the composition includes a first compound according to Formula I, a second compound that is a small molecule, and a third compound that is an inactive polymer. The first compound has a first aromatic core (e.g., the first compound can be represented, for example, by the formula Z-$A_1$-Z where $A_1$ is the first aromatic core and Z are two identical end capping groups) and the second compound contains a corresponding radical that includes the first aromatic core (e.g., the second compound can be represented, for example, by the formula Y-$A_2$-Y where $A_2$ is the second aromatic core and Y are two identical end capping groups; and $A_2$ includes $A_1$). Such a composition could be used, for example, to prepare a film that includes a small molecule blend with an inactive polymer where the aromatic cores of the first and second compound can enhance the compatibility of the entire composition. The small molecules can include, for example, active end capping groups.

In a variation of the tenth embodiment, either the first aromatic core or the corresponding radical in the second compound can contain a substituent that is lacking in the other moiety. In another variation, both the first aromatic core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In an eleventh embodiment, the composition includes a first compound according to Formula I and a second compound that is a polymer. The first compound has a first aromatic core (e.g., the first compound can be represented by the formula Z-$A_1$-Z where $A_1$ is the first aromatic core and Z are two identical end capping groups). The polymer is a reaction product of a monomer mixture that includes a first monomer that contains a radical that includes the first aromatic core (e.g., the first monomer contains a radical $A_2$; and $A_2$ includes Al). Such a composition can be used, for example, to prepare a film that includes a small molecule having groups in common with a polymer. The common groups can enhance the compatibility of the compounds in the composition.

In a variation of the eleventh embodiment, either the first aromatic core or the corresponding radical in the second compound can contain a substituent that is lacking in the other moiety. In another variation, both the first aromatic core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a twelfth embodiment, the composition includes a first compound according to Formula I and a second compound that is a polymer. The first compound contains a first end capping group (e.g., the first compound can be represented, for example, by a formula $Z_1$-A-$Z_1$ where A is the aromatic core and $Z_1$ are two identical first end capping groups). The polymer is a reaction product of a monomer mixture that includes a first monomer that contains a divalent radical that includes a divalent radical of the first end capping group (e.g., the first monomer contains $Z_2$; and $Z_2$ includes a radical of $Z_1$). Such a composition can be used, for example, to prepare a film that includes a small molecule having groups in common with a polymer. The similar groups in both the first and second compound can enhance the compatibility of the compounds in the composition.

In a variation of the twelfth embodiment, the first end capping group or the second end capping group can contain a substituent that is lacking in the other end capping group. In another variation, both end capping groups can have substituents that are of the same type (e.g., alkyl, alkenyl, alkoxy, aryl, aryloxy, fluoro, fluoroalkyl, perfluoroalkyl, heteroalkyl, heteroaryl, and combinations thereof) but the substituents can contain a different number of carbon atoms.

In a thirteenth embodiment, the composition includes a first compound according to Formula I, a second compound that is a small molecule, and a polymer. The first compound has a first end capping group and a first aromatic core (e.g., the first compound can be represented, for example, by the formula $Z_1$-A-$Z_1$ where A is the first aromatic core and $Z_1$ are two identical first end capping groups). The second compound has a second end capping group that includes the first end capping group $Z_1$ but a second aromatic core that is different than the first aromatic core (e.g., the second compound can be represented, for example, by the formula $Z_2$-B-$Z_2$ where B is the second aromatic core and $Z_2$ are two identical second end capping groups; $Z_1$ includes $Z_2$; and B does not include A). The polymer is the reaction product of a monomer mixture that includes a first monomer that contains a radical that includes the first aromatic core and a second monomer that contains a radical that includes the second aromatic core (e.g., the first monomer contains a radical $A_3$ and the second monomer contains a radical $B_3$; $A_3$ includes A; and $B_3$ includes B). Such a composition can be used, for example, to prepare a film that includes small molecules that have groups in common with a polymer formed by reacting the monomer mixture. The similar groups in both the small molecules and the similar groups between the small molecules and the polymer can enhance the compatibility of the compounds in the composition.

In a first variation of the thirteenth embodiment, the first end capping group or the second end capping group can contain a substituent that is lacking in the other end capping group. In a second variation, both end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms. In a third variation, either the first aromatic core or the corresponding radical in the polymer can contain a substituent that is lacking in the other moiety. In a fourth variation, both the first aromatic core and the corresponding radical in the polymer can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms. In a fifth variation, either the second aromatic core or the corresponding radical in the polymer can contain a substituent that is lacking in the other moiety. In another variation, both the second aromatic core and the corresponding radical in the polymer have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a fourteenth embodiment, the composition includes a first compound according to Formula I, a second compound that is a small molecule, and a polymer. The first compound has a first aromatic core and a first end capping group (e.g., the first compound can be represented, for example, by the formula Z-$A_1$-Z where $A_1$ is the first aromatic core and Z are two identical first end capping groups). The second compound has a second aromatic core that includes the first aromatic core but a second end capping group that is different than the first end capping group (e.g., the second compound can be represented, for example, by the formula Y-$A_2$-Y where $A_2$ is the second aromatic core and Y are two identical second end capping groups; and $A_2$ includes $A_1$). The polymer is the reaction product of a monomer mixture that includes a first monomer that contains a divalent radical of the first end capping group and a second monomer that contains a divalent radical of the second end capping group (e.g., the first monomer can contain the radical $Z_3$ and the second monomer can contain the radical $Y_3$; $Z_3$ includes a radical of Z; and $Y_3$ includes a radical of Y). Such a composition can be used, for example, to prepare a film that includes small molecules that have groups in common with a polymer formed by reacting the monomer mixture. The similar groups between the two small molecules and the similar groups between the small molecules and the polymer can enhance the compatibility of the composition.

In a first variation of the fourteenth embodiment, the first aromatic core or the radical in the second compound can contain a substituent that is lacking in the other moiety. In a second variation, both the first aromatic core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms. In a third variation, either the first end capping group or the corresponding monovalent radical in the first monomer of the monomer mixture can contain a substituents that are lacking in the other moiety. In a fourth variation, both the first end capping group and the corresponding monovalent radical in the first monomer can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms. In a fifth variation, either the second end capping group or the corresponding monovalent radical in the second monomer of the monomer mixture can contain a substituent that is lacking in the other moiety. In another variation, both the second end capping group and the corresponding monovalent radical in the second monomer can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

The above embodiments provide examples where the first compound has identical end capping groups. Similar examples include those in which the first compound has non-identical end capping groups and the second compound has structural similarities to at least one of the end capping groups.

The above embodiments provide examples where the second compound has two end capping groups. Similar examples include those in which the second compound has only one end capping group or more than two end capping groups.

The above embodiments provide examples where the second compound has identical end capping groups. The end capping groups of the second compound can be the same or different from each other. Similar examples include those in which at least one of the end capping groups has structural similarities to the first compound.

Organic Electronic Devices

In another aspect, the present invention provides organic electronic devices that include a compound of Formula I or compositions that include a compound of Formula I. Organic electronic devices are articles that include layers of organic materials, at least one of which can conduct an electric current. Examples of organic electronic devices that can be made using the compounds or compositions of this invention include organic transistors and diodes, photovoltaic devices, organic electroluminescent (OEL) devices such as organic light emitting diodes (OLEDs), and the like.

The organic electronic device can be an organic electroluminescent display or device. As used herein, "organic electroluminescent (OEL) displays or devices" refer to displays or devices that include an organic light emitting material sandwiched between an anode and a cathode. The light emitting material can be a small molecule (SM) emitter, a SM doped polymer, a light emitting polymer (LEP), a doped LEP, a blended LEP, or another organic emissive material that can be provided alone or in combination with any other organic or inorganic materials that are functional or non-functional in the OEL display or devices. The organic electroluminescent displays or devices have potential use in applications such as backlighting of graphics, pixelated displays, and large emissive graphics.

R. H. Friend et al. in "Electroluminescence in Conjugated Polymers," *Nature*, 397, 121 (1999), incorporated herein by reference, describe one mechanism of electroluminescence as including the "injection of electrons from one electrode and holes from the other, the capture of oppositely charged carriers (so-called recombination), and the radiative decay of the excited electron-hole state (exciton) produced by this recombination process."

The organic electroluminescent device includes an organic emissive element. The organic emissive element includes a thin layer, or layers, of one or more suitable organic materials sandwiched between a cathode and an anode. The organic emissive element typically provides electron transport and hole transport as well as light emission. When activated, electrons are injected into the organic emissive element from the cathode and holes are injected into the organic emissive element from the anode. Electrons reside in the organic emissive element as radical anions and holes as radical cations. As the injected charges migrate towards the oppositely charged electrodes, they may recombine to form electron-hole pairs that are typically referred to as excitons. The region of the device in which the excitons are generally formed can be; referred to as the recombination zone. These excitons, or excited state species, can emit energy in the form of light as they decay back to a ground state.

The organic emissive element typically includes a light emitting layer. The light emitting layer includes a light emitting material such as a light emitting polymer or a light emitting small molecule. The light emitting layer optionally includes other materials, such as, for example, hole transport material, electron transport material, binder, polymeric binder, wave guiding particles, phosphorescent compounds, and color conversion materials. In some embodiments, the light emitting layer includes a compound according to Formula I. For example, the light emitting layer can include a compound according to Formula I as well as a second compound that is a light emitting material, a charge transporting material, a charge blocking material, a color conversion material, a polymeric binder, or a combination thereof.

Other layers can also be present in organic emissive element such as hole transport layers, electron transport layers, hole injection layer, electron injection layers, hole blocking layers, electron blocking layers, buffer layers, and the like. In addition, photoluminescent materials can be present in the light emitting layer or other layers in OEL devices, for example, to convert the color of light emitted by the electroluminescent material to another color. These and other such layers and materials can be used to alter or tune the electronic properties and behavior of the layered OEL device, for example to achieve a desired current/voltage response, a desired device efficiency, a desired color, a desired brightness, and the like. In some embodiments, a compound according to Formula I can be included in these other layers of the light emissive element. In other embodiments, at least one of these other layers includes a compound according to Formula I as well as a second compound that is a light emitting material, a charge transporting material, a charge blocking material, a color conversion material, a polymeric binder, or a combination thereof. For example, the compounds or compositions of the invention can be included in the electron transport layer, the hole transport layer, or a combination thereof.

In some embodiments, the light emitting molecule included in the organic emissive element of an organic electroluminescent device can be a molecularly doped polymer where charge carrying and/or emitting species are dispersed in a polymer matrix (see J. Kido, "Organic Electroluminescent devices Based on Polymeric Materials," *Trends in Polymer Science*, 2, 350-355 (1994)); a conjugated polymer or light emitting polymer (LEP) where layers of polymers such as poly(phenylenevinylene) act as the. charge carrying and emitting species (see J. J. M. Halls, D. R. Baigent, F. Cacialli, N. C. Greenham, R. H. Friend, S. C. Moratti, and A. B. Holmes, "Light-emitting and Photoconductive Diodes Fabricated with Conjugated Polymers," *Thin Solid Films*, 276, 13-20 (1996)); a vapor deposited small molecule heterostructure (see U. S. Pat. No. 5,061,569, incorporated by reference, and C. H. Chen, J. Shi, and C. W. Tang, "Recent Developments in Molecular Organic Electroluminescent Materials," *Macromolecular Symposia*, 125, 1-48 (1997)); or various combinations of these elements.

Other examples of OLEDs include light emitting electrochemical cells (see Q. Pei, Y. Yang, G. Yu, C. Zang, and A. J. Heeger, "Polymer Light-Emitting Electrochemical Cells: In Situ Formation of Light-Emitting p-n Junction," *Journal of the American Chemical Society*, 118, 3922-3929 (1996)) and vertically stacked organic light-emitting diodes capable of emitting light of multiple wavelengths (see U.S. Pat. No. 5,707,745, incorporated by reference, and Z. Shen, P. E. Burrows, V. Bulovic, S. R. Forrest, and M. E. Thompson, "Three-Color, Tunable, Organic Light-Emitting Devices," *Science*, 276, 2009-2011 (1997)).

A typical anode for an organic electroluminescent device is indium-tin-oxide (ITO) sputtered onto a transparent substrate such as plastic or glass. Suitable substrates include, for example, glass, transparent plastics such as polyolefins, polyethersulfones, polycarbonates, polyesters, polyarylates, and polymeric multilayer films, ITO coated barrier films such as the Plastic Film Conductor available from 3M Optical Systems Division, surface-treated films, and selected polyimides. In some embodiments, the substrate has barrier properties matching those of the protective (or counter electrode) film. Flexible rolls of glass may also be used. Such a material may be laminated to a polymer carrier for better structural integrity.

The anode material coating the substrate is electrically conductive and may be optically transparent or semi-transparent. In addition to ITO, suitable anode materials include indium oxide, fluorine tin oxide (FTO), zinc oxide, vanadium oxide, zinc-tin oxide, gold, platinum, palladium silver, other high work function metals, and combinations thereof. In practice, the anode is optionally coated with 10-200 Å of an ionic polymer such as PEDT or PANI to help planarize the surface and to modify the effective work function of the anode.

Typical cathodes include low work function metals such as aluminum, barium, calcium, samarium, magnesium, silver, magnesium/silver alloys, lithium, lithium fluoride, ytterbium, and alloys of calcium and magnesium.

As an example of a device structure, FIG. 1 illustrates an OEL display or device 100 that includes a device layer 110 and a substrate 120. Any other suitable display component can also be included with display 100. Optionally, additional optical elements or other devices suitable for use with electronic displays, devices, or lamps can be provided between display 100 and viewer position 140 as indicated by optional element 130.

In some embodiments like the one shown, device layer 110 includes one or more OEL devices that emit light through the substrate toward a viewer position 140. The viewer position 140 is used generically to indicate an intended destination for the emitted light whether it be an actual human observer, a screen, an optical component, an electronic device, or the like. In other embodiments (not shown), device layer 110 is positioned between substrate 120 and the viewer position 140. The device configuration shown in FIG. 1 (termed "bottom emitting") may be used when substrate 120 is transmissive to light emitted by device layer 110 and when a transparent conductive electrode is disposed in the device between the light emitting layer of the device and the substrate. The inverted configuration (termed "top emitting") may be used when substrate 120 does or does not transmit the light emitted by the device layer and the electrode disposed between the substrate and the light emitting layer of the device does not transmit the light emitted by the device.

Device layer 110 can include one or more OEL devices arranged in any suitable manner. For example, in lamp applications (e.g., backlights for liquid crystal display (LCD) modules), device layer 110 might constitute a single OEL device that spans an entire intended backlight area. Alternatively, in other lamp applications, device layer 110 might constitute a plurality of closely spaced devices that can be contemporaneously activated. For example, relatively small and closely spaced red, green, and blue light emitters can be patterned between common electrodes so that device layer 110 appears to emit white light when the emitters are activated. Other arrangements for backlight applications are also contemplated.

In direct view or other display applications, it may be desirable for device layer 110 to include a plurality of independently addressable OEL devices or elements that emit the same or different colors. Each device might represent a separate pixel or a separate sub-pixel of a pixilated display (e.g., high resolution display), a separate segment or sub-segment of a segmented display (e.g., low information content display), or a separate icon, portion of an icon, or lamp for an icon (e.g., indicator applications).

Referring back to FIG. 1, device layer 110 is disposed on substrate 120. Substrate 120 can be any substrate suitable for OEL device and display applications. For example, substrate 120 can include glass, clear plastic, or other suitable material(s) that are substantially transparent to visible light. Substrate 120 can also be opaque to visible light, for example stainless steel, crystalline silicon, poly-silicon, or the like. Because some materials in OEL devices can be particularly susceptible to damage due to exposure to oxygen or water, substrate 120 preferably provides an adequate environmental barrier, or is supplied with one or more layers, coatings, or laminates that provide an adequate environmental barrier.

Substrate 120 can also include any number of devices or components suitable in OEL devices and displays such as transistor arrays and other electronic devices; color filters, polarizers, wave plates, diffusers, and other optical devices; insulators, barrier ribs, black matrix, mask work and other such components; and the like. Generally, one or more electrodes will be coated, deposited, patterned, or otherwise disposed on substrate 120 before forming the remaining layer or layers of the OEL device or devices of the device layer 110. When a light transmissive substrate 120 is used and the OEL device or devices are bottom emitting, the electrode or electrodes that are disposed between the substrate 120 and the emissive material(s) are preferably substantially transparent to light, for example transparent conductive electrodes such as indium tin oxide (ITO) or any of a number of other transparent conductive oxides.

Element 130 can be any element or combination of elements suitable for use with OEL display or device 100. For example, element 130 can be a LCD module when device 100 is a backlight. One or more polarizers or other elements can be provided between the LCD module and the backlight device 100, for instance an absorbing or reflective clean-up polarizer. Alternatively, when device 100 is itself an information display, element 130 can include one or more of polarizers, wave plates, touch panels, antireflective coatings, anti-smudge coatings, projection screens, brightness enhancement films, or other optical components, coatings, user interface devices, or the like.

FIGS. 4A to 4D illustrate examples of different OEL device (for example, an organic light emitting diode) configurations of the present invention. Each configuration includes a substrate 250, an anode 252, a cathode 254, and a light emitting layer 256. The light emitting layer 256 can include a compound of Formula I or a composition containing a compound of Formula I in combination with a second compound that is a charge transporting material, a charge blocking material, a light emitting material, a color conversion material, a polymeric binder, or a combination thereof. The configurations of FIGS. 4C and 4D also include a hole transport layer 258 and the configurations of FIGS. 4B and 4D include an electron transport layer 260. These layers conduct holes from the anode or electrons from the cathode, respectively. The compounds and compositions of the present invention can be included in one or both of these layers. In some embodiments, the OEL devices of FIGS. 4B-4D include a compound or composition of the invention in one or both of the light emitting layer 256 and the electron transport layer 260.

The anode 252 and cathode 254 are typically formed using conducting materials such as metals, alloys, metallic compounds, metal oxides, conductive ceramics, conductive dispersions, and conductive polymers, including, for example, gold, platinum, palladium, aluminum, calcium, titanium, titanium nitride, indium tin oxide (ITO), fluorine tin oxide (FTO), and polyaniline. The anode 252 and the cathode 254 can be single layers of conducting materials or they can include multiple layers. For example, an anode or a cathode may include a layer of aluminum and a layer of gold, a layer of calcium and a layer of aluminum, a layer of aluminum and a layer of lithium fluoride, or a metal layer and a conductive organic layer.

The hole transport layer 258 facilitates the injection of holes from the anode into the device and their migration towards the recombination zone. The hole transport layer 258 can further act as a barrier for the passage of electrons to the anode 252. In some examples, the hole transport layer 258 can include, for example, a diamine derivative, such as N,N'-bis(3-methylphenyl)-N,N'-bis(phenyl)benzidine (also known as TPD) or N,N'-bis(I-naphthyl)-N,N'-bis(phenyl) benzidine (NPB), or a triarylamine derivative, such as, 4,4',4"-Tris(N,N-diphenylamino)triphenylamine (TDATA) or 4,4',4"-Tris(N-3-methylphenyl-N-phenylamino)triphenylamine (mTDATA). Other examples of materials that can be in the hole transport layer include copper phthalocyanine (CuPC); 1,3,5-Tris(4-diphenylaminophenyl)benzenes (TDAPBs); and other compounds such as those described in H. Fujikawa, et al., *Synthetic Metals,* 91, 161 (1997) and J. V. Grazulevicius, P. Strohriegl, "Charge-Transporting Polymers and Molecular Glasses", *Handbook of Advanced Electronic and Photonic Materials and Devices*, H. S. Nalwa (ed.), 10, 233-274 (2001), both of which are incorporated herein by reference.

The electron transport layer 260 facilitates the injection of electrons and their migration towards the recombination zone. The electron transport layer 260 can further act as a barrier for the passage of holes to the cathode 254, if desired. In some examples, the electron transport layer 260 can be formed using the organometallic compound tris(8-hydroxyquinolato) aluminum (Alq3). Other examples of electron transport materials useful in electron transport layer 260 include 1,3-bis[5-(4-(1,1-dimethylethyl)phenyl)-1,3,4-oxadiazol-2-yl ]benzene, 2-(biphenyl-4-yl)-5-(4-(1,1-dimethylethyl)phenyl)-1,3,4-oxadiazole (tBuPBD) and other compounds described in C. H. Chen et al., *Macromol. Symp.,* 125, 1 (1997) and J. V. Grazulevicius et al., "Charge-Transporting Polymers and Molecular Glasses", *Handbook of Advanced Electronic and Photonic Materials and Devices*, H. S. Nalwa (ed.), 10, 233 (2001), both of which are incorporated herein by reference.

Figure 3:
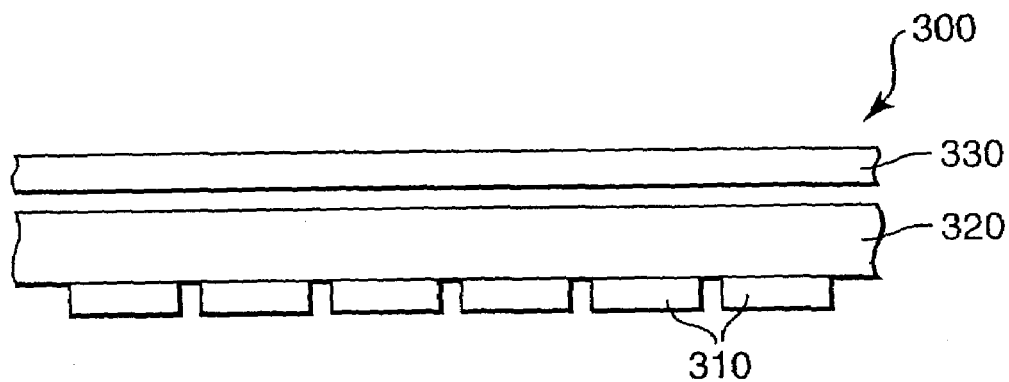
FIG. 3 is a schematic side view of an organic electroluminescent display.
Figure 4A:
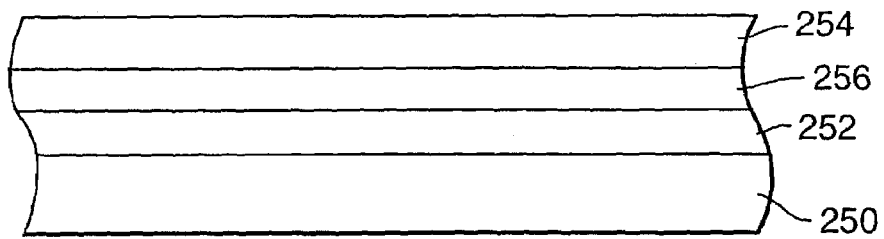
FIG. 4A is a schematic side view of a first embodiment of an organic electroluminescent device.
Figure 4B:
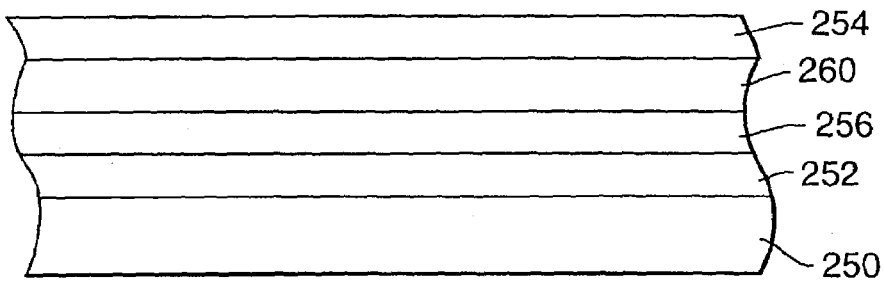
FIG. 4B is a schematic side view of a second embodiment of an organic electroluminescent device.
Figure 4C:
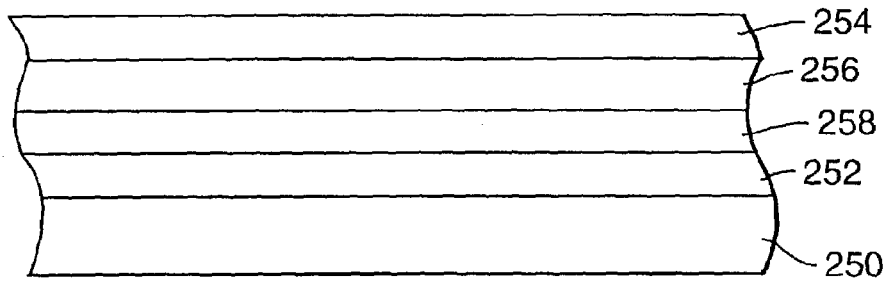
FIG. 4C is a schematic side view of a third embodiment of an organic electroluminescent device.
Figure 4D:
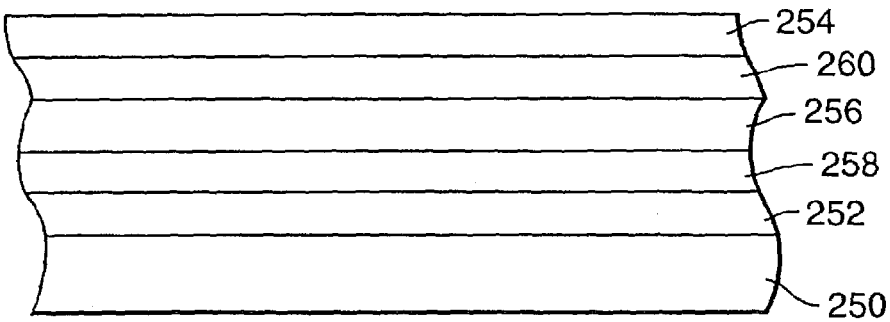
FIG. 4D is a schematic side view of a fourth embodiment of an organic electroluminescent device.

The present invention contemplates light emitting OEL displays and devices that include a compound according to Formula I or a composition that includes a compound according to Formula I in addition to a second compound that is a charge transporting material, a charge blocking material, a light emitting material, a color conversion material, a polymeric binder, or a combination thereof. In one embodiment, OEL displays can be made that emit light and that have adjacent devices or elements that can emit light having different color. For example, FIG. 3 shows an OEL display 300 that includes a plurality of OEL elements 310 adjacent to each other and disposed on a substrate 320. Two or more adjacent elements 310 can be made to emit different colors of light, for example red, green, and blue. One or more of elements 310 include a compound or composition of the present invention.

The separation shown between elements 310 is for illustrative purposes only. Adjacent devices may be separated, in contact, overlapping, etc., or different combinations of these in more than one direction on the display substrate. For example, a pattern of parallel striped transparent conductive anodes can be formed on the substrate followed by a striped pattern of a hole transport material and a striped repeating pattern of red, green, and blue light emitting LEP layers, followed by a striped pattern of cathodes, the cathode stripes oriented perpendicular to the anode stripes. Such a construction may be suitable for forming passive matrix displays. In other embodiments, transparent conductive anode pads can be provided in a two-dimensional pattern on the substrate and associated with addressing electronics such as one or more transistors, capacitors, etc., such as are suitable for making active matrix displays. Other layers, including the light emitting layer(s) can then be coated or deposited as a single layer or can be patterned (e.g., parallel stripes, two-dimensional pattern commensurate with the anodes, etc.) over the anodes or electronic devices. Any other suitable construction is also contemplated by the present invention.

In one embodiment, display 300 can be a multiple color display. In exemplary embodiments, each of the elements 310 emits light. There are many displays and devices constructions covered by the general construction illustrated in FIG. 3. Some of those constructions are discussed as follows.

Constructions of OEL backlights can include bare or circuitized substrates, anodes, cathodes, hole transport layers, electron transport layers, hole injection layers, electron injection layers, emissive layers, color changing layers, and other layers and materials suitable in OEL devices. Constructions can also include polarizers, diffusers, light guides, lenses, light control films, brightness enhancement films, and the like. Applications include white or single color large area single pixel lamps, for example where an emissive material is provided by thermal stamp transfer, lamination transfer, resistive head thermal printing, or the like; white or single color large area single electrode pair lamps that have a large number of closely spaced emissive layers patterned by laser induced thermal transfer; and tunable color multiple electrode large area lamps.

Constructions of low resolution OEL displays can include bare or circuitized substrates, anodes, cathodes, hole transport layers, electron transport layers, hole injection layers, electron injection layers, emissive layers, color changing layers, and other layers and materials suitable in OEL devices. Constructions can also include polarizers, diffusers, light guides, lenses, light control films, brightness enhancement films, and the like. Applications include graphic indicator lamps (e.g., icons); segmented alphanumeric displays (e.g., appliance time indicators); small monochrome passive or active matrix displays; small monochrome passive or active matrix displays plus graphic indicator lamps as part of an integrated display (e.g., cell phone displays); large area pixel display tiles (e.g., a plurality of modules, or tiles, each having a relatively small number of pixels), such as may be suitable for outdoor display used; and security display applications.

Constructions of high resolution OEL displays can include bare or circuitized substrates, anodes, cathodes, hole transport layers, electron transport layers, hole injection layers, electron injection layers, emissive layers, color changing layers, and other layers and materials suitable in OEL devices. Constructions can also include polarizers, diffusers, light guides, lenses, light control films, brightness enhancement films, and the like. Applications include active or passive matrix multicolor or full color displays; active or passive matrix multicolor or full color displays plus segmented or graphic indicator lamps (e.g., laser induced transfer of high resolution devices plus thermal hot stamp of icons on the same substrate); and security display applications. One particularly useful embodiment for this type of thermally patterned construction includes the high resolution transfer of red, green and blue emitting emissive layers onto a common substrate. High resolution transfer means that the rms (root mean square) edge roughness of the transferred material is 5 micrometers or less.

Methods for Fabricating OEL Layers

Another aspect of the invention provides a method for preparing organic electroluminescent devices. The devices include an organic emissive structure that includes a compound of Formula I or a composition that includes a compound of Formula I in addition to a second compound that is a light emitting material, a charge transporting material, a charge blocking material, a color conversion material, a polymeric binder, or a combination thereof.

In certain applications, it is desirable to pattern one or more layers of an organic electronic device onto a substrate, for example, to fabricate emissive displays. Methods for patterning include selective transfer, for example laser thermal transfer, photolithographic patterning, inkjet printing, screen printing, and the like.

One aspect of the present invention provides methods for making an organic electronic device. A donor sheet is prepared that has a transfer layer. The transfer layer includes a compound according to Formula I or a composition containing a compound according to Formula I and a second compound that is a light emitting material, a charge transporting material, a charge blocking material, a color conversion material, a polymeric binder, or a combination thereof. The method of preparing an organic electronic device includes preparing a donor sheet having a transfer layer and transferring the transfer layer from the donor layer to a receptor sheet.

A particularly useful method of forming organic electronic devices of the present invention, for example, organic electroluminescent devices, includes transferring one or more transfer layers by laser thermal patterning. This method is described in, for example, U.S. Pat. Nos. 6,358,664; 6,284,425; 6,242,152; 6,228,555; 6,228,543; 6,221,553; 6,221,543; 6,214,520; 6,194,119; 6,114,088; 5,998,085; 5,725,989; 5,710,097; 5,695,907; 5,693,446; 6,485,884; 6,521,324; WO02/22374; and U.S. Patent Publication Nos. 2003-0068525 and 2003-0124265, all of which are incorporated herein by reference. The effectiveness of the patterning process can depend upon the physical properties of the transfer layer.

One parameter is the cohesive, or film strength, of the transfer layer. During imaging, the transfer layer preferably breaks cleanly along the line dividing imaged and unimaged regions to form the edge of a pattern. Highly conjugated polymers that exist in extended chain conformations, such as polyphenylenevinylenes, can have high tensile strengths and elastic moduli comparable to that of polyaramide fibers. In practice, clean edge formation during the laser thermal imaging of light emitting polymers can be challenging. The undesired consequence of poor edge formation is rough, torn, or ragged edges on the transferred pattern. Another parameter is the strength of the bond formed between the transfer layer and the receptor surface. This strength may be influenced by the solubility parameter compatibility of the transfer layer and the receptor surface.

In some instances, it is desirable to select the material on the substrate surface and the material to be transferred (e.g., a compound or composition of the present invention) such that the solubility parameters are compatible to improve or even make possible thermal transfer or other patterning methods. As an example, the materials can be selected such that the difference in these solubility parameters is no more than 4 $J^{1/2}$ $cm^{-3/2}$ and, preferably, no more than 2 $J^{1/2}$ $cm^{-3/2}$ as determined according to *Properties of Polymers; Their Correlation with Chemical Structure; Their Numerical Estimation and Prediction from Additive Group Contributions*, third edition, edited by D. W. Van. Krevelen; Elsevier Science Publishers B. V., 1990; Chapter 7, pp 189-225, incorporated herein by reference.

The solubility parameter of a materials can be determined from measurements of the extent of equilibrium swelling of the material in a range of solvents of differing solubility parameters. The solubility parameters of the solvents themselves can be determined from their heats of evaporation. The solubility parameter $\delta$ is related to the cohesive energy $E_{coh}$ and the specific volume V by the relationship $\delta = (E_{coh}/V)^{1/2}$. For solvents of low molecular weight, the cohesive energy is closely related to the molar heat of evaporation $\Delta H_{vap}$ according to $E_{coh} = \Delta H_{vap} - p\Delta V = \Delta H_{vap} - RT$. Thus, $E_{coh}$ and $\delta$ can be calculated from the heat of evaporation of the solvent or from the course of the vapor pressure as a function of temperature.

Because some materials such as polymers cannot be evaporated, indirect methods have to be used for determination of their solubility parameter. To determine the solubility parameter of the polymer, the equilibrium swelling of the polymer in a variety of solvents of differing $\delta$ is measured and a plot of equilibrium swelling of the polymer vs. the solubility parameter of the solvents is generated. The solubility parameter of the polymer is defined as the point on this plot where maximum swelling is obtained. Swelling will be less for solvents having solubility parameters that are less than or greater than that of the polymer. There are several methods for theoretically estimating the solubility parameter of a polymer based on the additive contributions of functional groups present in the polymer as outlined in the above-cited reference.

Organic electronic devices containing a compound or composition of the present invention can be made at least in part by selective thermal transfer of the compound or composition from a thermal transfer donor sheet to a desired receptor substrate. For example, displays and lamps can be made by coating a light emitting layer on a donor sheet and then selectively transferring the light emitting layer alone or along with other device layers or materials to the display (receptor) substrate.

Figure 2:
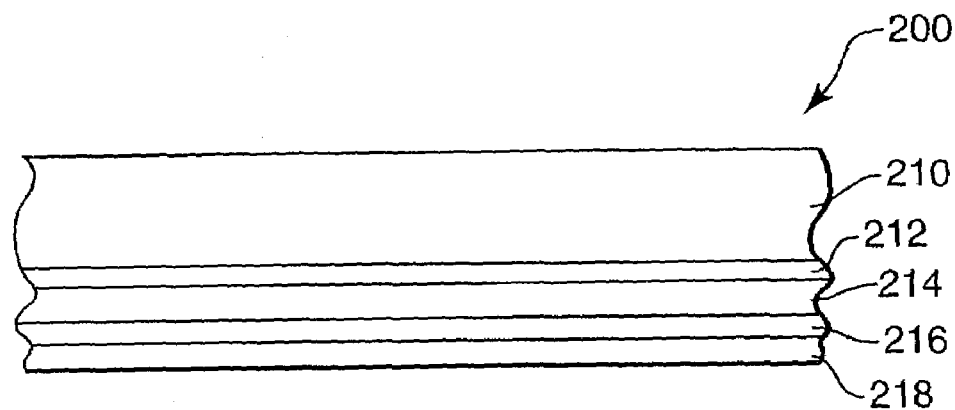
FIG. 2 is a schematic side view of a donor sheet for transferring materials.

FIG. 2 shows an example of a thermal transfer donor sheet 200 suitable for use in the present invention. Donor element 200 includes a base substrate 210, an optional underlayer 212, an optional light-to-heat conversion layer (LTHC layer) 214, an optional interlayer 216, and a transfer layer 218 comprising a compound according to Formula I or a composition that includes a compound according to Formula I in addition to a second compound that is a charge transporting material, a charge blocking material, a light emitting material, a color conversion material, a polymeric binder, or a combination thereof. Other compounds, compositions, or layers can also be present. Examples of suitable donors or layers of donors are disclosed in U.S. Pat. Nos. 6,358,664; 6,284,425; 6,242,152; 6,228,555; 6,228,543; 6,221,553; 6,221,543; 6,214,520; 6,194,119; 6,114,088; 5,998,085; 5,725,989; 5,710,097; 5,695,907; 5,693,446; 6,485,884;

6,521,324; WO02/22374; and U.S. Patent Publication Nos. 2003-0068525; and 2003-0124265, all of which are incorporated herein by reference.

Emissive organic materials, including LEPs or molecularly doped polymer films that include the compounds or compositions of this invention, can be transferred or selectively transferred in the transfer layer from a donor sheet to a receptor substrate by placing the transfer layer of the donor element adjacent to the receptor and selectively heating the donor element. Methods for the transfer or the selective transfer are described in, for example, U.S. Pat. No. 6,242,152. Transfer layers can also be transferred from donor sheets without selectively transferring the transfer layer. For example, a transfer layer can be formed on a donor substrate that, in essence, acts as a temporary liner that can be released after the transfer layer is contacted to a receptor substrate, typically with the application of heat or pressure. Such a method, referred to as lamination transfer, can be used to transfer the entire transfer layer, or a large portion thereof, to the receptor.

Materials from separate donor sheets can be transferred adjacent to other materials on a receptor to form adjacent devices, portions of adjacent devices, or different portions of the same device. Alternatively, materials from separate donor sheets can be transferred directly on top of, or in partial overlying registration with, other layers or materials previously patterned onto the receptor by thermal transfer or some other method (e.g., photolithography, deposition through a shadow mask, etc.). A variety of other combinations of two or more donor sheets can be used to form a device, each donor sheet forming one or more portions of the device. It will be understood that other portions of these devices, or other devices on the receptor, may be formed in whole or in part by any suitable process including photolithographic processes, ink jet processes, and various other printing or mask-based processes, whether conventionally used or newly developed.

In FIG. 2 the donor substrate 210 can be a polymer film. Suitable films are described in U.S. Pat. Nos. 6,242,152 and 6,228,555, incorporated herein by reference.

In FIG. 2 optional underlayer 212 may be coated or otherwise disposed between a donor substrate and the LTHC layer, for example to control heat flow between the substrate and the LTHC layer during imaging or to provide mechanical stability to the donor element for storage, handling, donor processing, or imaging. Examples of suitable underlayers and methods of providing underlayers are disclosed in U.S. Pat. No. 6,228,555 and in co-assigned U.S. patent application Ser No. 09/743,114, incorporated herein by reference.

The underlayer can include materials that impart desired mechanical or thermal properties to the donor element. For example, the underlayer can include materials that exhibit a low specific heat×density or low thermal conductivity relative to the donor substrate. Such an underlayer may be used to increase heat flow to the transfer layer, for example to improve the imaging sensitivity of the donor.

The underlayer may also include materials for their mechanical properties or for adhesion between the substrate and the LTHC. Using an underlayer that improves adhesion between the substrate and the LTHC layer may result in less distortion in the transferred image. As an example, in some cases an underlayer can be used that reduces or eliminates delamination or separation of the LTHC layer that might otherwise occur during imaging of the donor media. This can reduce the amount of physical distortion exhibited by transferred portions of the transfer layer. In other cases, however it may be desirable to employ underlayers that promote at least some degree of separation between or among layers during imaging, for example to produce an air gap between layers during imaging that can provide a thermal insulating function. Separation during imaging may also provide a channel for the release of gases that may be generated by heating of the LTHC layer during imaging. Providing such a channel may lead to fewer imaging defects.

The underlayer may be substantially transparent at the imaging wavelength, or may also be at least partially absorptive or reflective of imaging radiation. Attenuation or reflection of imaging radiation by the underlayer may be used to control heat generation during imaging.

In FIG. 2, an LTHC layer 214 can be included in donor sheets of the present invention to couple irradiation energy into the donor sheet. The LTHC layer preferably includes a radiation absorber that absorbs incident radiation (e.g., laser light) and converts at least a portion of the incident radiation into heat to enable transfer of the transfer layer from the donor sheet to the receptor. Suitable LTHC layers are described in, for example, U.S. Pat. Nos. 6,242,152, and 6,228,555, incorporated herein by reference.

In FIG. 2, an optional interlayer 216 may be disposed between the LTHC layer 214 and transfer layer 218. The interlayer can be used, for example, to minimize damage and contamination of the transferred portion of the transfer layer and may also reduce distortion in the transferred portion of the transfer layer. The interlayer may also influence the adhesion of the transfer layer to the rest of the donor sheet. Typically, the interlayer has high thermal resistance. Preferably, the interlayer does not distort or chemically decompose under the imaging conditions, particularly to an extent that renders the transferred image non-functional. The interlayer typically remains in contact with the LTHC layer during the transfer process and is not substantially transferred with the transfer layer. Suitable interlayers are described in, for example, U.S. Pat. Nos. 6,242,152 and 6,228,555, incorporated herein by reference.

In FIG. 2, a thermal transfer layer 218 is included in donor sheet 200. Transfer layer 218 includes a compound or composition of the present invention and can include any other suitable material or materials, disposed in one or more layers, alone or in combination with other materials. Transfer layer 218 is capable of being selectively transferred as a unit or in portions by any suitable transfer mechanism when the donor element is exposed to direct heating or to imaging radiation that can be absorbed by light-to-heat converter material and converted into heat.

The present invention further provides a light emitting transfer layer that includes a compound of Formula I or a composition that includes a compound of Formula I in addition to a second compound that is a light emitting material, a charge transporting material, a charge blocking material, a color conversion material, a polymeric binder, or a combination thereof. One way of providing the transfer layer is by solution coating the light emitting material onto the donor substrate or any of the layers described supra, i.e., underlayer, interlayer, light-to-heat converting layer. In this method, the light emitting material can be solubilized by addition of a suitable compatible solvent, and coated onto the donor substrate or any one of the above layers by spin-coating, gravure coating, Mayer rod coating, knife coating and the like. The solvent chosen preferably does not undesirably interact with (e.g., swell or dissolve) any of the already existing layers in the donor sheet. The coating can then be annealed and the solvent evaporated to leave a transfer layer.

The transfer layer can then be selectively thermally transferred from the resulting donor sheet or element to a proximately located receptor substrate. There can be, if desired, more than one transfer layer so that a multilayer construction is transferred using a single donor sheet. Suitable receptor substrates are described, for example, in U.S. Pat. Nos. 6,242,152 and 6,228,555, incorporated herein by reference.

Receptor substrates can be pre-patterned with any one or more of electrodes, transistors, capacitors, insulator ribs, spacers, color filters, black matrix, hole transport layers, electron transport layers, and other elements useful for electronic displays or other devices.

The invention is further described by the following examples, which are provided for illustration only and are not intended to be limiting in any way.

EXAMPLES

Examples 1-23 describe the synthesis of compounds of the invention and intermediates used in making them. All reagents were purchased from Aldrich Chemical Company unless other wise specified. All compounds were characterized by $^1$H-NMR and found to correspond to the structures shown.

Glossary

CBP—a hole transporting agent, 4,4'-bis(carbazol-9-yl) biphenyl, available from H. W. Sands, Jupiter, Fla.

C80—Phenyl end capped polymer derived from the polymerization of 2-(2,5-dichloro phenyl)-5-[4-(octyloxy)phenyl]-1,3,4-oxadiazole. The synthesis of 2-(2,5-dichloro phenyl)-5-[4-(octyloxy)phenyl]-1,3,4-oxadiazole is described in Example 1. This material was polymerized and end capped as follows.

Into a flask fitted with a septum and nitrogen purge was introduced 4.10 g (9.77 mmol) of 2-(2,5-dichlorophenyl)-5-[4-(octyloxy)phenyl]-1,3,4-oxadiazole from Example 1, 2.85 g (10.89 mmol) of triphenylphosphine, and 0.31 g (1.421 mmol) of anhydrous nickel (II) bromide. To this was added 75 ml dry DMF and 25 ml dry toluene. This was azeotroped with the use of a Dean-Stark condenser followed by distilling off much of the toluene. To the cooled reaction solution was added a further 0.31 g (1.421 mmol) of anhydrous nickel (II) bromide under a strong nitrogen purge. This was heated at 80° C. for 30 minutes followed by the addition of 1.0 g chlorobenzene as end-capping agent. The reaction was allowed to proceed for 8 hours at 80° C. The cooled reaction mixture was poured into about 500 ml acetone and filtered. The solid cake was taken up in methylene chloride and 1N HCl added and the two phase system stirred for about an hour. The resulting solids were filtered off and the filtrate transferred to a separatory funnel. The lower organic layer was separated and poured into an excess of methanol. The solid was collected, washed with methanol and dried to give 2.8 g of polymer.

GPC analysis gave a weight average molecular weight (Mw) of $1.7 \times 10^5$, a number average molecular weight (Mn) of $4.9 \times 10^4$, and a polydispersity (PD) of 3.55.

Ir(ppy)$_3$—a molecular emitter, tris(2-phenylpyridine) iridium (III), available from H. W. Sands, Jupiter, Fla.

PBD—An electron transport agent, 2-(4-biphenyl)-5-(4-t-butylphenyl)-1,3,4-oxadiazole, available from H. W. Sands, Jupiter, Fla.

PEDT/PSS—copolymer (poly(3,4-ethylenedioxythiophene)/polystyrene sulfonate, available as Baytron™ P4083 from Bayer A G, Leverkusen, Germany.

PVK—a hole transporting agent, poly(9-vinylcarbazole, available from Aldrich, Milwaukee, Wis.

Tetrakis(triphenylphosphine) palladium (0) was obtained from Strem Chemical, Newburyport, Mass.

TPD—A hole transporting agent, N,N'-bis(3-methylphenyl)-N,N'-bis(phenyl)benzidine, available from H. W. Sands, Jupiter, Fla.

Example 1

Synthesis of 2-(2,5-Dichlorophenyl)-5-[4-(octyloxy) phenyl]-1,3,4-oxadiazole

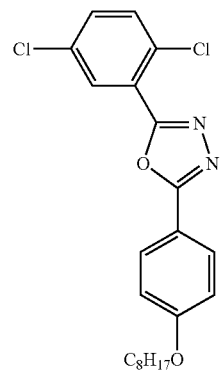

Part A: Synthesis of Methyl 4-octoxybenzoate

Into a flask was introduced 251.0 g (1.65 mol) of methyl 4-hydroxybenzoate, 276.37 g (1.99 mol) potassium carbonate and 1200 g of acetone. This was refluxed for 45 min followed by the dropwise addition of 386.17 g (1.99 mol ) of 1-octylbromide over a 1 hour period. The reaction mixture was refluxed for two days. Filtration of the cooled reaction mixture and evaporation of the filtrate gave an oil. This was taken up in ethyl acetate and extracted with 5% NaOH (2×100 ml) followed by water (2×100 ml). The organic layer was dried (MgSO$_4$), concentrated, and transferred to a 1 L three necked flask. The contents of the flask was subjected to high vacuum distillation to remove the excess 1-octylbromide. The pot residue was essentially pure methyl 4-octoxybenzoate (376 g, 86%).

Part B: Synthesis of 4-Octoxybenzoyl Hydrazide

To the contents of the flask from Part A was added 387.14 g of 98% hydrazine. This was refluxed for 5 hours (106° C.). The cooled solution was poured into 3 L of water and the precipitated solid filtered, washed with copious amounts of water and dried in a vacuum to give 4-octylbenzoyl hydrazide (343 g, 91% yield, mp 90° C.).

Part C: Synthesis of 2,4-Dichlorobenzoyl Chloride

Into a 2 L flask fitted with a reflux condenser and magnetic stir-bar was introduced 150 g (0.785 mol) 2,5-dichlorobenzoic acid and 575 ml (7.85 mol) of thionyl chloride. The mixture was refluxed for 8 hours. Most of the thionyl chloride was distilled off followed by removal of the remainder by rotary evaporation. Distillation gave 130 g (79% yield) of 2,4-dichlorobenzoyl chloride (pot temperature 110° C.; distillation temp 70° C./0.70 mm Hg).

Part D: Synthesis of 2,5-Dichloro-N'-[4-(octyloxy)benzoyl] benzohydrazide

Under a blanket of nitrogen, 8.8 g (0.087 mol) 2,4-dichlorobenzoyl chloride was added to a solution of 23.0 g (0.087 mol) 4-octoxybenzoyl hydrazine and 12.13 ml (8.8 g, 0.087 mol) freshly distilled triethylamine in 348 ml dry chloroform. After about one hour of stirring a dense white precipitate of the required product was formed. Stirring was continued until the next day. The product was collected by filtration and recrystallized from ethanol/water to give 31 g (81.5% yield) of 2,5-dichloro-N'-[4-(octyloxy)benzoyl]benzohydrazide as a white solid.

Part E: Synthesis of 2-(2,5-Dichlorophenyl)-5-[4-(octyloxy) phenyl]-1,3,4-oxadiazole Into a 250 ml flask fitted with a mechanical stirrer and thermometer was introduced 30 g (0.0686 mol) 2,5-dichlor-N'-[4-(octyloxy)benzoyl]benzohydrazide and 181 ml phosphorus oxychloride. This was refluxed and stirred for 8 hrs. About 100 ml of phosphorus oxychloride was distilled off under reduced pressure. The cooled residue was poured onto water and crushed ice with manual stirring and allowed to stand until the ice had melted. The precipitated white solid was collected by filtration, dried and recrystallized from ethanol. There was obtained 25.7 g (89% yield, mp 86° C.) of 2-(2,5-dichlorophenyl)-5-[4-(octyloxy)phenyl]-1,3,4-oxadiazole. The structure was confirmed unambiguously by 1D and 2D NMR techniques and gave the following:
$^1$H-NMR (500 MHz, CDCl$_3$) 0.89 (3H, t), 1.31 (8H, m), 1.46 (2H, q), 1.79 (2H, q), 6.97 (2H, d), 7.38 (1H, dd), 7.44 (1H, d), 8.01 (2H, d), 8.06 (1H, d); $^{13}$C-NMR (500 MHz, CDCl$_3$) 13.90, 22.44, 25.79, 28.91, 29.01, 29.13, 31.59, 68.08, 114.78, 115.37, 124.27, 128.58, 130.23, 130.87, 131.75, 132.20, 132.87, 161.03, 161.98, 164.95.

Example 2

Synthesis of 2-(4-tert-butylphenyl)-5-(2,5-dichlorophenyl)-1,3,4-oxadiazole

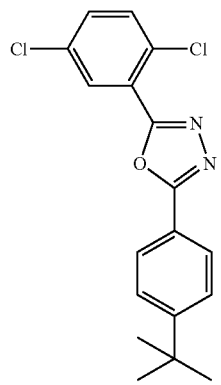

Part A: Synthesis of N-(4-tert-Butylbenzoyl)-2,5-dichlorobenzohydrazide 4-tert-Butylbenzoyl hydrazide (185 g, 0.96 mol) and triethylamine (97.37 g, 0.96 mol) freshly distilled from calcium hydride were added to 4 L of dichloromethane in a 10 L flask. To this was added with mechanical stirring 201.5 g of 2,4-dichlorobenzoyl chloride. No precipitation of the product was observed after three hours and the reaction was allowed to stir at room temperature until the next day. The product was precipitated by the addition of 4 L hexane. Filtration, hexane washing and drying at 80° C. in a forced air oven gave the product in 99% yield.

Part B: Synthesis of 2-(4-tert-butylphenyl)-5-(2,5-dichlorophenyl)-1,3,4-oxadiazole Into a 2 L flask was introduced 200 g N-(4-tert-butylbenzoyl)-2,5-dichlorobenzohydrazide (0.55 mol) and 1378 ml phosphorus oxychloride (2267 g, 14.78 mol). This was refluxed for 8 hrs and the solvent then evaporated under slight vacuum. The residue was poured onto crushed ice and allowed to stand until the next day. Filtration gave a sticky mass, which was dissolved in methanol, and solid material was obtained by addition of a little water. Filtration and drying gave 112 g of the product as a white crystalline solid (59% yield).

Example 3

Synthesis of 2-(2,5-Dibromophenyl)-5-[4-(octyloxy) phenyl]1,3,4-oxadiazole

This example describes the synthesis of 2-(2,5-dibromophenyl)-5-[4-(octyloxy)phenyl]1,3,4-oxadiazole and also provides a general method for preparing a range of useful aryl oxadiazole dibromide intermediates useful in Suzuki coupling reactions.

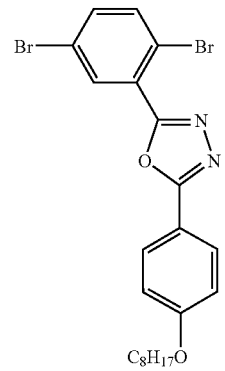

Part A: Synthesis of 2,5-Dibromobenzoyl Chloride

By the general method of Part C of Example 1, the reaction of 50.0 g (0.1786 mol) 2,5-dibromobenzoic acid with 150 mL thionyl chloride gave after distillation 40 g of 2,5-dibromobenzoyl chloride.

Part B: Synthesis of 2,5-Dibromo-N'-[4-(octyloxy)benzoyl] benzohydrazide

By the general method of Part A, Example 2,2,5-dibromobenzoyl chloride (57.43 g, 0.11925 mol), 4-octoxybenzoyl hydrazide (50.88 g, 0.1925 mol), and triethylamine (27 ml, 19.48 g, 0.1925 mol) were reacted in 800 ml methylene chloride to give a product. Re-crystallization of the product from DMF/water gave 79.38 g (78% yield) 2,5-dibromo-N'-[4-(octyloxy)benzoyl]benzohydrazide.

Part C: Synthesis of 2-(2,5-Dibromophenyl)-5-[4-(octyloxy) phenyl]1,3,4-oxadiazole By the general method of Part B of Example 2, cyclocondensation of 39.1 g (0.0743 mol) of N-(2,5-dibromobenzoyl)-4-(octyloxy)benzohydrazide with 203 ml phosphorus oxychloride for 8 hrs gave, after recrystallizing from EtOH/water, 33.6 g (89% yield) 2-(2,5-dibromophenyl)-5-[4-(octyloxy)phenyl]1,3,4-oxadiazole.

Example 4

Synthesis of 2-(2,5-Dichlorophenyl)-5-(pentafluorophenyl)-1,3,4-oxadiazole

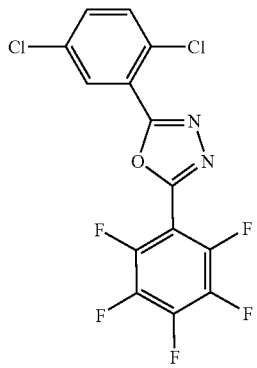

Part A: Synthesis of 2,5-Dichlorobenzohydrazide

Into a flask was introduced 30 g (0.1463 mol) methyl 2,5-dichlorobenzoate and 46.89 g (1.463 mol) hydrazine. This was refluxed for 5 hours. The cooled reaction mixture was poured into an excess of water, to precipitate an off-white solid. Filtration and drying under vacuum gave 30 g solid. A $^1$H-NMR showed that the material was fairly pure 2,5-dichlorobenzohydrazide and was therefore used without further purification.

Part B: Synthesis of 2,5-Dichloro-N'-(pentafluorobenzoyl)benzohydrazide

By the general method of Part A of Example 2, 21.0 g (0.1024 mol) 2,5-dichlorobenzohydrazide with 23.6 g (0.1024 mol) pentafluorobenzoyl chloride and 14.3 ml (0.1026 mol) triethylamine in methylene chloride/DMF (IL, 1: 1) gave, after re-crystallizing from DMF/water, 22.51 g (55% yield, mp 227-232° C.) 2,5-dichloro-N'-(pentafluorobenzoyl)benzohydrazide.

Part C: Synthesis of 2-(2,5-Dichlorophenyl)-5-(pentafluorophenyl)-1,3,4-oxadiazole By the general method of Part B of Example 2, the reaction of 21.0 g (0.05377 mol) 2,5-dichloro-N'-(pentafluorobenzoyl)benzohydrazide in POCl$_3$ gave a product which was recrystallized from ethanol/water to give 16.59 g (81% yield) of 2-(2,5-dichlorophenyl)-5-(pentafluorophenyl)-1,3,4-oxadiazole.

Example 5

Synthesis of 2-(2,5-Dichlorophenyl)-5-(9,9-dioctyl-9H-fluoren-2-yl)-1,3,4-oxadiazole

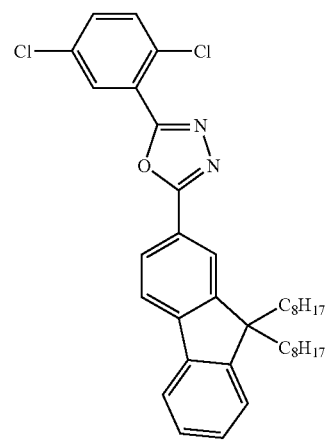

Part A: Synthesis of 2-Bromo-9,9-dioctylfluorene

A 3 L flask fitted with a mechanical stirrer was charged with 2-bromofluorene (45 g, 183.6 mmole) and 150 mL DMSO. Under a N$_2$ atmosphere was added 80 mL of a 50% aqueous NaOH solution and 2.72 g of benzyltriethylammonium chloride (2.72 g, 11.98 mmole). This was stirred for 2 h at RT. With vigorous mechanical stirring, n-octylbromide (84.96 g, 440 mmole) was added via a dropping funnel (exotherm). Stirring was continued for 2 hours. To the reaction mixture was added 500 mL of a 1:1 mixture of water/ether, and the organic layer separated and was washed successively with brine and then water. Drying over magnesium sulfate and evaporation of the solvent gave an oil. Purification by column chromatography (silica gel; hexane as the mobile phase) gave 67 g (78% yield) of 2-bromo-9,9-dioctylfluorene as a pale oil.

Part B: Synthesis of 9,9-Dioctyl-9H-fluorene-2-carboxylic Acid

Into a flask fitted with a nitrogen inlet and rubber septum were introduced 2-bromo-9,9-dioctylfluorene (34.18 g, 72.8 mmole) and dry tetrahydrofuran (300 mL). The solution was cooled to −60° C. and n-butyl lithium (29.1 mL, 2.5M in hexanes, 72.8 mmole) added via a syringe. The reaction mixture was observed to turn red. After stirring for 1 hour at −60° C., the reaction mixture was poured onto powdered dry-ice and left to stand overnight. The mixture was acidified with 1M HCl and extracted with chloroform. The chloroform extract was washed with water, dried over magnesium sulfate and concentrated to give the acid as an oil.

Part C: Synthesis of 9,9-Dioctyl-9H-fluorene-2-carbonyl Chloride 9,9-Dioctyl-9H-fluorene-2-carboxylic acid (32.36 g, 74.5 mmole) was refluxed in thionyl chloride (93 g, 782 mmole)

for 8 hrs. Unreacted thionyl chloride was distilled off and the residue material used without further purification.

Part D: Synthesis of 2,5-Dichloro-N'-[(9,9-dioctyl-9H-fluoren-2-yl)carbonyl]benzohydrazide 2,5-Dichlorobenzohydrazide (one equivalent) and triethylamine (one equivalent) were warmed in 500 mL of 1,2-dichloroethane until the solid material had dissolved. On cooling, 9,9-dioctyl-9H-fluorene-2-carbonyl chloride (one equivalent) was added and the mixture stirred at RT for two days. The insolubles were filtered off and the filtrate evaporated to give an oil. This was taken up in heptane and the precipitated solid filtered off. The remaining solution was dried (MgSO$_4$) and concentrated to give the desired intermediate.

Part E: Synthesis of 2-(2,5-Dichlorophenyl)-5-(9,9-dioctyl-9H-fluoren-2-yl)-1,3,4-oxadiazole 2,5-Dichloro-N'-[(9,9-dioctyl-9H-fluoren-2-yl)carbonyl]benzohydrazide (20.0 g, 32.17 mmole) and phosphorus oxychloride (91 mL) were refluxed for 8 hrs. The reaction was distilled until about half the volume remained. The pot fraction was cooled and poured onto an ice/water mixture with constant stirring. The sticky paste that formed was extracted into hexane and the hexane extract dried and concentrated. Column chromatography (5% ethyl acetate in hexane) gave 14.98 g (77% yield) of the desired compound as an oil.

Example 6

Synthesis of 2-(3,5-Dichlorophenyl)-5-[4-(octyloxy)phenyl]-1,3,4-oxadiazole

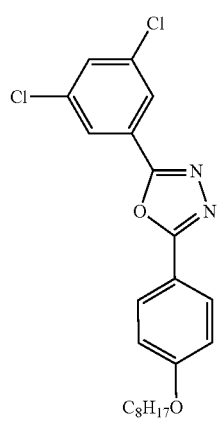

By the general method for the synthesis of 2-(2,5-dibromophenyl)-5-[4-(octyloxy)phenyl]-1,3,4-oxadiazole in Example 3, the reaction of 3,5-dichlorobenzoyl chloride (20.0 g, 0.010 mole) with 4-octoxybenzoyl hydrazide (25.24 g, 0.010 mole) gave the intermediate 3,5-dichloro-N'-[4-(octyloxy)benzoyl]benzohydrazide (25 g, 60% yield). Cyclocondensation of the intermediate 3,5-dichloro-N'-[4-(octyloxy)benzoyl]-benzohydrazide (16.0 g) with POCl$_3$ (83 mL) gave 2-(3,5-dichlorophenyl)-5-[4-(octyloxy)phenyl]-1,3,4-oxadiazole (11.16 g, 73% yield).

Example 7

Synthesis of 2-(3,5-Dibromophenyl)-5-[4-(octyloxy)phenyl]-1,3,4-oxadiazole

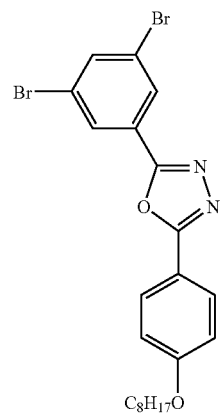

By the general method for the synthesis of 2-(2,5-dibromophenyl)-5-[4-(octyloxy)phenyl]-1,3,4-oxadiazole in Example 3, the reaction of 3,5-dibromobenzoyl chloride (20.13 g, 0.06747 mole) with 4-octoxybenzoyl hydrazide (17 g, 0.06747 mole) gave the intermediate 3,5-dibromo-N'-[4-(octyloxy)benzoyl]benzohydrazide (12.87 g, 36% yield). Cyclocondensation of the intermediate 3,5-dibromo-N'-[4-(oxtyloxy)benzoyl]-benzohydrazide (12.17 g) with POCl$_3$ (63 mL) gave 2-(3,5-dibromophenyl)-5-[4-(octyloxy)phenyl]-1,3,4-oxadiazole (6.12 g, 52% yield).

Example 8

Synthesis of 2-(3,5-dibromophenyl)-5-[3,5-bis(trifluoromethyl)phenyl]-1,3,4-oxadiazole

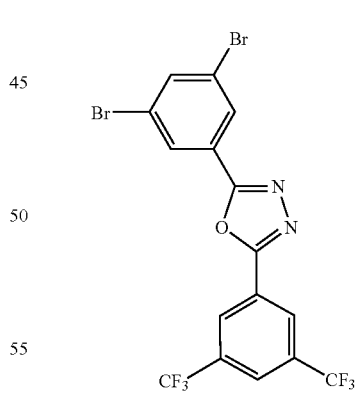

By the general method of Part B of Example 1, the reaction of methyl-3,5-bis(trifluoromethyl)benzoate with 98% hydrazine gave the intermediate 3,5-bis(trifluoromethyl)benzoyl hydrazide. By the general method of Part A of Example 2, the reaction of 3,5-dibromobenzoyl chloride with 3,5-bis(trifluoromethyl)benzoyl hydrazide in the presence of triethylamine gave the intermediate 3,5-dibromo-N'-[3,5-bis(trifluoromethyl)benzoyl]benzohydrazide. By the general method of Part B of Example 2, cyclocondensation of this intermediate with POCl₃ gives 2-(3,5-dibromophenyl)-5-[3,5-bis(trifluoromethyl)phenyl]-1,3,4-oxadiazole.

Example 9

Synthesis of 3-(2,5-Dichlorophenyl)-4-(4-methoxyphenyl)-5-[4-(octyloxy)phenyl]-4H-1,2,4-triazole

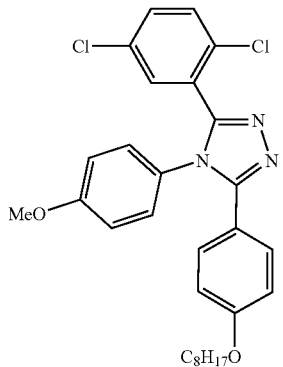

Into a 1 L round-bottomed flask fitted with a mechanical stirrer, reflux condenser and nitrogen inlet were introduced 2,5-dichloro-N'-[4-(octyloxy)benzoyl]benzohydrazide (40 g, 0.09146 mole, 1 equivalent), p-anisidine (67.60 g, 0.5487 mole, 6 equivalents) and 300 mL 1,2-dichlorobenzene. Mechanical stirring resulted in partial solvation of the solids. Phosphorus trichloride (12.56 g, 0.0146 mole, 1 equivalent) was added and the contents of the flask heated at 180° C. for 12 hrs. The solvent was distilled off under a light vacuum and the residue transferred to a 2 L flask with 1 L of a 1:1 acetone/heptane mixture. The solid material was filtered off and dissolved in acetone. Enough heptane was added to precipitate a purple-colored oily sludge. Heptane dilution of a test sample of the acetone/heptane layer ensured that the oily sludge had been completely precipitated. The acetone/heptane layer was decanted off and diluted further with a large excess of heptane to precipitate a white solid. This was filtered off, dissolved in acetone and re-precipitated with heptane. Filtration and drying gave 3-(2,5-dichlorophenyl)-4-(4-methoxyphenyl)-5-[4-(octyloxy)phenyl]-4H-1,2,4-triazole (16.25 g, 34% yield).

Example 10

Synthesis of 2-(3,5-bis(4,4,5,5-tetramethyl-1,3,2-dioxaborolan-2-yl)) phenyl)-5-[4-(octyloxy)phenyl]-1,3,4-oxadiazole This example describes the synthesis of 2-(3,5-bis(4,4,5,5-tetramethyl-1,3,2-dioxaborolan-2-yl)) phenyl)-5-[4-(octyloxy)phenyl]-1,3,4-oxadiazole and also provides a general method for preparing a range of useful aryl oxadiazole, triazole, and thiadiazole diboronic acid intermediates. The general procedure of arylboronic ester synthesis as reported in Ranger et al., *Chem. Commun.* 1597-1598 (1997) does not work well for this ring system due to side reactions of butyl lithium with the oxadiazole. Good conversion can be obtained using the general procedure for making arylboronic esters as described by Ishiyama, Murata, and Miyaura in *J. Org. Chem.* 1995, 60, 7508-7510.

Following this general procedure 2-(3,5-Dibromophenyl)-5-[4-(octyloxy)phenyl]-1,3,4-oxadiazole, bis(pinacolato)diboron, potassium acetate, and [1,1'-bis(diphenylphosphino)ferrocene]dichloropalladium (II) (complexed 1:1 with dichlormethane—Aldrich, 0.089 g, 0.1 mmoles) are reacted in DMSO under nitrogen at 80° C. for 18 hrs. After cooling, the reaction mixture is poured onto ice water, the aqueous layer extracted three times with methylene chloride, the combined organic fractions washed with brine, dried over magnesium sulfate, filtered through a thin silica bed, rotoevaporated to yield the desired 2-(3,5-bis(4,4,5,5-tetramethyl-1,3,2-dioxaborolan-2-yl)) phenyl)-5-[4-(octyloxy)phenyl]-1,3,4-oxadiazole. These general methods can be used to prepare a wide range of arylene oxadiazole, triazole and thiadiazole diboronic ester intermediates useful in preparing compounds of Formula 1.

Example 11

Synthesis of 2-(4-octyloxy-phenyl)-5-[1,1',4',1"]terphenyl-2'yl-[1,3,4]oxadiazole

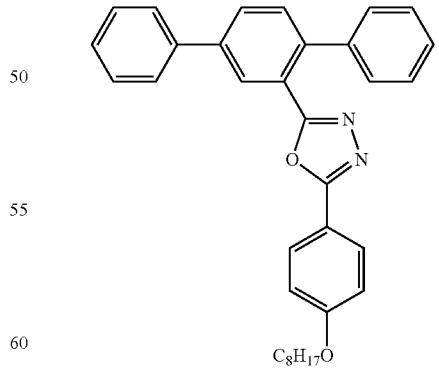

2-(2,5-dibromophenyl)-5-[4-(octyloxy)phenyl]1,3,4-oxadiazole (3.0 g) from Example 3, phenyl boronic acid (2.2 g, ), and NaHCO₃ (3.4 g, ) were mixed together with ethylene glycol dimethyl ether 60 mL and water 60 mL. The mixture was purged with nitrogen for an hour after which 0.35 g of (Ph$_3$P)$_4$Pd was added and the reaction was refluxed under nitrogen for 20 hours. After the reaction was cooled down, the aqueous layer was separated from the organic layer and washed with toluene. The combined organic layers were washed with water twice, then dried with Na$_2$SO$_4$. After the drying agent was filtered away, the organic layer was evaporated to dryness. The residue was recrystallized from ethanol 3 times to give a gray solid as the product (2.0 g, 67% yield).

Example 12

Synthesis of 2-[3,5-Bis-(9,9-dioctyl-9H-fluoren-2-yl)-phenyl]-5-(4-octyloxy-phenyl)-[1,3,4]oxadiazole

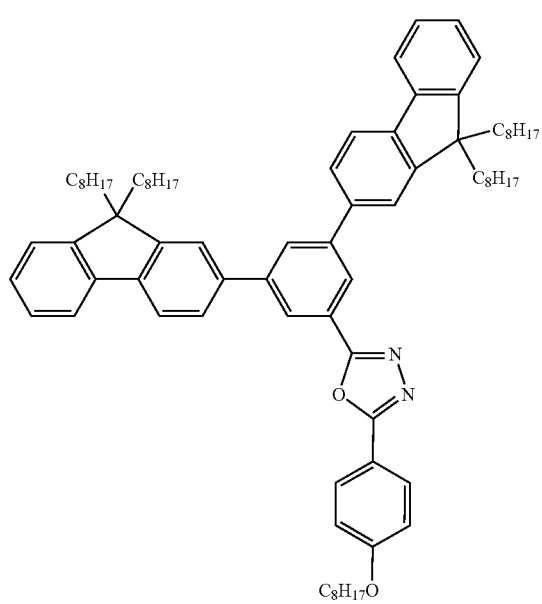

Part A: Synthesis of 2-(4,4,5,5-tetramethyl-1,3,2-dioxaborolan-2-yl)-9,9-dioctylfluorene.

2-(4,4,5,5-Tetramethyl-1,3,2-dioxaborolan-2-yl)-9,9-dioctylfluorene was synthesized from 2-bromo-9,9-dioctylfluorene (Part A of Example 5) by the general procedure of arylboronic ester synthesis as reported in Ranger et al., *Chem. Commun.* 1597-1598 (1997) and described in Example 19.

Part B: Synthesis of 2-[3,5-Bis-(9,9-dioctyl-9H-fluoren-2-yl)-phenyl]-5-(4-octyloxy-phenyl)-[1,3,4]oxadiazole Into a flask was introduced 2.8 mL of toluene, 2-(4,4,5,5-tetramethyl-1,3,2-dioxaborolan-2-yl)-9,9-dioctylfluorene (0.80 g, 1.5 mmol), 2-(3,5-dibromophenyl)-5-[4-(octyloxy)phenyl]-1,3,4-oxadiazole from Example 7 (0.375 g, 0.7 mmole), Aliqua™ 336 (0.15 g, 0.4 mmol) and 1.4 mL of aqueous 2M Na$_2$CO$_3$. This was N$_2$ purged for 1 h. The flask was heated to about 80° C. and tetrakistriphenylphosphine palladium (0) (12 mg, 0.01 mmol) then added under a nitrogen purge. The content of the flask was refluxed for 21 hrs. The reaction flask was allowed to cool to RT and about 5 mL water added and the organic layer separated. The aqueous layer was extracted with 3×15 mL ether. The organic layers were combined and washed successively with saturated NaCl twice and then dried over MgSO$_4$. Concentration gave an oil that was purified by flash chromatography (eluent: 10% ethyl acetate in hexane) and dried as an oil under vacuum for 30 minutes to give 0.59 grams of 2-[3,5-Bis-(9,9-dioctyl-9H-fluoren-2-yl)-phenyl]-5-(4-octyloxy-phenyl)-[1,3,4]oxadiazole.

Example 13

Synthesis of 2-[3,5-Bis-(9,9-dibutyl-9H-fluoren-2-yl)-phenyl]-5-(4-octyloxy-phenyl)-[1,3,4]oxadiazole

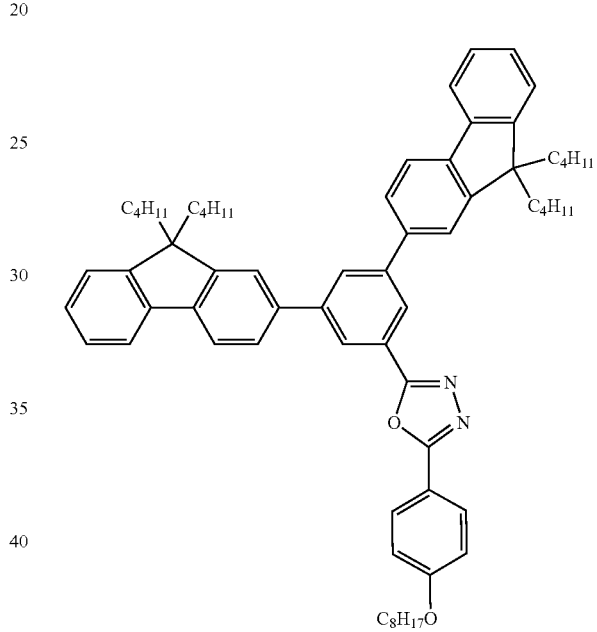

Part A: Synthesis of 2-Bromo-9,9-dibutylfluorene.

2-bromo-9,9-dibutylfluorene was synthesized from 2-bromofluorene and 1-bromobutane following the general procedures outlined in Part A of Example 5.

Part B: Synthesis of 2-(4,4,5,5-tetramethyl-1,3,2-dioxaborolan-2-yl)-9,9-dibutylfluorene 2-(4,4,5,5-tetramethyl-1,3,2-dioxaborolan-2-yl)-9,9-dibutylfluorene was synthesized from 2-bromo-9,9-dibutylfluorene by methods described in Part A of Example 12.

Part C: Synthesis of 2-[3,5-Bis-(9,9-dibutyl-9H-fluoren-2-yl)-phenyl]-5-(4-octyloxy-phenyl)-[1,3,4]oxadiazole Using procedures outlined in Part B of Example 12, 2-(4,4,5,5-tetramethyl-1,3,2-dioxaborolan-2-yl)-9,9-dibutylfluorene (1.88 g, 4.6 mmol) and 2-(3,5-dibromophenyl)-5-[4-(octyloxy)phenyl]-1,3,4-oxadiazole from Example 7 (1.13 g, 2.2 mmole) are reacted to give the corresponding 2-[3,5-Bis-(9,9-dibutyl-9H-fluoren-2-yl)-phenyl]-5-(4-octyloxy-phenyl)-[1,3,4]oxadiazole.

Example 14

Synthesis of 2-[3,5-Bis-(phenyl-4-yl-9H-carbazole)-phenyl]-5-(4-octyloxy-phenyl)-[1,3,4]oxadiazole

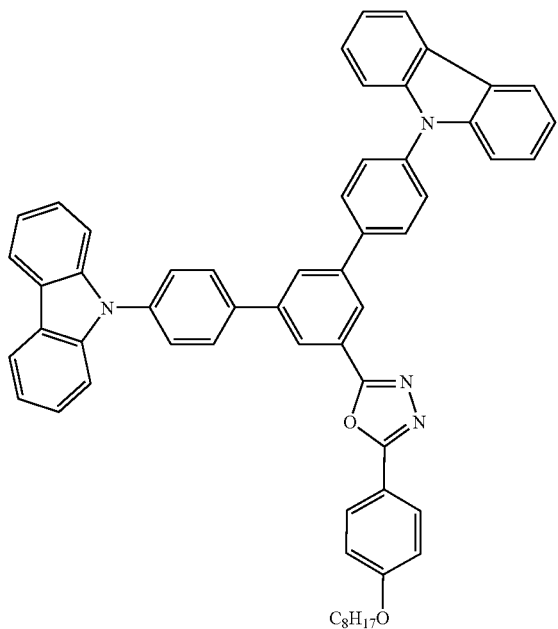

Part A: Synthesis of 4-bromophenyl-9H-carbazole

Following the general procedure for the ligand accelerated catalysis of Ullmann condensation as described by Goodbrand and Hu in *J. Org. Chem.* 1999, 64, 670-674, herein incorporated by reference, carbazole (14.77 g, 88.4 mmol), 1-bromo-4-iodobenzene (25.00 g, 88.4 mmol), 1,10-phenanthroline (0.6365 g, 3.3145 mmol), cuprous chloride (0.3128 g, 3.2145 mmol) and potassium carbonate (95.38 g, 691.12 mmol) were mixed with 70 mL of dry toluene. The solution was purged with nitrogen, heated to reflux under nitrogen for 82 hrs, cooled to room temperature, followed by water wash, filtration, drying over magnesium sulfate, and evaporation to dryness. Recrystallization from ethylacetate gave 18.5 grams of a 70:30 mixture of 4-bromophenylcarbazole and 4-iodophenylcarbazole, which was used without further purification.

Part B: Synthesis of 4-(4,4,5,5-tetramethyl-1,3,2-dioxaborolan-2-yl)-phenyl-9H-carbazole Following the general procedure for making arylboronic esters as described by Ishiyama, Murata, and Miyaura in *J. Org. Chem.* 1995, 60, 7508-7510, 4-bromophenyl-9H-carbazole (1.089 g, 3.3 mmoles), bis(pinacolato)diboron (0.922 g, 3.6 mmoles), potassium acetate (1.062 g, 11.0 mmoles), and [1,1'-bis(diphenylphosphino)-ferrocene]dichloropalladium (II) (complexed 1:1 with dichlormethane—Aldrich, 0.089 g, 0.1 mmoles) were mixed in 20 mL of DMSO. The solution was purged with nitrogen and heated under nitrogen at 80° C. for 18 hrs. After cooling, the reaction mixture was poured onto ice water, the aqueous layer extracted three times with methylene chloride, the combined organic fractions washed with brine, dried over magnesium sulfate, filtered through a thin silica bed, and rotoevaporated to yield 1.02 g of 4-(4,4,5,5-tetramethyl-1,3,2-dioxaborolan-2-yl)-phenyl-9H-carbazole (84% yield).

Part C: Synthesis of 2-[3,5-Bis-(phenyl-4-yl-9H-carbazole)-phenyl]-5-(4-octyloxy-phenyl)-[1,3,4]oxadiazole.

Into a flask was introduced 10 mL of toluene, 4-(4,4,5,5-tetramethyl-1,3,2-dioxaborolan-2-yl)-N-phenylcarbazole (2.0 g, 5.4 mmol), 2-(3,5-dibromophenyl)-5-[4-(octyloxy) phenyl]-1,3,4-oxadiazole from Example 7 (1.31 g, 2.6 mmole), Aliqua™ 336 (0.521 g, 1.3 mmol) and 5 mL of aqueous 2M $Na_2CO_3$. This was $N_2$ purged for 1 h. The flask was heated to about 80° C. and tetrakistriphenylphosphine palladium (0) (94 mg, 0.081 mmol) then added under a nitrogen purge. The content of the flask was refluxed for 21 hrs. The reaction flask was allowed to cool to RT and about 20 mL water added and the organic layer separated. The aqueous layer was extracted with 6×10 mL methylene chloride. The organic layers were combined and washed successively with saturated NaCl twice and then dried over $MgSO_4$. Concentration gave a solid that was purified by recrystallization from 50:50 methylene chloride:hexanes to give 1.3 g of 2-[3,5-Bis-(phenyl-4-yl-9H-carbazole)-phenyl]-5-(4-octyloxy-phenyl)-[1,3,4]oxadiazole.

Example 15

Synthesis of 2-[2,5-Bis-{9,9-bis-(3,6-dioxaheptyl)-9H-fluoren-2-yl}-phenyl]-5-(4-octyloxy-phenyl)-[1,3,4]oxadiazole

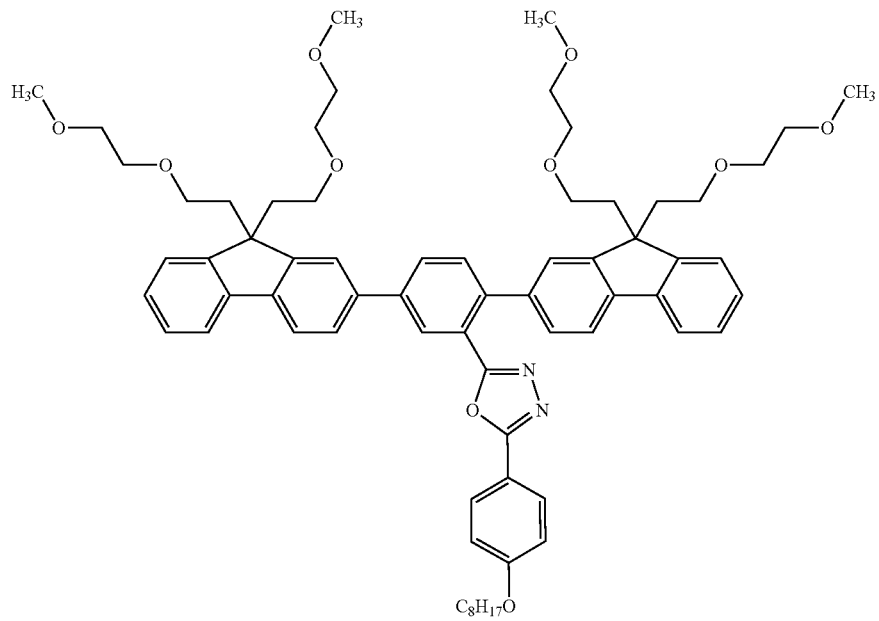

Part A: Synthesis of 2-bromo-9,9-bis(3,6-dioxaheptyl)-fluorene.

2-Bromo-9,9-bis(3,6-dioxaheptyl)-fluorene was synthesized from bromo-2-(2-methoxyethoxy)ethane and 2-bromofluorene by methods described in Part A of Example 5.

Part B: Synthesis of 2-(4,4,5,5-tetramethyl-1,3,2-dioxaborolan-2-yl)-9,9-bis(3,6-dioxaheptyl)-fluorene.

2-(4,4,5,5-tetramethyl-1,3,2-dioxaborolan-2-yl)-9,9-bis(3,6-dioxaheptyl)-fluorene was synthesized from 2-bromo-9,9-bis(3,6-dioxaheptyl)-fluorene by methods described in Part A of Example 12.

Part C: Synthesis of 2-[2,5-Bis-{9,9-bis-(3,6-dioxaheptyl)-9H-fluoren-2-yl}-phenyl]-5-(4-octyloxy-phenyl)-[1,3,4]oxadiazole.

Following the general procedures for Part B of Example 12, 2-[2,5-Bis-{9,9-bis-(3,6-dioxaheptyl)-9H-fluoren-2-yl}-phenyl]-5-(4-octyloxy-phenyl)-[1,3,4]oxadiazole is prepared by reaction of 2-bromo-9,9-bis(3,6-dioxaheptyl)-fluorene with 2-(2,5-dibromophenyl)-5-[4-(octyloxy)phenyl]-1,3,4-oxadiazole from Example 3. The resulting product can be shown to give rise to photoluminescence and to form films that can be thermally transferred to ionically conducting polymer films such as PEDT (poly(3,4-ethylenedioxythiophene); CH-8000 from Bayer A G, Leverkusen, Germany).

Example 16

Synthesis 2-[3,5-Bis-{9,9-dioctyl-7-(phenyl-4-amino-N,N-diphenyl)-9H-fluoren-2-yl}-phenyl]-5-(4-octyloxy-phenyl)-[1,3,4]oxadiazole Part A: Synthesis of 2,7-Dibromo-9,9-dioctyl-fluorene.

2,7-Dibromo-9,9-dioctyl-fluorene was made as described in Ranger et al., *Can. J. Chem.*, 1571-1577(1998), incorporated herein by reference.

Part B: Synthesis of 2-[9,9-dioctyl-7-(4,4,5,5-tetramethyl-1,3,2-dioxaborolan-2-yl)-9H-fluoren-2-yl]-4,4,5,5-tetramethyl-1,3,2-dioxaborolane.

2-[9,9-dioctyl-7-(4,4,5,5-tetramethyl-1,3,2-dioxaborolan-2-yl)-9H-fluoren-2-yl]-4,4,5,5-tetramethyl-1,3,2-dioxaborolane was made from 2,7-dibromo-9,9-dioctyl-fluorene as described in Ranger et al., *Chem. Commun.* 1597-1598 (1997), incorporated herein by reference.

Part C: Synthesis of 4-bromo-N,N-diphenylaniline

4-Bromo-N,N-diphenylaniline was made as described in Creason et al., *J. Org. Chem.* 37, 4440-4446 (1972), incorporated herein by reference.

Part D: Synthesis of 4-[9,9-Dioctyl-7-(4,4,5,5-tetramethyl-1,3,2-dioxaborolan-2-yl)-9H-fluoren-2-yl]-N,N-diphenylaniline 4-Bromo-N,N-diphenylaniline (19.44 g, 60 mmole), 2-[9,9-dioctyl-7-(4,4,5,5-tetramethyl-1,3,2-dioxaborolan-2-yl)-9H-fluoren-2-yl]-4,4,5,5-tetramethyl-1,3,2-dioxaborolane (76.9 g, 120 mmole), Aliquat™ 336 (tricaprylylmethylammonium chloride) (6 g, 15 mmole) and 2M sodium carbonate solution (75 mL, 150 mmole) were added to 600 mL of toluene. This was purged with a stream of nitrogen for about 30 min. Under a nitrogen purge, tetrakis(triphenylphosphine) palladium (0) (348 mg, 0.30 mmole) was added. The reaction mixture was then refluxed for 16 hrs. The reaction was cooled to room temperature and

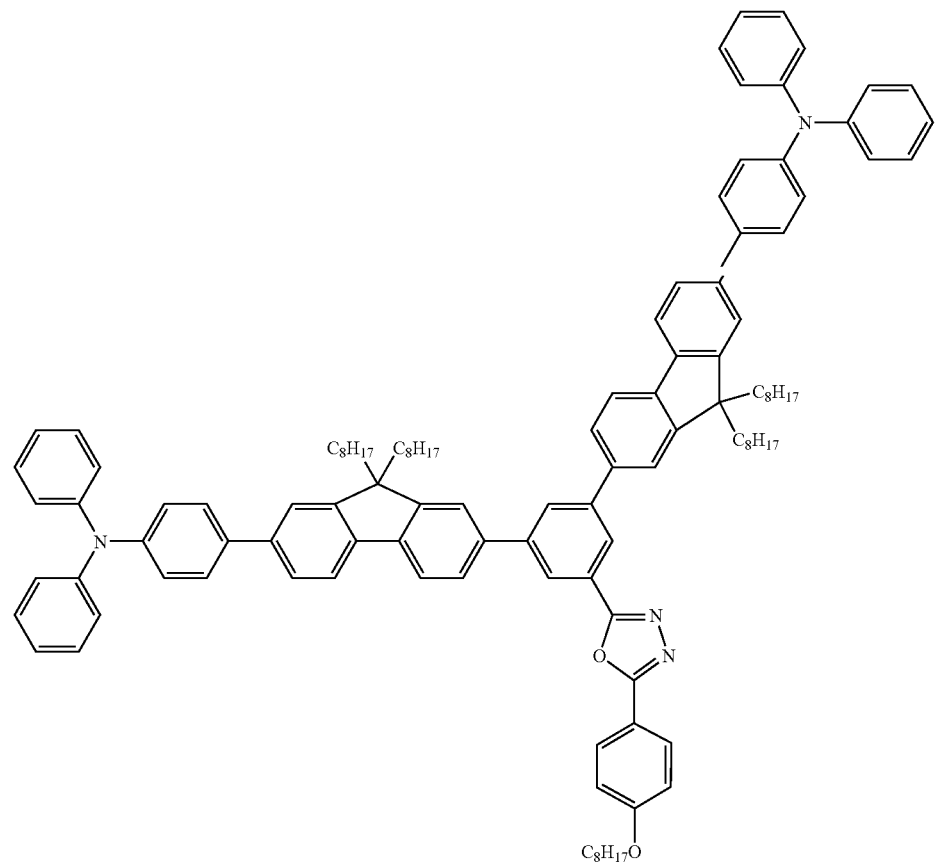

water added. The organic layer was separated and washed with water followed by brine. Drying of the organic layer over $Na_2SO_4$ and evaporation of the solvent gave a light yellow solid. This was suspended in acetone and the mixture brought to reflux and then allowed to stand at room temperature overnight. Filtration of the solid and concentration of the filtrate gave a solid that was subjected to column chromatography (toluene:hexane 3:7) to give 4-[9,9-dioctyl-7-(4,4,5,5-tetramethyl-1,3,2-dioxaborolan-2-yl)-9H-fluoren-2-yl]-N,N-diphenylaniline.

Part E: Synthesis of 2-[3,5-Bis-{9,9-dioctyl-7-(phenyl-4-amino-N,N-diphenyl)-9H-fluoren-2-yl}-phenyl]-5-(4-octyloxy-phenyl)-[1,3,4]oxadiazole.

2-[3,5-Bis-{9,9-dioctyl-7-(phenyl-4-amino-N,N-diphenyl)-9H-fluoren-2-yl}-phenyl]-5-(4-octyloxy-phenyl)-[1,3,4]oxadiazole is prepared by reaction of 4-[9,9-Dioctyl-7-(4,4,5,5-tetramethyl-1,3,2-dioxaborolan-2-yl)-9H-fluoren-2-yl]-N,N-diphenylaniline with 2-(3,5-dibromophenyl)-5-[4-(octyloxy)phenyl]-1,3,4-oxadiazole (2.2 mmole) from example 7 under conditions as outlined in Part B of Example 12. The resulting product can be shown to give rise to photoluminescence and to form films that support both hole and electron transport in OLED compositions.

Example 17

Synthesis of 2-[3,5-Bis-{9,9-dioctyl-7-(3,5-bis-trifluoromethyl-phenyl)-9H-fluoren-2-yl}-phenyl]-5-(4-octyloxy-phenyl)-[1,3,4]oxadiazole ethylammonium chloride) (0.15 g, 0.375 mmole) and 2M sodium carbonate solution (1.25 mL, 2.5 mmole) were added to 10 mL of toluene. This was purged with a stream of nitrogen for about 30 min. Under a nitrogen purge, tetrakis(triphenylphosphine) palladium (0) (14 mg, 0.012 mmole) was added. The reaction mixture was then refluxed for 16 hrs. The reaction was cooled to room temperature and water added. The organic layer was separated and washed with water, followed by brine. Drying of the organic layer over $Na_2SO_4$ and evaporation of the solvent gave a light yellow solid. The solid was dissolved in ether, and a small portion of it was applied on a silica thin layer chromatography (TLC) plate. The TLC plate was eluted with 1:1 toluene:hexane to give three distinctive bands. The middle band was collected and was determined to be 2-{7-[3,5-bis(trifluoromethyl)phenyl]-9,9-dioctyl-9H-fluoren-2-yl}-4,4,5,5-tetramethyl-1,3,2-dioxaborolane obtained as a light yellow oil (28 mg). $^1$H NMR: $\delta$0.53-0.69 (m, 4H), 0.78 (t, 6H), 0.96-1.29 (m, 20H), 1.40 (s, 12H), 1.97-2.11 (m, 4H), 7.52, (s, 1H), 7.56 (d, 1H), 7.72-7.80 (m, 2H), 7.80-7.88 (m, 3H), 8.05 (s, 2H). The band having the greatest elution distance was collected and was determined to be the by-product 2,7-bis[3,5-bis(trifluoromethyl)phenyl]-9,9-dioctyl-9H-fluorene obtained, as a light yellow oil (8 mg). $^1$H NMR: $\delta$0.51-0.65 (m, 4H), 0.70 (t, 6H), 0.91-1.26 (m, 20H), 1.98-2.11 (m, 4H), 7.49, (s, 2H), 7.56 (d, 2H), 7.80 (d, 4H), 8.00 (s, 4H).

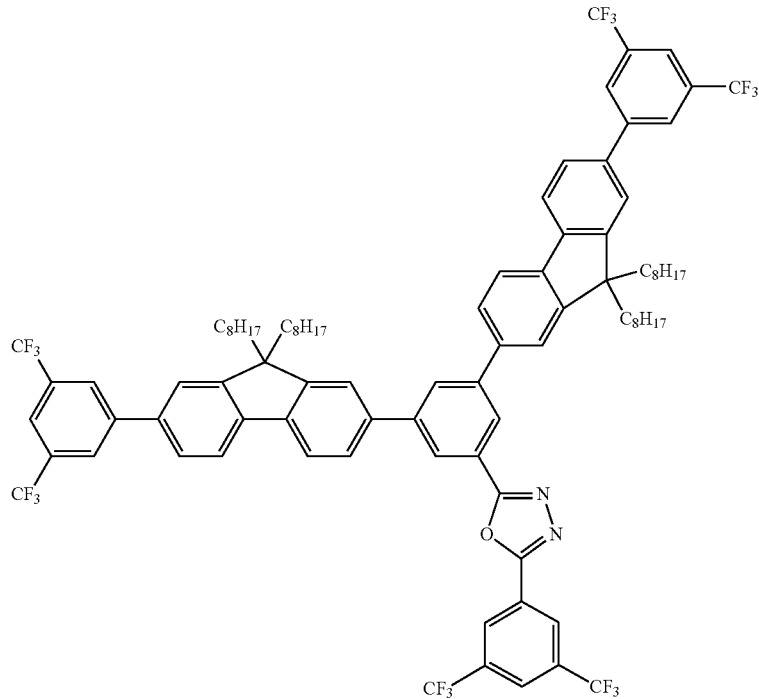

Part A: Synthesis of 2-{7-[3,5-Bis(trifluoromethyl)phenyl]-9,9-dioctyl-9H-fluoren-2-yl}-4,4,5,5-tetramethyl-1,3,2-dioxaborolane and 2,7-Bis[3,5-bis(trifluoromethyl)phenyl]-9,9-dioctyl-9H-fluorene.

3,5-Bistrifluoromethylbromobenzene (0.293 g, 1 mmole), 2-[9,9-dioctyl-7-(4,4,5,5-tetramethyl-1,3,2-dioxaborolan-2-yl)-9H-fluoren-2-yl]-4,4,5,5-tetramethyl-1,3,2-dioxaborolane from (1.28 g, 2 mmole), Aliquat™ 336 (tricaprylylm- Part B: Synthesis of 2-[3,5-Bis-{9,9-dioctyl-7-(3,5-bis-trifluoromethyl-phenyl)-9H-fluoren-2-yl}-phenyl]-5-(4-octyloxy-phenyl)-[1,3,4]oxadiazole 2-[3,5-Bis-{9,9-dioctyl-7-(3,5-bis-trifluoromethyl-phenyl)-9H-fluoren-2-yl}-phenyl]-5-(4-octyloxy-phenyl)-[1,3,4]oxadiazole is prepared by reaction of 2-{7-[3,5-bis(trifluoromethyl)phenyl]-9,9-dioctyl-9H-fluoren-2-yl}-4,4,5,5-tetramethyl-1,3,2-dioxaborolane with 2-(3,5- dibromophenyl)-5-[3,5-bis(trifluoromethyl)phenyl]-1,3,4-oxadiazole under conditions outlined in Part B of Example 12.

Example 18

Synthesis of 2-[3,5-Bis-{9,9-bis-(3,6-dioxahexylphenyl)-9H-fluoren-2-yl}-phenyl]-5-(4-octyloxyphenyl)-[1,3,4]oxadiazole prepared by reaction of 2-bromo-9,9-bis(3,6-dioxahexylphenyl)-fluorene with 2-(3,5-dibromophenyl)-5-[4-(octyloxy)phenyl]-1,3,4-oxadiazole from Example 3. The resulting product can be shown to give rise to photoluminescence and to form films that can be thermally transferred to ionically conducting polymer films such as PEDT (poly(3,4-ethylenedioxythiophene); CH-8000 from Bayer AG, Leverkusen, Germany).

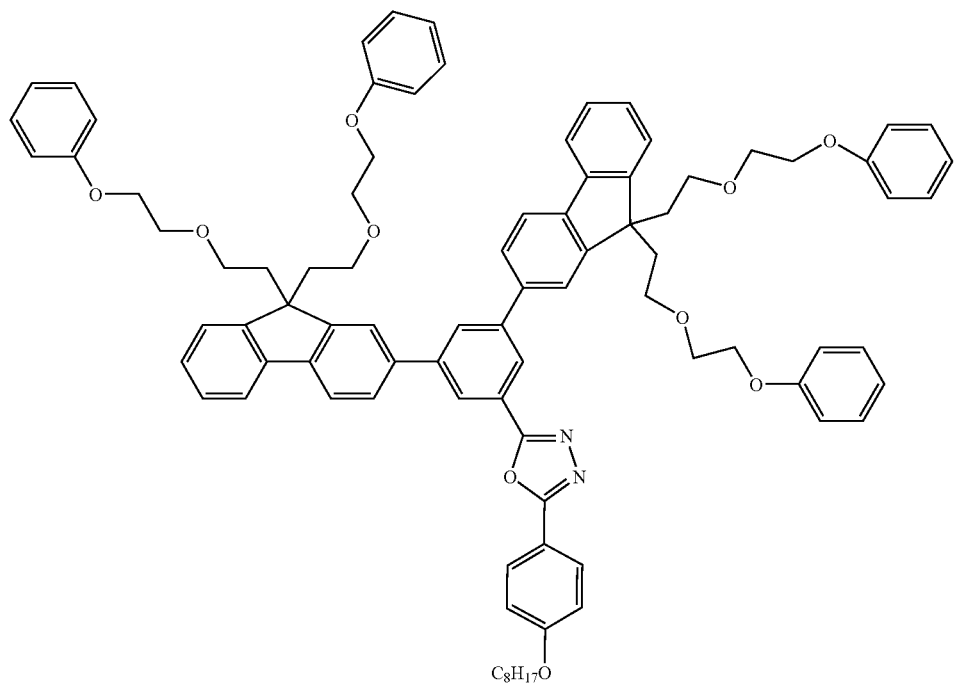

Part A: Synthesis of PhO(CH$_2$)$_2$O(CH$_2$)$_2$I.

PhO(CH$_2$)$_2$O(CH$_2$)$_2$I was made as described in Otera et al., *Bull. Chem. Soc. Jpn.* 2964-2967 (1981), incorporated herein by reference.

Part B: Synthesis of 2-bromo-9,9-bis(3,6-dioxahexylphenyl)-fluorene.

2-Bromo-9,9-bis(3,6-dioxahexylphenyl)-fluorene was synthesized from PhO(CH$_2$)$_2$O(CH$_2$)$_2$I and 2-bromofluorene following the general procedure outlined in Part A of Example 5.

Part C: Synthesis of 2-[3,5-Bis-{9,9-bis-(3,6-dioxahexylphenyl)-9H-fluoren-2-yl}-phenyl]-5-(4-octyloxy-phenyl)-[1,3,4]oxadiazole Following the general procedures for Part B of Example 12, 2-[3,5-Bis-{9,9-bis-(3,6-dioxahexylphenyl)-9H-fluoren-2-yl}-phenyl]-5-(4-octyloxy-phenyl)-[1,3,4]oxadiazole is

Example 19

Synthesis and Utility of N,N-diphenyl-4-(4,4,5,5-tetramethyl-1,3,2-dioxaborolan-2-yl)aniline

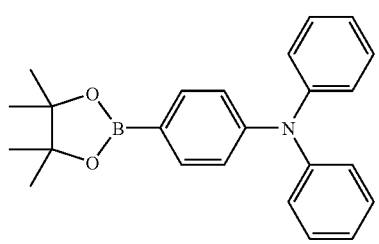

Following the general procedure of arylboronic ester synthesis as reported in Ranger et al., *Chem. Commun.*

1597-1598 (1997), incorporated herein by reference, n-butyllithium was added dropwise via syringe to a −78° C. (acetone-dry ice cooling bath) solution of 4-bromo-N,N-diphenylaniline (24 g, 0.074 mole) in 175 ml dry THF. Stirring was continued at −78° C. for an hour and then at −50° C. for an hour. The mixture was cooled to −78° C. and 2-isopropoxy-4,4,5,5-tetramethyl-1,3,2-dioxaborolane (17.22 g, 0.0925 mole) added via syringe in one portion. The temperature was maintained at −78° C. for three hours. The cooling bath was removed and the reaction left to warm to room temperature while standing for 12 hours. The reaction mixture was poured into saturated ammonium acetate and extracted with ether. The ether layer was dried over magnesium sulfate and concentrated to give a viscous oil. Purification by column chromatography (silica gel eluting with hexane:toluene mixtures of increasing gradient from 100% hexane to 40% hexane) gave N,N-diphenyl-4-(4,4,5,5-tetramethyl-1,3,2-dioxaborolan-2-yl)aniline as an oil (19.9 g, 72.8% yield), which slowly crystallized to a solid on standing.

This compound, can be used to introduce a hole transporting function to the end capping group by direct cross coupling to an arylene oxadiazole dibromide core. Alternatively, this compound can be used for example in an alternate synthetic route to the compound 2-[3,5-Bis-{9,9-dioctyl-7-(phenyl-4-amino-N,N-diphenyl)-9H-fluoren-2-yl}-phenyl]-5-(4-octyloxy-phenyl)-[1,3,4]oxadiazole taught in Example 16. This can be achieved by reacting N,N-diphenyl-4-(4,4,5,5-tetramethyl-1,3,2-dioxaborolan-2-yl)aniline with excess 2,7-dibromo-9,9-dioctylfluorene to generate 4-[9,9-dioctyl-7-bromo-9H-fluoren-2-yl]-N,N-diphenylaniline, which when reacted with 2-(3,5-bis(4,4,5,5-tetramethyl-1,3,2-dioxaborolan-2-yl))phenyl)-5-[4-(octyloxy)phenyl]-1,3,4-oxadiazole from Example 10 under Suzuki coupling conditions will provide the final compound of Example 16.

Example 20

Synthesis and Utility of 2,7-dibromo-9,9-bis(3,6-dioxaheptyl)-fluorene

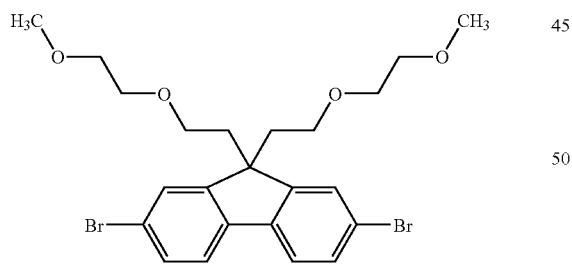

Benzyltriethylammonium chloride (3.19 g, 14 mmole, 0.077 eq) and 2,7-dibromofluorene (59 g, 182 mmole, 1 equiv.) were suspended in 178 mL DMSO. 50% aqeous NaOH 80 mL was added. 1-Bromo-2-(2-methoxyethoxy) ethane (80 g, 437 mmole, 2.4 equiv.) was then added in small portions. The reaction was stirred at room temperature for 2 hours before it was stopped and the aqueous layer was extracted with ether. The combined ether layers were washed with water five times and dried over $Na_2SO_4$. The organic layer was filtered, evaporated to dryness and the residual was flash chromatographed on a silica-gel column to give the pure compound (73 g), in a yield of 86%.

This compound can be used for example to modify the solubility parameter of the compound of Example 16. To do this 2,7-dibromo-9,9-bis(3,6-dioxaheptyl)-fluorene is used in place of 2,7-dibromo-9,9-dioctyl fluorene in Example 16.

Example 21

Synthesis and Utility of 2,7-dibromo-9,9-bis(3,6-dioxahexyl-6-phenyl)-fluorene

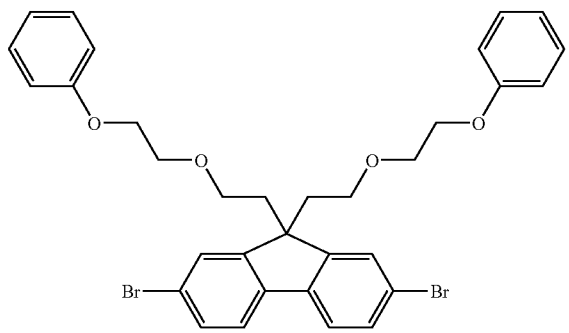

$PhO(CH_2)_2O(CH_2)_2I$ was first synthesized according to methods described by J. Otera, T. Shiomi, K. Murakami and Y. Kawasaki in *Bull. Chem. Soc. Jpn.*, 1981, 2964-2967. 2,7-Dibromo-9,9-bis(3,6-dioxahexyl-6-phenyl)-fluorene was then synthesized from $PhO(CH_2)_2O(CH_2)_2I$ and 2,9-dibromofluorene following the general procedure outlined in Part A of Example 5.

This compound can be used for example to modify the solubility parameter of the compound of Example 16. To do this 2,7-dibromo-9,9-bis(3,6-dioxahexylphenyl)-fluorene is used in place of 2,7-dibromo-9,9-dioctyl fluorene in Example 16.

Example 22

Synthesis and Utility of 9-Phenyl-3,6-bis(4,4,5,5-tetramethyl-1,3,2-dioxaborolan-2-yl)-9H-carbazole

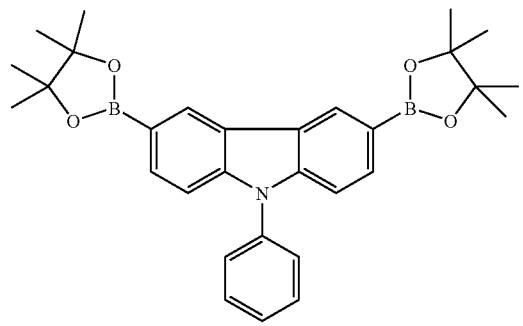

Part A: Synthesis of 3,6-dibromo-9-phenylcarbazole
3,6-dibromo-9-phenylcarbazole was made as described in Park et al., *Tetrahedron*, 42, 12707-12714 (1998), incorporated herein by reference.

Part B: Synthesis of 9-Phenyl-3,6-bis(4,4,5,5-tetramethyl-1,3,2-dioxaborolan-2-yl)-9H-carbazole
A 2 L flask was charged with 600 mL dry THF and 3,6-dibromo-9-phenylcarbazole (60 g, 0.15 mole). This was cooled to −78° C. with an acetone-dry ice bath. n-Butyl-lithium (138 mL of a 2.5M solution in hexanes, 0.34 mole) was added drop-wise via syringe. The reaction was stirred for 20 minutes and then warmed to −50° C. The temperature was reduced to −78° C. and 2-isopropoxy-4,4,5,5-tetramethyl-1,3,2-dioxaborolane (64 g, 0.34 mole) added via syringe at such a rate as to maintain the temperature below −60° C. The temperature was maintained at −78° C. for two hours and then poured into an aqueous solution of ammonium acetate (90 g in 2100 mL water). The layers were phase separated and the aqueous phase extracted with methyl-t-butyl ether (2×200 mL). The combined organic phase and extracts were washed with brine (2×200 mL) and dried over magnesium sulfate. Concentration and re-crystallization of the solid obtained from acetone gave pure 9-phenyl-3,6-bis (4,4,5,5-tetramethyl-1,3,2-dioxaborolan-2-yl)-9H-carbazole.

This compound can be used to modify the hole transport properties of for example the compound of Example 17. To do this 9-Phenyl-3,6-bis(4,4,5,5-tetramethyl-1,3,2-dioxaborolan-2-yl)-9H-carbazole is used in place of 2-[9,9-dioctyl-7-(4,4,5,5-tetramethyl-1,3,2-dioxaborolan-2-yl)-9H-fluoren-2-yl]-4,4,5,5-tetramethyl-1,3,2-dioxaborolane in Example 17.

Example 23

Synthesis and utility of 4,7-Dibromo-2,1,3-benzothiadiazole,3,9-Dibromo-perylene and 3,10-dibromo-perylene 4,7-Dibromo-2,1,3-benzothiadiazole was made as described in Pilgram et al., *J. Heterocycl. Chem.*, 7, 629-633 (1970), incorporated herein by reference.

3,9-Dibromo-perylene and 3,10-dibromo-perylene was made as described in Zinke et al., *Chem.Ber.* 74, 107-112 (1941), incorporated herein by reference. These compounds can be used to modify the light emitting properties of for example the compounds of Example 16 or 17. This can be achieved by substituting one of these compounds for in place of 2,7-dibromo-9,9-dioctyl fluorene in the preparations described in Example 16 or Example 17.

Example 24-31

Electroactive Compositions and Organic Electroluminescent Devices

Electroactive compositions were prepared as follows: The electron transporting compounds (ETA's) of Examples 11-14 were independently dissolved at 1-3 wt/wt % into dichloroethane or toluene (HPLC grade obtained from Aldrich Chemical, Milwaukee, Wis.). A hole transporting agent (HTA) selected from TPD, CBP, and PVK were added in a ratio of ETA/HTA=10:3; in some cases 10:10 or 10:1. The molecular emitter Ir(ppy)$_3$, was introduced in amounts of 0.01-0.5 wt/wt % by addition of small aliquots of a 10 mM solution of the emitter in dichloroethane (DCE). Each coating solution was filtered through a 0.2 μm nylon syringe filter before application.

Organic electroluminescent devices were constructed as follows: Glass squares of 2 cm×2 cm having on one side a vapor deposited coating of indium tin oxide (ITO) were obtained from Thin Film Devices (Anaheim, Calif.). The ITO coated sides were cleaned with mthanol, treated with an O$_2$ plasma etch (4 min at 50 W and 200 mTorr), treated by spin coating (2500 rpm for 30 sec) of an aqueous solution of PEDT/PSS copolymer and dried under nitrogen purge at 115° C. Next, the coating solutions prepared above were each spin coated on top of a PEDT/PSS coated substrate (2000 rpm for 30 sec). The glass squares were then mounted into an aluminum frame, introduced into a vacuum deposition chamber, and pumped to 10$^{-6}$ torr for about 1 hour. Cathodes were applied by vapor depositing about 10 Å of LiF and about 2000 Å of aluminum.

The resulting organic electroluminescent lamps were evaluated for drive voltages (V), external percent quantum efficiencies (% Q.E.), luminescence intensities (cd/m$^2$), and emission maxima ($\lambda_{max}$ nm) for blue, green, and red lamps operating at 20 mA/cm$^2$ drive current.

Table 1 summarizes the electroactive compositions and results of the respective lamp evaluations. The materials in the electroactive compositions are recorded in Table 1 as the number of parts (p) by weight added to 1000 parts (1000 p) DCE to make the spin coating solution used in preparing the lamps.

TABLE 1

Electroactive Compositions and Lamp Evaluation Results

| Example | p ETA/ 1000 p DCE (ETA) | p HTA/ 1000 p DCE (HTA) | p Emitter/ 1000 p DCE (Emitter) | Electro-luminescence λnm |
|---|---|---|---|---|
| 24 | 10 (Ex. 11) | 3 (TPD) | 0.085 (Ir(ppy)$_3$) | 513 |
| Comparative 25 | 10 (C8O) | 3 (CBP) | 0.085 (Ir(ppy)$_3$) | 508 |
| 26 | 10 (C8O) | 3 (Ex. 14) | 0.085 (Ir(ppy)$_3$) | 510 |
| 27 | 10 (Ex. 12) | 3 (CBP) | 0.085 (Ir(ppy)$_3$) | 508 |
| 28 | 10 (Ex. 12) | 3 (Ex. 14) | 0.085 (Ir(ppy)$_3$) | 508 |
| 29 | 10 (Ex. 12) | 3 (PVK) | 0.085 (Ir(ppy)$_3$) | 508 |
| 30 | 10 (Ex. 11) | 3 (PVK) | 0.085 (Ir(ppy)$_3$) | 505 |
| 31 | 10 (Ex. 12) | 3 (PVK) | 0.085 (Ir(ppy)$_3$) | 508 |

(Ex. 11) means the compound of Example 11.
(Ex. 12) means the compound of Example 12.
(Ex. 14) means the compound of Example 14.

Example 32

Preparation of a Donor Sheet

A thermal transfer donor sheet is prepared in the following manner. An LTHC solution, described in Table 2, is coated onto a 0.1 mm thick polyethylene terephthalate (PET) film substrate (M7 from Teijin, Osaka, Japan). Coating is performed using a Yasui Lab Coater, Model CAG-150, using a microgravure roll with 150 helical cells per inch. The LTHC coating is in-line dried at 80° C. and cured under ultraviolet (UV) radiation.

TABLE 2

LTHC Solution

| Component | Trade Designation | Parts by Weight |
|---|---|---|
| carbon black pigment | Raven 760 Ultra[1] | 3.88 |
| polyvinyl butyral resin | Butvar B-98[2] | 0.69 |
| acrylic resin | Joncryl 67[3] | 2.07 |
| dispersant | Disperbyk 161[4] | 0.34 |
| fluoro surfactant | FC-430[5] | 0.01 |
| epoxy novolac acrylate | Ebecryl 629[6] | 13.18 |

TABLE 2-continued

LTHC Solution

| Component | Trade Designation | Parts by Weight |
| --- | --- | --- |
| acrylic resin | Elvacite 2669[7] | 8.79 |
| 2-benzyl-2-(dimethylamino)-1-(4-(morpholinyl) phenyl) butanone | Irgacure 369[8] | 0.89 |
| 1-hydroxycyclohexyl phenyl ketone | Irgacure 184[8] | 0.13 |
| 2-butanone | | 43.75 |
| 1,2-propanediol monomethyl ether acetate | | 26.25 |

[1]Columbian Chemicals Co., Atlanta, GA
[2]Solutia Inc., St. Louis, MO
[3]S. C. Johnson & Son, Inc. Racine, WI
[4]Byk-Chemie USA, Wallingford, CT
[5]3M Co., St. Paul, MN
[6]UCB Radcure Inc., N. Augusta, SC
[7]ICI Acrylics Inc., Memphis, TN
[8]Ciba-Geigy Corp., Tarrytown, NY Next, an interlayer solution, given in Table 3, is coated onto the cured LTHC layer by a rotogravure coating method using the Yasui Seiki lab coater, Model CAG-150, with a microgravure roll having 180 helical cells per lineal inch. This coating is in-line dried at 60° C. and cured under ultraviolet (UV) radiation.

TABLE 3

Interlayer Coating Solution

| Component | Parts by Weight |
| --- | --- |
| SR 351 HP (trimethylolpropane triacrylate ester, available from Sartomer, Exton, PA) | 14.85 |
| Butvar B-98 | 0.93 |
| Joncryl 67 | 2.78 |
| Irgacure 369 | 1.25 |
| Irgacure 184 | 0.19 |
| 2-butanone | 48.00 |
| 1-methoxy-2-propanol | 32.00 |

Next, a transfer layer is formed on the interlayer of the donor sheet. The transfer layer is disposed on the donor sheet by spinning the molecularly doped polymer composition of Example 26 or 27 at about 2000-2500 rpm for 30 seconds (Headway Research spincoater) to yield a film thickness of approximately 50 nm.

Example 33

Laser Induced Thermal Imaging of Transfer Layer

Part A: Preparation of Receptor Substrates

PEDT (poly(3,4-ethylenedioxythiophene)) solution (Baytron P 4083 from Bayer AG, Leverkusen, Germany) diluted 1:1 with deionized water) is filtered through a WHATMAN PURADISC 0.2 μm nylon syringe filter.

Unpatterned ITO (indium tin oxide) glass (Delta Technologies, Stillwater, Minn., less than 100 Ω/square, 1.1 mm thick) is ultrasonically cleaned in a hot, 3% solution of Deconex 12NS detergent (Borer Chemie A G, Zuchwil, Switzerland). The substrates are then placed in the Plasma Science plasma treater for surface treatment under the following conditions: time: 2 minutes; power: 500 watt (165 W/cm$^2$); and oxygen flow: 100 Torr.

Immediately after plasma treatment, the PEDT solution is filtered and dispensed through a WHATMAN PURADISC 0.2 μm nylon syringe filter onto the ITO substrate. The substrate is then spun (Headway Research spincoater) at 2000 rpm for 30 seconds yielding a PEDT film thickness of 40 nm. All of the substrates are heated to 200° C. for 5 minutes under nitrogen.

Part B: Laser Induced Thermal Imaging of Transfer Layer from Donor Sheet

Donor sheets of Example 33 are brought into contact with the receptor substrates. Next, the donor sheets are imaged using two single-mode Nd:YAG lasers. Scanning is performed using a system of linear galvanometers, with the combined laser beams focused onto the image plane using an f-theta scan lens as part of a near-telecentric configuration. The laser energy density is 0.4 to 0.8 J/cm$^2$. The laser spot size, measured at the 1/e$^2$ intensity, is 30 micrometers by 350 micrometers. The linear laser spot velocity is adjustable between 10 and 30 meters per second, measured at the image plane. The laser spot is dithered perpendicular to the major displacement direction with about a 100 micrometer amplitude. The transfer layers are transferred as lines onto the receptor substrates, and the intended width of the lines is about 100 micrometers. Laser induced thermal imaging is performed at a scan velocity from 11.4 to 20.0 m/s and the following conditions: dose 0.4-0.7 J/cm$^2$; scan speed 20-11.4 m/s; line width 90 microns; and pitch 225 microns.

Digital images of the resulting laser induced thermal imaging pattern show transfer of the electroactive composition to the receptor surface in regions that are imaged, and show regions without the electroactive composition on the unimaged receptor surface.

What is claimed is:

1. A compound comprising an aromatic core and two end capping groups conjugated to the aromatic core, said compound having Formula IV:

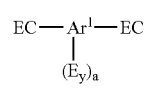

IV wherein
each Ar$^1$ is independently a radical of benzene, naphthalene, anthracene, phenanthrene, 9,10-dihydrophenanthrene, 4,5,9,10-tetrahydropyrene, fluorene, 9-silafluorene, 6,12-dihydroindeno[1,2-b]fluorene, 5,12-dihydro-6H-indeno[1,2-b]phenanthrene, 5,6,12,13-tetrahydrodibenzo[a,h]anthracene, 2-phenyl-9H-fluorene, or acenaphthene that is unsubstituted or substituted with one or more groups selected from alkyl, alkenyl, alkoxy, fluoro, fluoroalkyl, perfluoroalkyl, heteroalkyl, and combinations thereof,
wherein when Ar$^1$ is a radical of benzene, the group

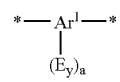

is selected from

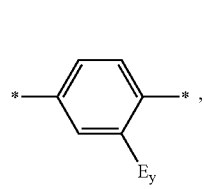 , 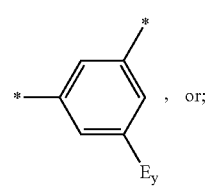 , or;

-continued

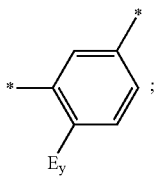

each a is independently 1 or 2;
each $E_y$ is independently a structure of Formula II or Formula III:

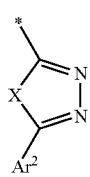

II

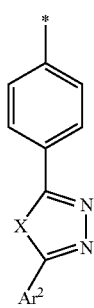

III each X is independently O, S, or $NR^1$, where $R^1$ is alkyl, aryl, heteroaryl, heteroalkyl, or combinations thereof;
each $Ar^2$ is independently an aryl group that is unsubstituted or substituted with one or more groups selected from alkyl, alkenyl, alkoxy, aryl, aryloxy, fluoro, fluoroalkyl, perfluoroalkyl, heteroalkyl, alkyl oxadiazolyl, aryl oxadiazolyl, alkyl triazolyl, aryl triazolyl, diarylamino, aryldiarylamino, and combinations thereof;
each asterisk (-*) indicates the location of a bond to another group in the compound; and
each end capping group (EC) is independently an aryl, heteroaryl without a —C=N— unit, or tertiary amino aryl group that is unsubstituted or substituted with one or more groups selected from alkyl, alkenyl, alkoxy, aryl, aryloxy, fluoro, fluoroalkyl, perfluoroalkyl, heteroalkyl, heteroaryl without a —C=N— unit, and combinations thereof, wherein said end capping groups are conjugated to the aromatic core.

2. The compound of claim 1 wherein the

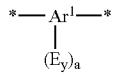

moiety in Formula IV is a divalent radical of

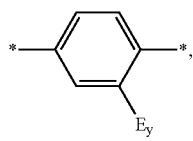

XXXVII

-continued

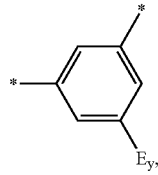

XXXVIII

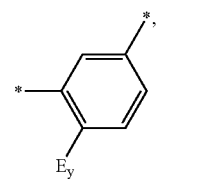

XXXIX

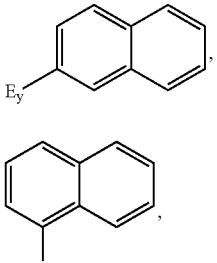

XI

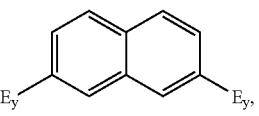

XII

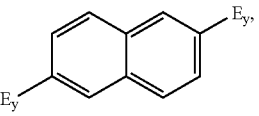

XIII

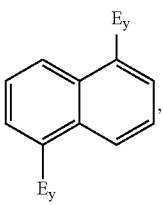

XIV

XV

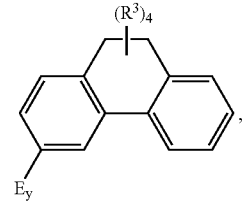

XVI

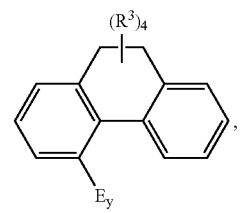

XVII

-continued
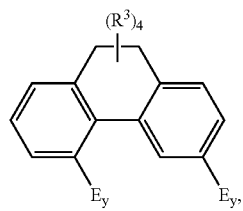
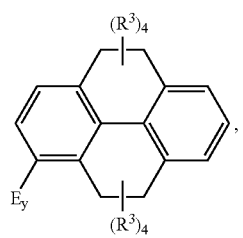
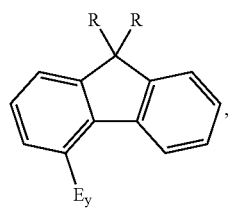
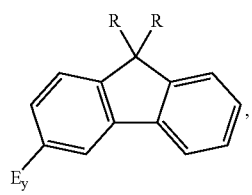
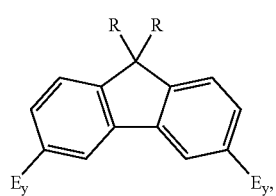
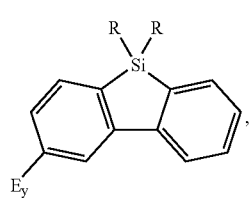
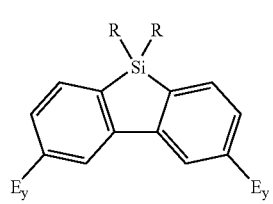
-continued
XVIII
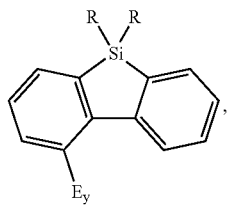 XXV
XIX
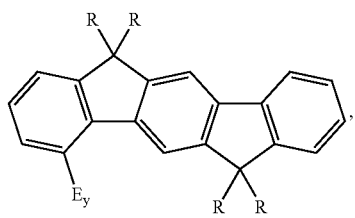 XXVI
XX
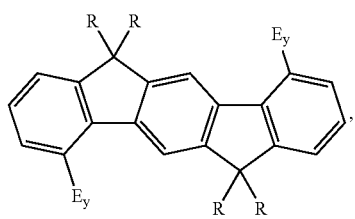 XXVIa
XXI
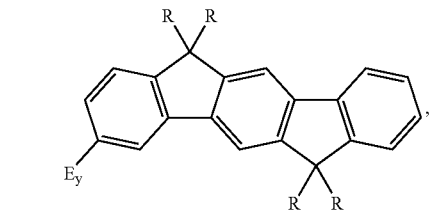 XXVII
XXII
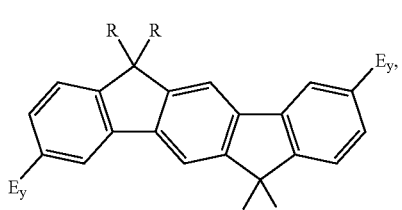 XXVIII
XXIII
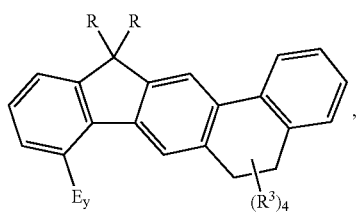 XXIX
XXIV
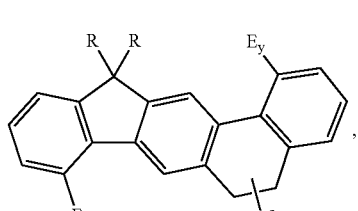 XXX -continued

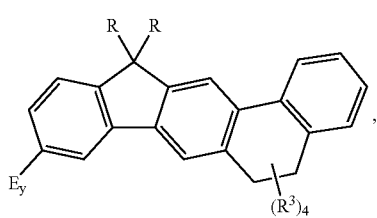,

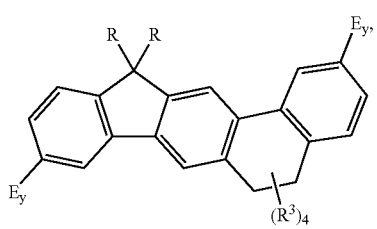,

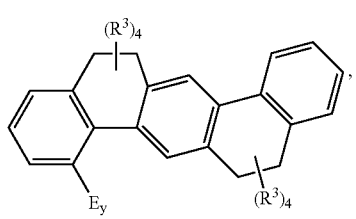,

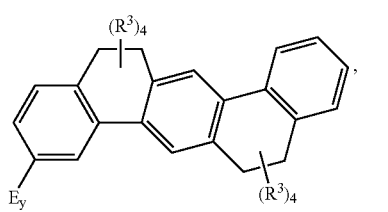,

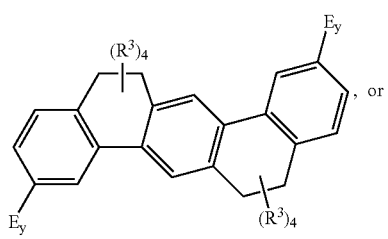, or

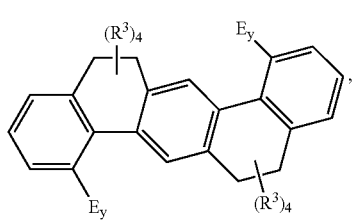, that is unsubstituted or substituted with one or more groups selected from a $C_{1-20}$ alkyl, $C_{2-20}$ alkenyl, $C_{1-20}$ alkoxy, fluoro, $C_{1-20}$ fluoroalkyl, $C_{1-20}$ perfluoroalkyl, $C_{1-20}$ heteroalkyl, and combinations thereof, wherein each R is independently a $C_{1-30}$ alkyl, $C_{2-30}$ alkenyl, $C_{1-30}$ alkoxy, $C_{1-30}$ heteroalkyl, or combinations thereof; and each $R^3$ is independently selected from hydrogen, $C_{1-30}$ alkyl, $C_{2-30}$ alkenyl, $C_{1-30}$ alkoxy, $C_{1-30}$ heteroalkyl, and combinations thereof.

3. The compound of claim 2, wherein at least one R or $R^3$ comprises a heteroalkyl having up to 30 carbon atoms, wherein the heteroalkyl comprises a soft segment comprising a divalent poly(oxyalkylene) segment of Formula VI $$* -O(C_mH_{2m}O)_y-*$$

or a divalent poly(dialkylsiloxane) segment of Formula VII $$* +Si(C_wH_{2w+1})_2O+_{\overline{y}}*,$$

where in is an integer of 1 to 6, y is an integer of 2 to 20, and xv is an integer of 1 to 10 with the proviso that m, y, and w are selected so as to provide up to 30 carbon atoms.

4. The compound of claim 2, wherein the compound is substituted with a fluoro, fluoroalkyl, or perfluoroalkyl group.

5. The compound of claim 1, wherein $Ar^2$ is an aryl group selected from phenyl, biphenyl, terphenyl, anthryl, naphthyl, acenaphthyl, phenanthryl, dihydrophenanthrenyl, anthracenyl, fluorenyl, 9-silafluorenyl, tetrahydropyrenyl, perylenyl, spirobisfluorenyl, fluoranthenyl, pyrenyl, dihydropyrenyl, tetrahydropyrenyl, rubrenyl, chrysenyl, 5,6,12,13-tetrahydrodibenzo[a,h]anthracenyl, 6,12-dihydroindeno[1,2-b]fluorenyl, 5,12-dihydro-6H-indeno[1,2-b]phenanthrenyl, and benzo[g,h,l]perylenyl that is unsubstituted or substituted with one or more $C_{1-20}$ alkyl, $C_{1-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-30}$ alkyl oxadiazolyl, $C_{3-30}$ aryl oxadiazolyl, $C_{3-20}$ alkyl triazolyl, $C_{3-30}$ aryl triazolyl, $C_{3-30}$ diarylamino, $C_{3-30}$ diarylaminoaryl, or combinations thereof.

6. The compounds of claim 1, wherein the $$\begin{array}{c} *-Ar^1-* \\ | \\ (E_y)_a \end{array}$$

radical in Formula IV is selected from

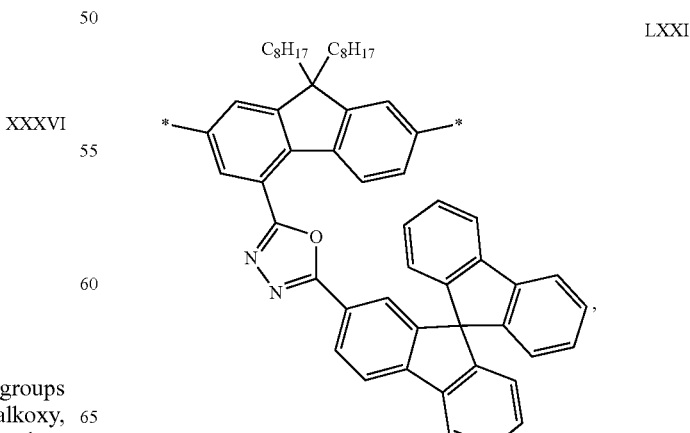,

-continued
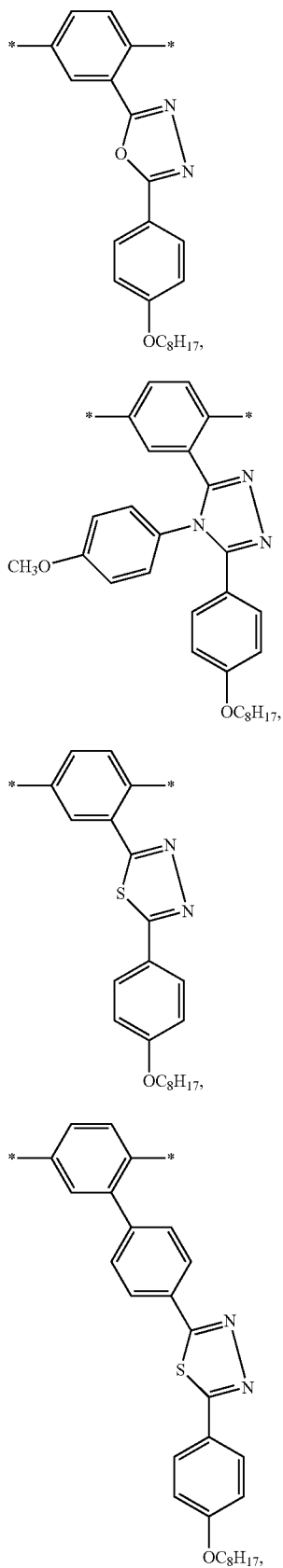
LXXII
LXXIII
LXXIV
LXXV
-continued
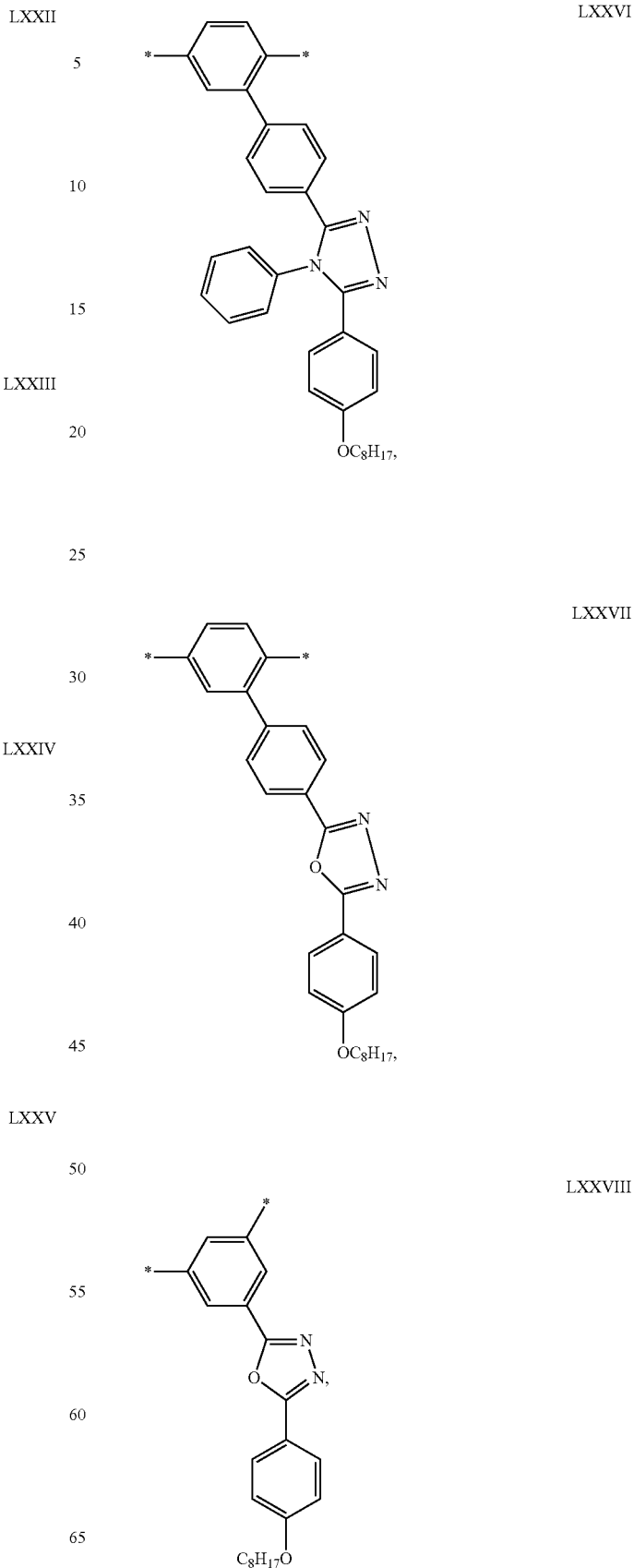
LXXVI
LXXVII
LXXVIII -continued
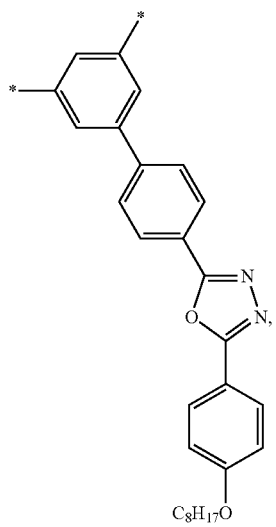
LXXIX
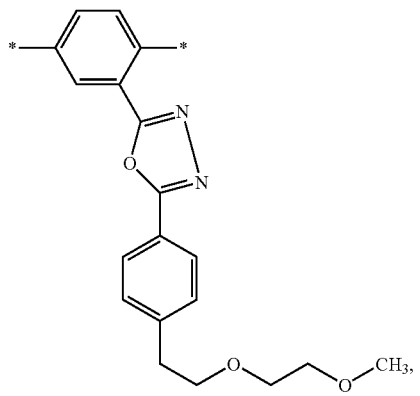
LXXXII
LXXX
LXXXIII
LXXXI
LXXXIV
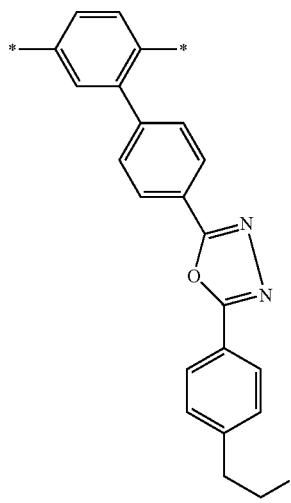
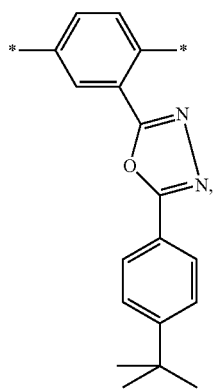

-continued
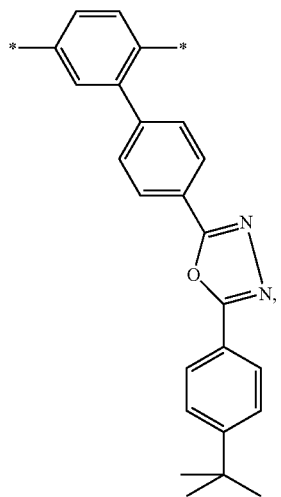 LXXXV
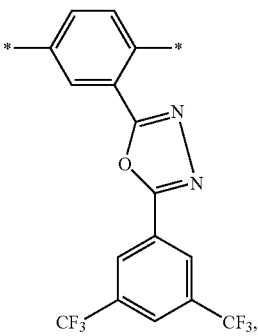 LXXXVIII
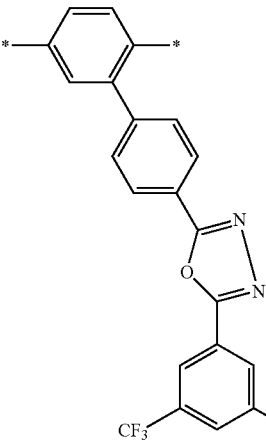 LXXXIX
LXXXVI
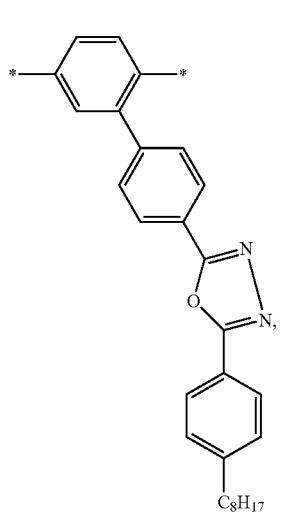 LXXXVII
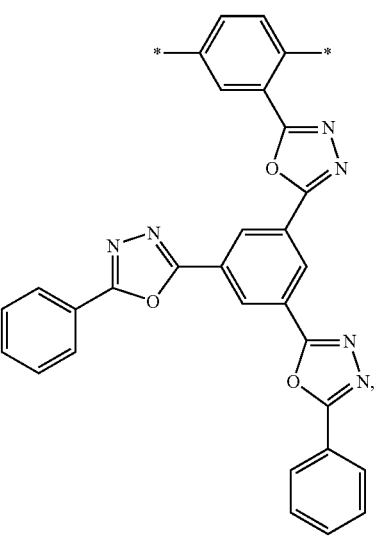 XC -continued
XCI
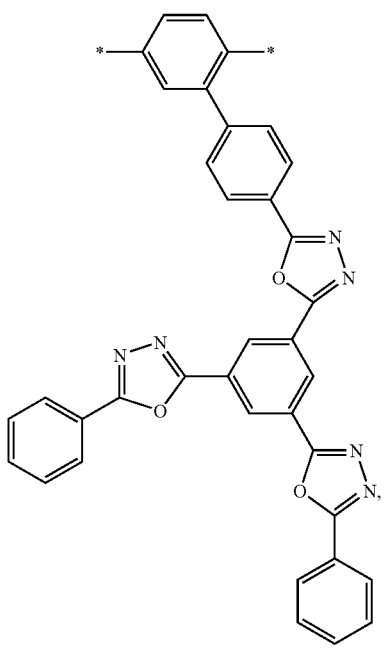
XCII
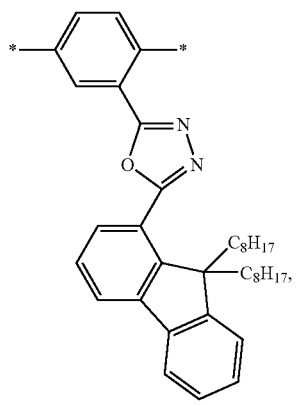
XCIII
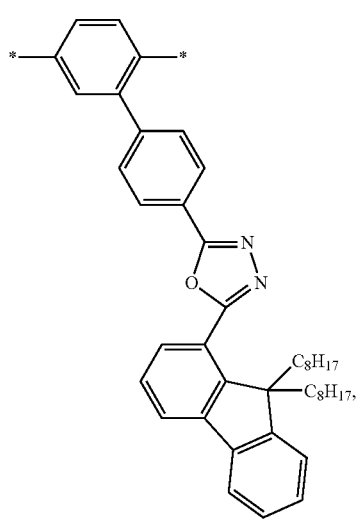
-continued
XCIV
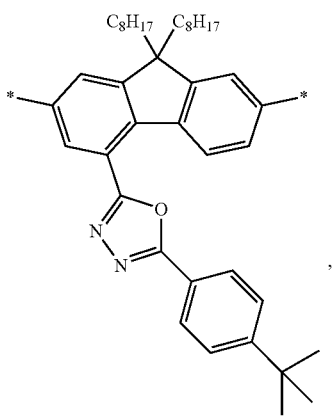
XCV
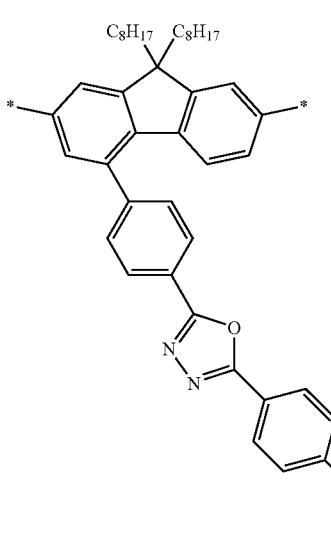
XCVI
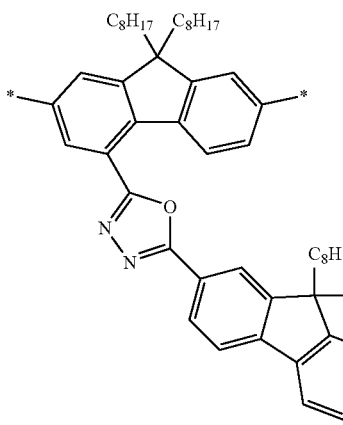

-continued

XCVII

XCVIII

XCIX

CII

CIII

CIV or

-continued

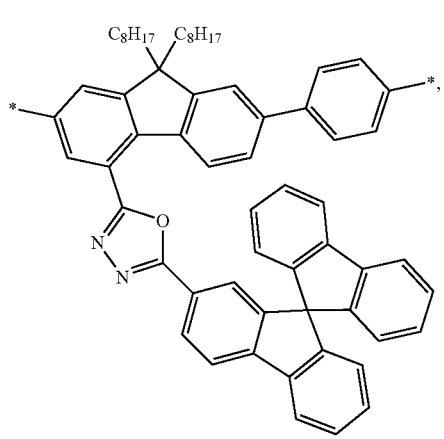

CV

7. The compound of claim 1, wherein at least one of the end capping groups comprises a $C_{6-40}$ aryl comprising phenyl, biphenyl, terphenyl, anthryl, naphthyl, acenaphthyl, phenanthryl, dihydrophenanthrenyl, anthracenyl, fluorenyl, 9-silafluorenyl, tetrahydropyrenyl, perylenyl, spirobistfluorenyl, fluoranthenyl, pyrenyl, dihydropyrenyl, tetrahydropyrenyl, rubrenyl, chrysenyl, benzo[g,h,i]perylenyl, or a radical thereof,
wherein the end capping group is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl without a —C=N— unit, and combinations thereof.

8. The compound of claim 1, wherein at least one of the end capping groups comprises a $C_{3-40}$ heteroaryl or heteroarylene comprising a radical of furanyl, thiophenyl, bithiophenyl, N-aryl pyrrolyl, N-alkyl pyrrolyl, benzofuranyl, benzothiophenyl, indolyl, N-alkyl carbazolyl, N-aryl carbazolyl, diaryl silanolyl, or a radical thereof,
wherein the end capping group is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl without a —C=N— unit, and combinations thereof.

9. The compound of claim 1, wherein at least one of the end capping groups comprises a $C_{12-60}$ tertiary amino aromatic aryl comprising a radical of diarylaniline, alkylcarbazole, arylcarbazole tetraaryldiamine, starburst amine, peraryltriamine, dendritic amine, or spiroamine,
wherein the end capping group is unsubstituted or substituted with one or more aroups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl without a —C=N— unit, and combinations thereof.

10. The compound of claim 1, wherein a.t least one of the end capping groups comprises a $C_{12-60}$ tertiary amino aromatic aryl comprising a radical of N,N,N'N'-tetraarylbenzidine, N,N,N',N'-tetraaryl-1,4-phenylenediamine, N,N,N'N'-tetraaryl-2,7-diaminofluorene, N,N'-bis(3-methylphenyl)-N,N'-bis(phenyl)benzidine, N,N'-bis(1-naphthyl)-N,N'-bis(phenyl)benzidine, 4,4'-bis(carbazolyl)biphenyl, 1,4-bis(carbazolyl)biphenyl, 4,4',4"-tris(N,N-diarylamino)triphenylamine, 1,3,5-tris(4-diarylaminophenyl)benzene, 4,4',4"-tris(N,N-diphenylamino)triphenylamine, 4,4',4"-tris(N-3-methylphenyl-N-phenylamino)triphenylamine, or 1,3,5-tris(4-diphenylaminophenyl)benzene,
wherein the end capping group is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl without a —C=N— unit, and combinations thereof.

11. The compound of claim 1, wherein at least one end capping group comprises a monovalent radical of

CVI

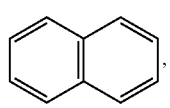
CVII

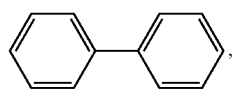
CVIII

CIX

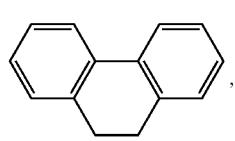
CX

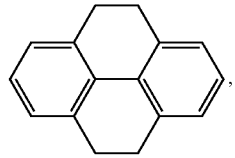
CXI

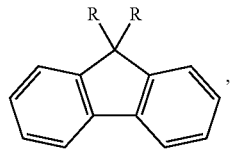
CXII

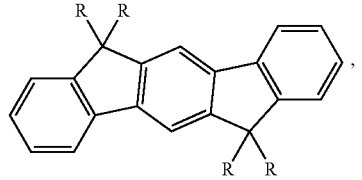
CXIII

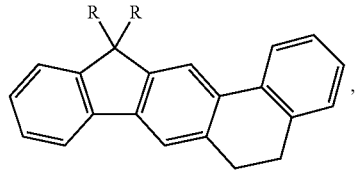
CXIV

-continued

CXV
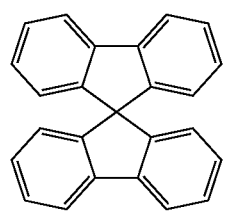

CXVI
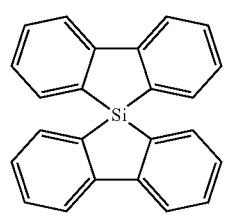

CXVII
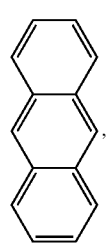

CXVIII
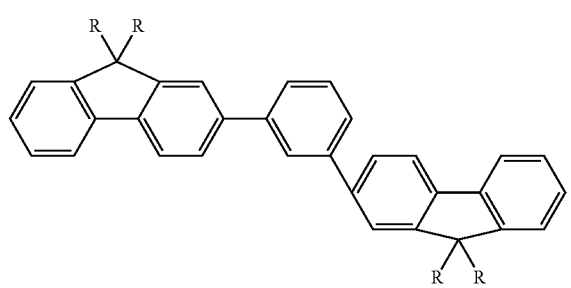

CXIX
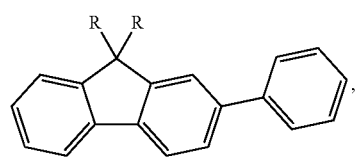

CXX
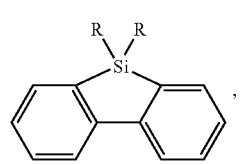

CXXIV
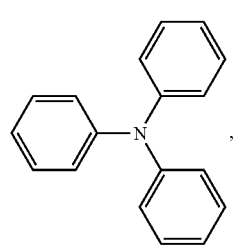

-continued

CXXV
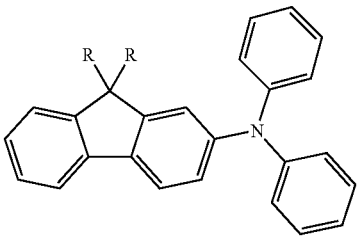

CXXVI
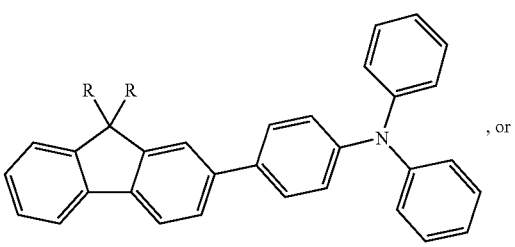

CXXVII
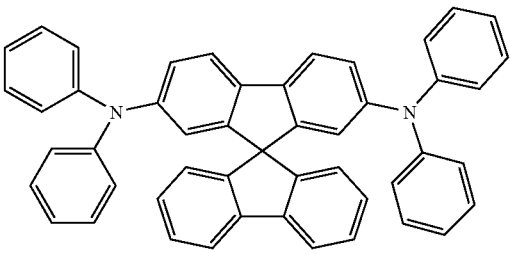

that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl without a —C=N— unit, and combinations thereof, wherein each R is independently selected from $C_{1-30}$ alkyl, $C_{2-30}$ alkenyl, $C_{1-30}$ alkoxy, $C_{6-20}$ aryl, $C_{6-20}$ aryloxy, $C_{3-20}$ heteroaryl without a —C=N— unit, $C_{1-30}$ heteroalkyl, and combinations thereof; and each X is independently O, S, or $NR^1$, where $R^1$ is a $C_{1-30}$ alkyl, $C_{6-20}$ aryl, $C_{3-30}$ heteroaryl without a —C=N— unit, $C_{1-30}$ heteroalkyl, or combinations thereof.

12. The compound of claim 11, wherein the end capping group further comprises a moiety conjugated to a group of Formula CVI to CXXVII, said moiety selected from a divalent radical of CXXVIII

CXXIX
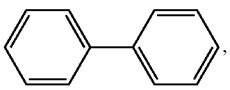

CXXX

-continued
CXXXI
CXXXII
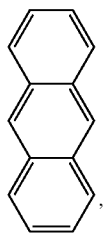
CXXXIII
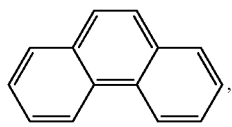
CXXXIV
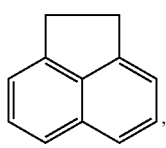
CXXXV
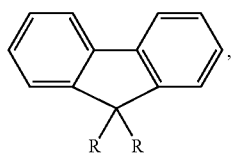
CXXXVI
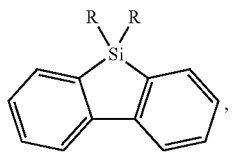
CXXXVII
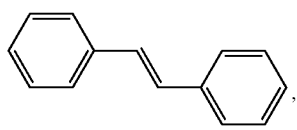
CXXXVIII
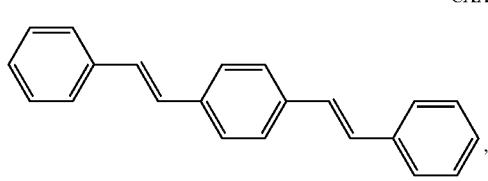
CXXXIX
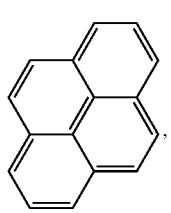
-continued
CXL
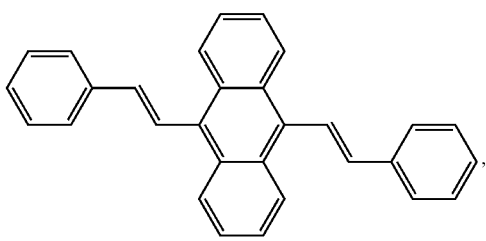
CXLI
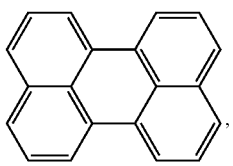
CXLII
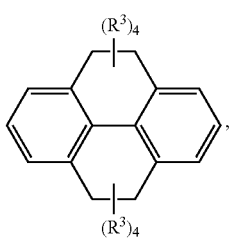
CXLIII
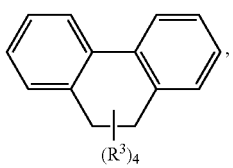
CXLIV
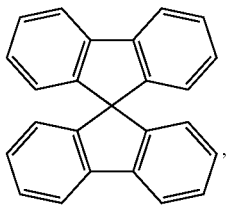
CXLV
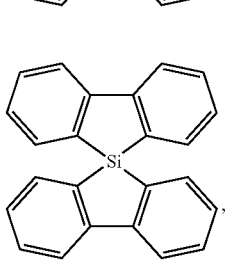
CXLVI
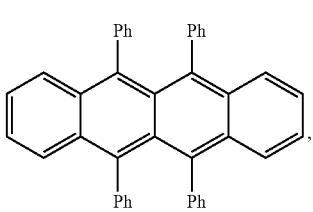

-continued

CXLVII
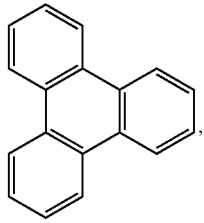

CXLVIII
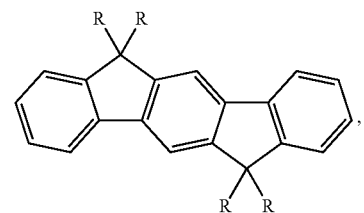

CXLIX
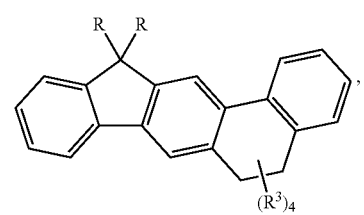

CL
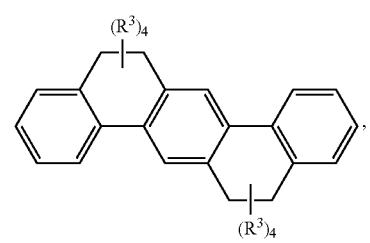

CLI
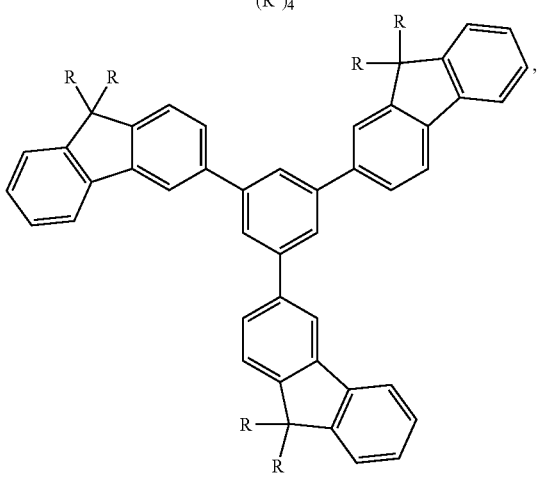

CLII
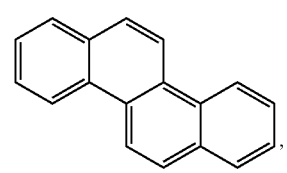

CLIII
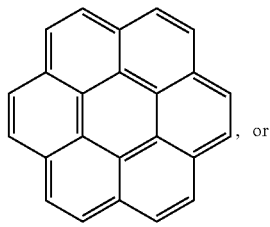

CLIV
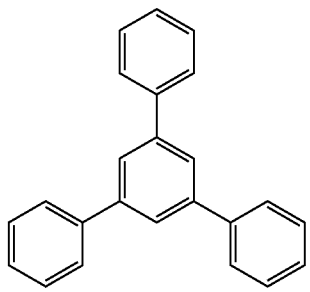, or

CLV
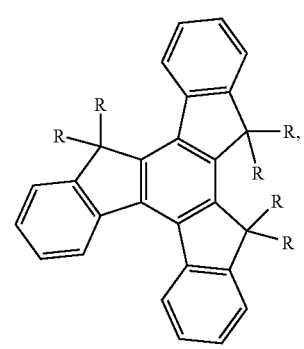

that is unsubstituted or substituted with one or more groups selected horn $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl without a —C=N— unit, and combinations thereof, wherein each R is independently selected from $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl without a —C=N— unit, $C_{1-30}$ heteroalkyl, and combinations thereof; and each $R^3$ is independently selected from hydrogen, $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl without a —C=N— unit, $C_{1-30}$ heteroalkyl, and combinations thereof.

13. The compound of claim 11, wherein the end capping group further comprises a moiety conjugated to a group of Formula CVI to CXXVII, said moiety selected from a divalent radical of CLXXVI
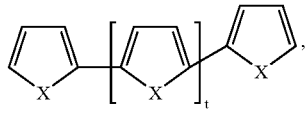

CLXXVII
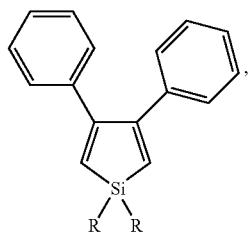

-continued

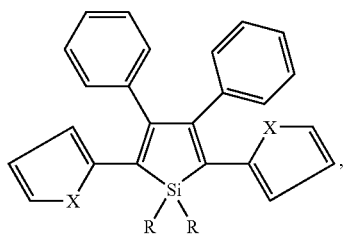
CLXXVIII

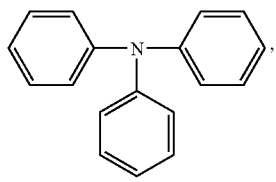
CLXXIX

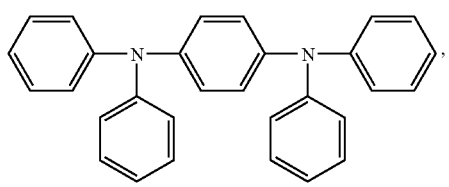
CLXXX

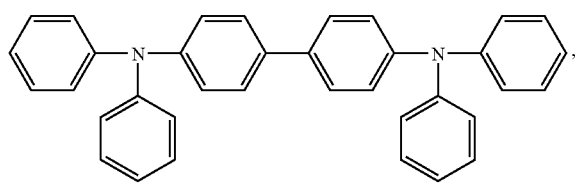
CLXXXI

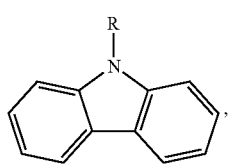
CLXXXII

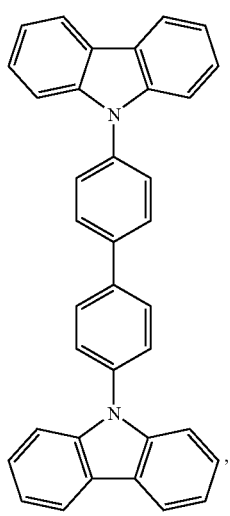
CLXXXIII

-continued

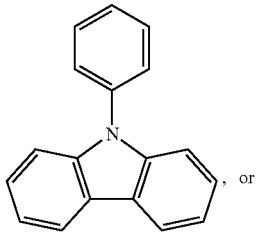
CLXXXIV, or

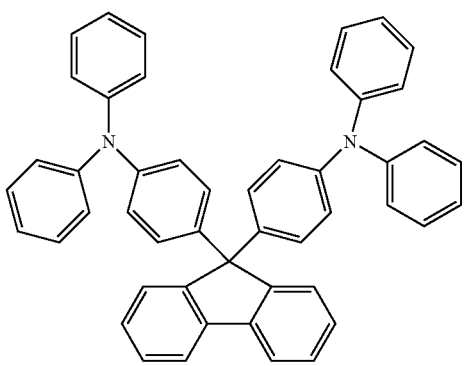
CLXXXV that is unsubstituted or substituted with one or more groups selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl without a —C=N— unit, and combinations thereof, wherein each R is independently selected from $C_{1-30}$ alkyl, $C_{2-30}$ alkenyl, $C_{1-30}$ alkoxy, $C_{6-30}$ aryl, $C_{6-30}$ aryloxy, $C_{3-30}$ heteroaryl without a —C=N— unit, $C_{1-30}$ heteroalkyl, and combinations thereof;

each X is independently O, S, or $NR^1$, where $R^1$ is a $C_{1-30}$ alkyl, $C_{6-20}$ aryl, $C_{3-30}$ heteroaryl without a —C=N— unit, $C_{1-30}$ heteroalkyl, or combinations thereof; and each t is an integer equal to 0 to 4.

14. The compound of claim 1, wherein the compound is substituted with at least one soft segment comprising a divalent poly(oxyalkylene) segment of formula

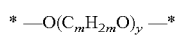

or a divalent poly(dialkylsiloxane) segment of formula

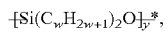

where m is an integer of 1 to 6, y is an integer of 2 to 20, and w is an integer of 1 to 10.

15. The compound of claim 1, wherein the compound is substituted with at least one fluoro, fluoroalkyl, or perfluoroalkyl group.

16. The compound of claim 1, wherein the compound is
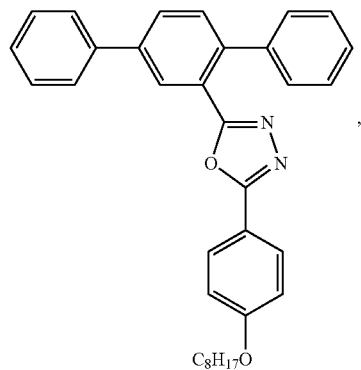
CCX
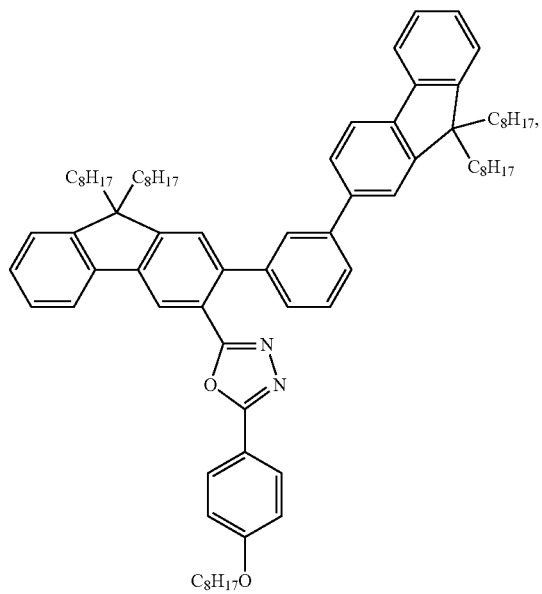
CCXI
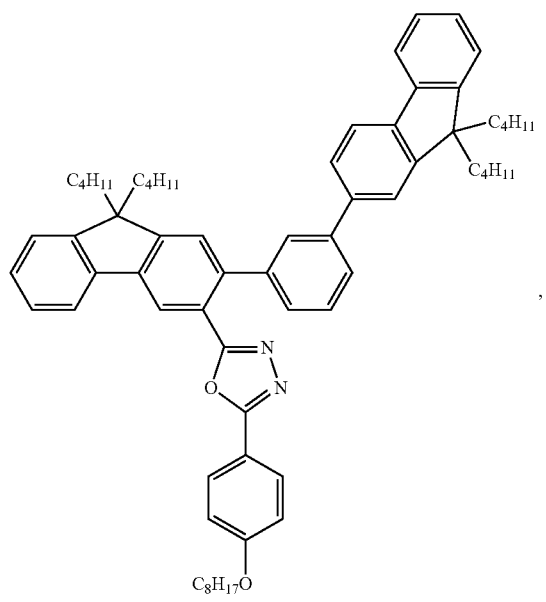
CCXII
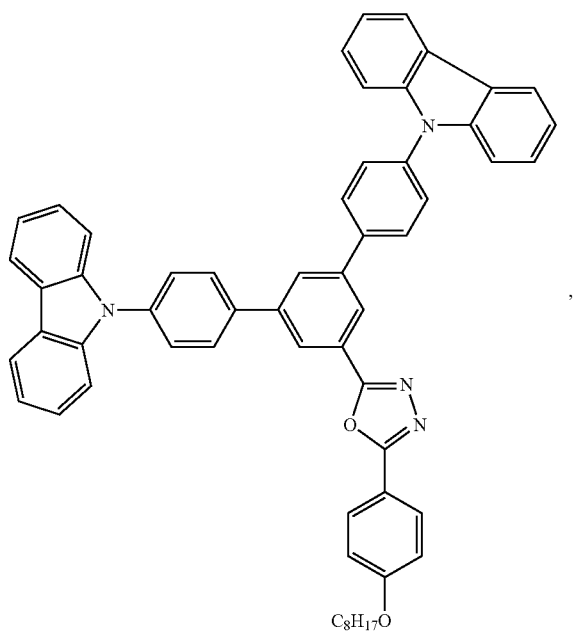
CCXIII

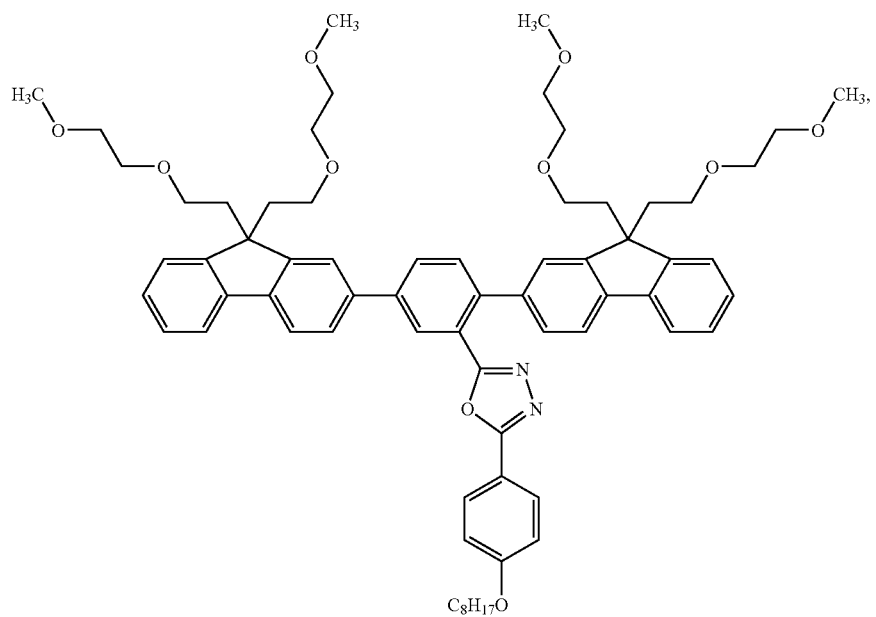
CCXIV
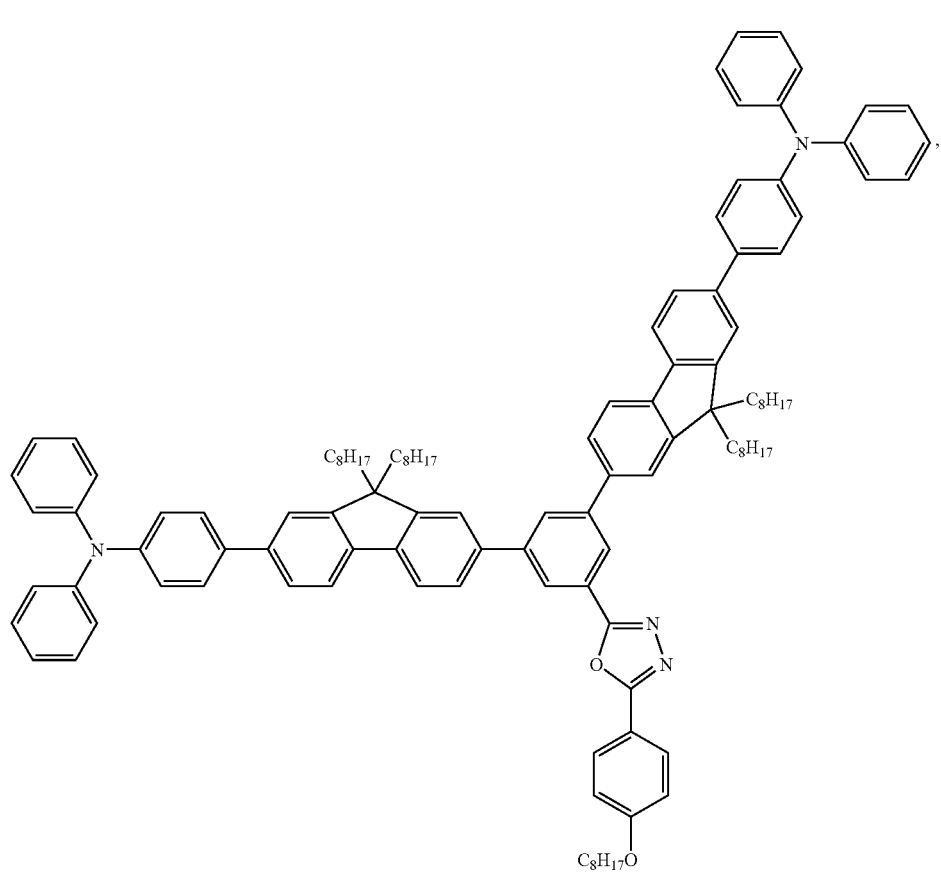
CCXV

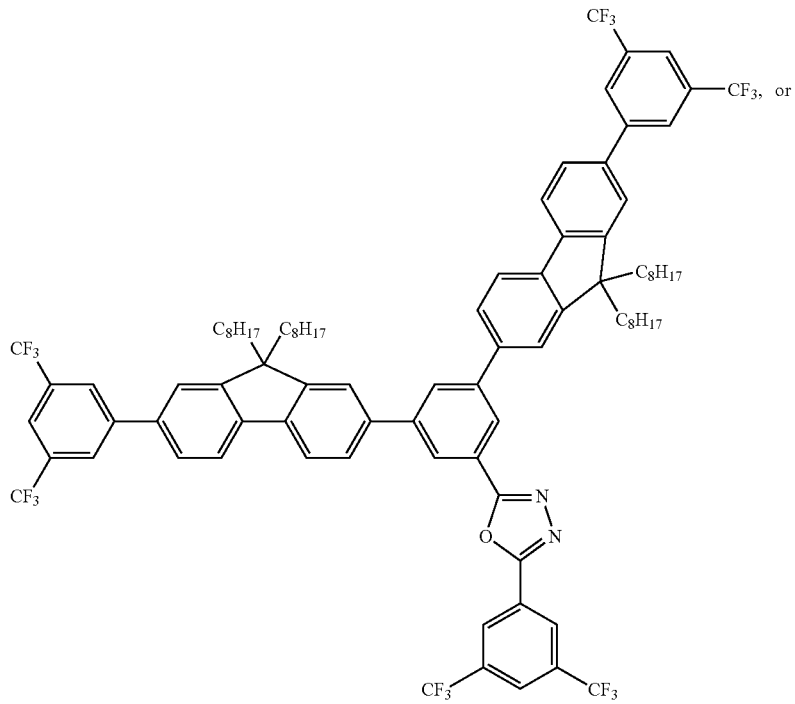
CCXVI
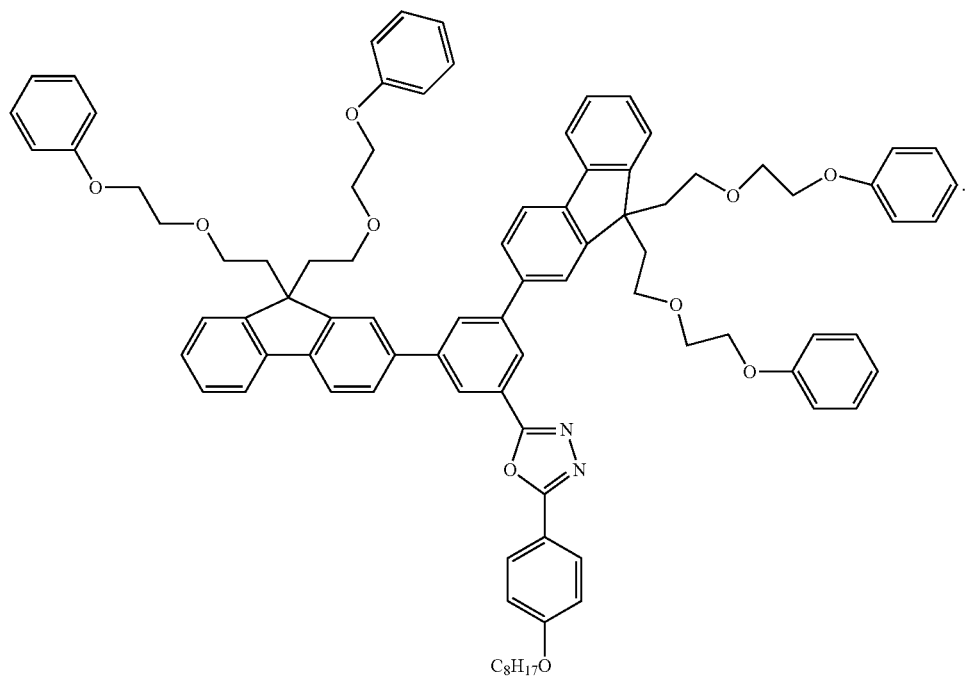
CCXVII

17. The compound or claim 1, wherein the compound is amorphous.

18. The compound of claim 1, wherein the compound is an electron transporting material.

19. The compound of claim 1, wherein the compound is both an electron and hole transporting material.

20. The compound of claim 1, wherein the compound is a light emitting material and an electron transporting material.

21. A composition comprising:
(a) a first compound comprising a first aromatic core and two first end capping groups conjugated to the first aromatic core, said compound having Formula IV:

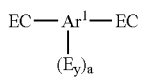
IV wherein
each $Ar^1$ is independently a radical of benzene, naphthalene, anthracene, phenanthrene, 9,10-dihydrophenanthrene, 4,5,9,10-tetrahydropyrene, fluorene, 9-silafluorene, 6,12-dihydroindeno[1,2-b]fluorene, 5,12-dihydro-6H-indeno[1,2-b]phenanthrene, 5,6,12,13-tetrahydrodibenzo[a,h]anthracene, 2-phenyl-9H-fluorene, or acenaphthene that is unsubstituted or substituted with one or more groups selected from alkyl, alkenyl, alkoxy, fluoro, fluoroalkyl, perfluoroalkyl, heteroalkyl, and combinations thereof,
wherein when $Ar^1$ is a radical of benzene, the group

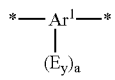

is selected from

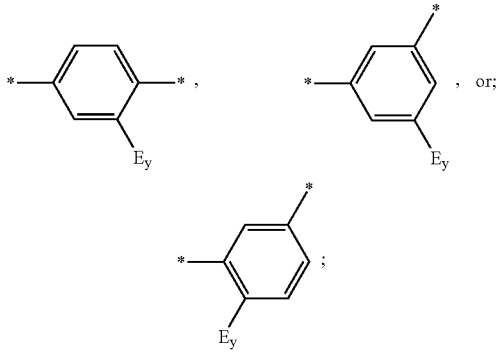

each a is independently 1 or 2;
each $E_y$ is independently a structure of Formula II or Formula III:

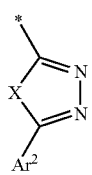
II

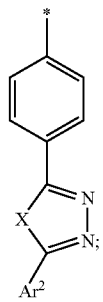
III each X is independently O, S, or $NR^1$, where $R^1$ is alkyl, aryl, heteroaryl, heteroalkyl, or combinations thereof
each $Ar^2$ is independently an aryl group that is unsubstituted or substituted with one or more groups selected from alkyl, alkenyl, alkoxy, aryl, aryloxy, fluoro, fluoroalkyl, perfluoroalkyl, heteroalkyl, alkyl oxadiazolyl, aryl oxadiazolyl, alkyl triazolyl, aryl triazolyl, diarylamino, aryldiarylamino, and combinations thereof;
each asterisk (-*) indicates the location of a bond to another group in the compound; and
each end capping group (EC) is independently a carbocyclic aryl, heteroaryl without a —C=N— unit, or tertiary amino aryl group that is unsubstituted or substituted with one or more groups selected from alkyl, alkenyl, alkoxy, aryl, aryloxy, fluoro, fluoroalkyl, perfluoroalkyl, heteroalkyl, heteroaryl without a —C=N— unit, and combinations thereof, wherein said end capping groups are conjugated to the aromatic core; and
(b) a second compound selected from a charge transporting material, a charge blocking material, a light emitting material, a color conversion material, a polymeric binder, or a combination thereof.

22. The composition of claim 21, wherein the composition comprises a hole transporting material and an electron transporting material.

23. The composition of claim 21, wherein the composition comprises a hole transporting material, an electron transporting material, and a light emitting material.

24. The composition of claim 21, wherein the second compound is selected from a charge transporting material, a charge blocking material, a light emitting material, a color conversion material, or a combination thereof, said second compound having
an aromatic radical that comprises the first aromatic core of the first compound, wherein the aromatic radical of the second compound can be unsubstituted, substituted with a substituent of a same type that is present on the first aromatic core of the first compound, or substituted with a substituent that is absent on the first aromatic core of the first compound; or
a second end capping group that comprises the first end capping group of the first compound, wherein the second end capping group can be unsubstituted, substituted with a substituent of a same type that is present on the first end capping group, or substituted with a substituent that is absent on the first end capping group; or
a divalent radical that comprises a divalent radical of the first end capping group of the first compound, wherein the divalent radical in the second compound can be unsubstituted, substituted with a substituent of a same type that is present on the first end capping group, or substituted with a substituent that is absent on the first end capping group; or a combination thereof.

25. The composition of claim 24, wherein the second compound is non-polymeric, said second compound comprising a second aromatic core and at least one second end capping group.

26. The composition of claim 25, wherein the second end capping group of the second compound comprises the first end capping group of the first compound.

27. The composition of claim 26, wherein the second aromatic core of the second compound is different than the first aromatic core of the first compound and the composition further comprises a monomer mixture comprising a first monomer comprising the first aromatic core and a second monomer comprising the second aromatic core.

28. The composition of claim 26, wherein the second aromatic core of the second compound is different than the first aromatic core of the first compound and the composition further comprises a polymer that is the reaction product of a monomer mixture comprising a first monomer comprising the first aromatic core and a second monomer comprising the second aromatic core.

29. The composition of claim 25, further comprising a light emitting polymer.

30. The composition of claim 25, further comprising an electroactive polymer.

31. The composition of claim 25, further comprising an inactive polymer.

32. The composition of claim 25, wherein the second aromatic core of the second compound comprises the first aromatic core of the first compound.

33. The composition of claim 32, further comprising a light emitting polymer.

34. The composition of claim 32, further comprising an electroactive polymer.

35. The composition of claim 32, further comprising an inactive polymer.

36. The composition of claim 32, wherein the second end capping group of the second compound is different than the first end capping group of the first compound and the composition further comprises a monomer mixture comprising a first monomer comprising the first end capping group or a divalent radical of the first end capping group and a second monomer comprising the second end capping group or a divalent radical of the second end capping group.

37. The composition of claim 32, wherein the second compound has a second end capping group that is different than the first end capping group of the first compound and the composition further comprises a polymer that is the reaction product of a monomer mixture comprising a first monomer comprising the first end capping group or a divalent radical of the first end capping group and a second monomer comprising the second end capping group or a divalent radical of the second end capping group.

38. The composition of claim 21, wherein the second compound is a polymer comprising the reaction product of a monomer mixture comprising a first monomer comprising the first aromatic core of the first compound.

39. The composition of claim 21, wherein the second compound is a polymer that is the reaction product of a monomer mixture comprising a first monomer comprising the first end capping group or a radical of the first end capping group.

40. The composition of claim 21, wherein composition is amorphous.

41. The composition of claim 21, wherein the composition is solution processable.

42. An organic electronic device comprising a compound having an aromatic core and two end capping groups conjugated to the aromatic core, said compound having Formula IV:

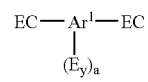

IV wherein each $Ar^1$ is independently a radical of benzene, naphthalene, anthracene, phenanthrene, 9,10-dihydrophenanthrene, 4,5,9,10-tetrahydropyrene, fluorene, 9-silafluorene, 6,12-dihydroindeno[1,2-b]fluorene, 5,12-dihydro-6H-indeno[1,2-b]phenanthrene, 5,6,12,13-tetrahydrodibenzo[a,h]anthracene, 2-phenyl-9H-fluorene, or acenaphthene that is unsubstituted or substituted with one or more groups selected from alkyl, alkenyl, alkoxy, fluoro, fluoroalkyl, perfluoroalkyl, heteroalkyl, and combinations thereof, wherein when $Ar^1$ is a radical of benzene, the group

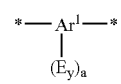

is selected from

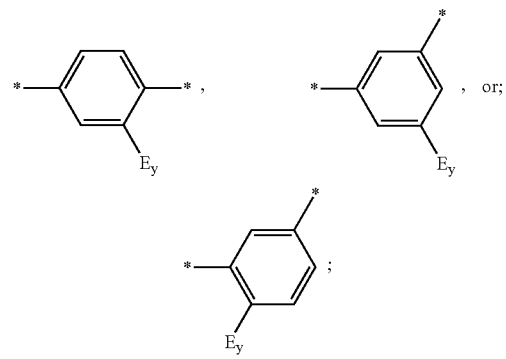

each a is independently 1 or 2;

each $E_y$ is independently a structure of Formula II or Formula III:

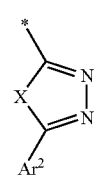

II

-continued

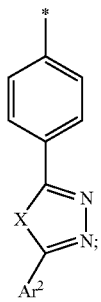

III each X is independently O, S, or NR$^1$, where R$^1$ is alkyl, aryl, heteroaryl, heteroalkyl, or combinations thereof;

each Ar$^2$ is independently an aryl group that is unsubstituted or substituted with one or more groups selected from alkyl, alkenyl, alkoxy, aryl, aryloxy, fluoro, fluoroalkyl, perfluoroalkyl, heteroalkyl, alkyl oxadiazolyl, aryl oxadiazolyl, alkyl triazolyl, aryl triazolyl, diarylamino, aryldiarylamino, and combinations thereof;

each asterisk (-*) indicates the location of a bond to another group in the compound; and each end capping group (EC) is independently a carbocyclic aryl, heteroaryl without a —C=N— unit, or tertiary amino aryl group that is unsubstituted or substituted with one or more groups selected from alkyl, alkenyl, alkoxy, aryl, aryloxy, fluoro, fluoroalkyl, perfluoroalkyl, heteroalkyl, heteroaryl without a —C=N— unit, and combinations thereof, wherein said end capping groups are conjugated to the aromatic core.

43. The organic electronic device of claim 42, wherein the device is an organic electroluminescent device.

44. The organic electronic device of claim 43, wherein the organic electroluminescent device comprises an organic emissive element comprising the compound of Formula IV.

45. The organic electronic device of claim 44, wherein the organic emissive element further comprises a charge transporting material, a charge blocking material, a polymeric material, a light emitting material, a color conversion layer, or a combination thereof.

46. The organic electronic device of claim 44, wherein the organic emissive element has multiple layers and the compound of Formula IV is in a light emitting layer.

47. The organic electronic device of claim 44, wherein the organic emissive element has multiple layers and the compound of Formula IV is in a charge transporting layer.

* * * * *

UNITED STATES PATENT AND TRADEMARK OFFICE
CERTIFICATE OF CORRECTION

PATENT NO. : 7,271,406 B2
APPLICATION NO. : 10/413653
DATED : September 18, 2007
INVENTOR(S) : James G. Bentsen It is certified that error appears in the above-identified patent and that said Letters Patent is hereby corrected as shown below:

On Page 2, in Column 1, under (Other Documents)
Line 28, delete "376303766" and insert -- 3763-3766 --, therefor.

On Page 2, in Column 2, under (Other Documents)
Line 66, delete "vinylcarbarzole)" and insert -- vinylcarbazole) --, therefor.
Line 66, delete "Anthracence" and insert -- Anthracene --, therefor.

On Page 3, in Column 1, under (Other Documents)
Line 2, delete "-arl/" and insert -- -aryl/ --, therefor.
Line 4, delete "1,4-divinylbenznes" and insert -- 1,4-divinylbenzenes --, therefor.

Column 2
Line 14, delete "perfluoroalky," and insert -- perfluoroalkyl, --, therefor.

Column 4
Line 40, after "P in" insert -- the ring --.
Line 52, delete "and" and insert -- aryl --, therefor.
Line 53, delete "biphenyl." and insert -- biphenyl, --, therefor.
Line 55, delete "tetrahydropyrenvi," and insert -- tetrahydropyrenyl, --, therefor.
Line 58, delete "tetrahydrodibeuzo" and insert -- tetrahydrodibenzo --, therefor.
Line 60, delete "benzo[gh,I]" and insert -- benzo[g,h,i] --, therefor.
Line 61, delete "pyrenyl." and insert -- perylenyl. --, therefor.

Column 5
Line 10, delete "dihyrophenanthrene" and insert -- dihyrophenanthrene, --, therefor.
Line 14, after "1,4-diyl" insert -- , --.
Line 18, after "3,9" insert -- - --.
Line 21, delete "benzo[gh,I]" and insert -- benzo[g,h,i] --, therefor.

Column 8
Line 16, delete "$C_{130}$" and insert -- $C_{1-30}$ --, therefor.
Line 37, delete ""tertiary aromatic amine"" and insert -- substituent --, therefor.
Line 42, delete "heteroalyl," and insert -- heteroalkyl, --, therefor.
Line 45, delete "herin," and insert -- herein, --, therefor.
Line 50, delete "tetraanryldiamines" and insert -- tetraaryldiamines --, therefor.

Column 9
Line 2, delete "benzencs" and insert -- benzenes --, therefor.
Line 6, before "Phys." insert -- Appl. --.

UNITED STATES PATENT AND TRADEMARK OFFICE
CERTIFICATE OF CORRECTION

PATENT NO. : 7,271,406 B2
APPLICATION NO. : 10/413653
DATED : September 18, 2007
INVENTOR(S) : James G. Bentsen It is certified that error appears in the above-identified patent and that said Letters Patent is hereby corrected as shown below:

Column 10
Line 46, delete "Ey" and insert -- $E_y$ --, therefor.

Column 11
Line 25, delete "emdodiments," and insert -- embodiments, --, therefor.

Column 16
Lines 38-39, delete "* ⟨⟨Ar]$_v$⟩—SS——R""" and insert -- *⟨Ar⟩$_v$—SS——R" --, therefor.

Column 18
Line 50, delete "Cl-$_{20}$" and insert -- $C_{1-20}$ --, therefor.

Column 21
Line 63, delete "Ar ." and insert -- $Ar^2$ --, therefor.

Column 22
Line 7, delete "benzo[gh,I]" and insert -- benzo[g,h,i] --, therefor.

Column 34
Line 39, before "butyl" delete "an" and insert -- a --, therefor.

Column 35
Line 15, delete "startburst" and insert -- starburst --, therefor.
Line 64, delete "band gap" and insert -- bandgap --, therefor.

Column 39
Line 29, delete "$C_{120}$" and insert -- $C_{1-20}$ --, therefor.

Column 41
Line 20, delete "CXLII" and insert -- CXLIII --, therefor.

UNITED STATES PATENT AND TRADEMARK OFFICE
CERTIFICATE OF CORRECTION

PATENT NO. : 7,271,406 B2
APPLICATION NO. : 10/413653
DATED : September 18, 2007
INVENTOR(S) : James G. Bentsen Page 3 of 7

It is certified that error appears in the above-identified patent and that said Letters Patent is hereby corrected as shown below:

Column 54, in (Structure No. CCXIII)
Line 1 delete "  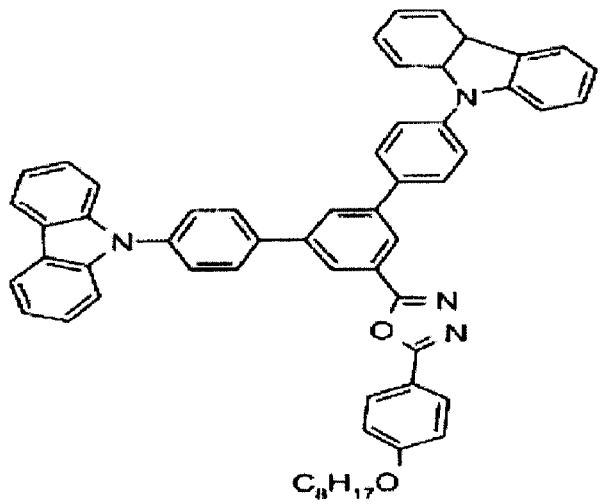  " and insert

--  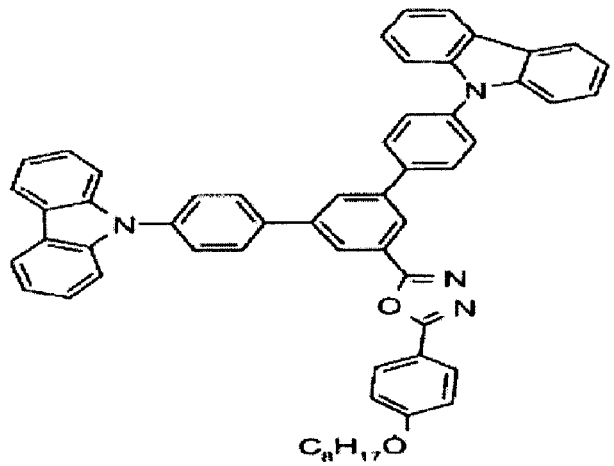  --, therefor.

UNITED STATES PATENT AND TRADEMARK OFFICE
CERTIFICATE OF CORRECTION

PATENT NO. : 7,271,406 B2
APPLICATION NO. : 10/413653
DATED : September 18, 2007
INVENTOR(S) : James G. Bentsen It is certified that error appears in the above-identified patent and that said Letters Patent is hereby corrected as shown below:

Column 57
Line 61, delete "Diahalogenated" and insert -- Dihalogenated --, therefor.

Column 58
Line 49, delete "$Ar_1$" and insert -- $\mathbf{Ar^1}$ --, therefor.

Column 61
Line 58, delete "(5" and insert -- (5) --, therefor.

Column 62
Line 48, delete "D' and RZ" and insert -- $\mathbf{D^1}$ and $\mathbf{R^z}$ --, therefor.

Column 67
Line 4, delete "RZ" and insert -- $\mathbf{R^z}$ --, therefor.

Column 68
Line 22, delete "Soc." and insert -- Soc., --, therefor.

Column 71
Line 7, delete "(Ey)a" and insert -- $(E_y)_a$ --, therefor.
Line 14, delete "9, 10" and insert -- 9,10 --, therefor.
Line 21, delete "$NH_4CI$" and insert -- $NH_4Cl$ --, therefor.

Column 72
Line 61, delete "benzhydrazide" and insert -- benzohydrazide --, therefor.

Column 79
Line 9, delete "monohalogented" and insert -- monohalogenated --, therefor.

Column 80
Line 56, delete "cylcometalated" and insert -- cyclometallated --, therefor.

Column 81
Line 25, delete "pixilated" and insert -- pixelated --, therefor.

Column 83
Line 52, delete "$Z_2$" and insert -- $\mathbf{Z_1}$ --, therefor.

Column 84
Line 17, delete "$Z_2$includes" and insert -- $\mathbf{Z_2}$ includes --, therefor.

UNITED STATES PATENT AND TRADEMARK OFFICE
CERTIFICATE OF CORRECTION

PATENT NO.       : 7,271,406 B2
APPLICATION NO.  : 10/413653
DATED            : September 18, 2007
INVENTOR(S)      : James G. Bentsen It is certified that error appears in the above-identified patent and that said Letters Patent is hereby corrected as shown below:

Column 85
Line 48, delete ".but" and insert -- but --, therefor.

Column 86
Line 47, delete "A1)." and insert -- $A_1$). --, therefor.

Column 87
Line 7, delete "in:" and insert -- in --, therefor.

Column 89
Line 58, delete "be;" and insert -- be --, therefor.

Column 90
Line 41, after "the" delete ".".

Column 91
Line 67, delete "pixilated" and insert -- pixelated --, therefor.

Column 93
Line 19, delete "(I-naphthyl" and insert -- (1-naphthyl --, therefor.
Line 39, delete "(Alq3)." and insert -- (Alq$_3$). --, therefor.

Column 101
Line 27, delete "dichlor-" and insert -- dichloro- --, therefor.

Column 106
Line 32, delete "(oxtyloxy)" and insert -- (octyloxy) --, therefor.

Column 109
Line 63, delete "Aliqua$^{TM}$" and insert -- Aliquat$^{TM}$ --, therefor.

Column 112
Line 25, delete "Aliqua$^{TM}$" and insert -- Aliquat$^{TM}$ --, therefor.

Column 116
Line 20, delete "δ0.53-0.69" and insert -- δ 0.53-0.69 --, therefor.
Line 27, delete "δ0.51-0.65" and insert -- δ 0.51-0.65 --, therefor.

Column 119
Line 58, delete "aqeous" and insert -- aqueous --, therefor.

UNITED STATES PATENT AND TRADEMARK OFFICE
CERTIFICATE OF CORRECTION

PATENT NO. : 7,271,406 B2
APPLICATION NO. : 10/413653
DATED : September 18, 2007
INVENTOR(S) : James G. Bentsen It is certified that error appears in the above-identified patent and that said Letters Patent is hereby corrected as shown below:

Column 121
Line 65, delete "mthanol," and insert -- methanol, --, therefor.

Column 122
Line 51, after "Yasui" insert -- Seiki --.

Column 130
Line 19, in Claim 3, delete "xv" and insert -- w --, therefor.
Line 33, in Claim 5, delete "benzo[g,h,l]" and insert -- benzo[g,h,i] --, therefor.
Line 34, in Claim 5, delete "$C_{1-20}$" and insert -- $C_{2-20}$ --, therefor.

Column 141
Line 25-26, in Claim 7, delete "spirobistfluorenyl," and insert -- spirobisfluorenyl, --, therefor.
Line 50, in Claim 9, delete "arylcarbazole" and insert -- arylcarbazole, --, therefor.
Line 53, in Claim 9, delete "aroups" and insert -- groups --, therefor.
Line 58, in Claim 10, delete "a.t" and insert -- at --, therefor.

Column 150
Lines 61-62, in Claim 14, delete "$\{Si(C_wH_{2w+1})_2O\}_y^*,$"

and insert -- $*\text{---}[Si(C_wH_{2w+1})_2O]_y\text{---}*$ --, therefor.

UNITED STATES PATENT AND TRADEMARK OFFICE
CERTIFICATE OF CORRECTION

PATENT NO. : 7,271,406 B2
APPLICATION NO. : 10/413653
DATED : September 18, 2007
INVENTOR(S) : James G. Bentsen It is certified that error appears in the above-identified patent and that said Letters Patent is hereby corrected as shown below:

Column 157
Line 1, in Claim 17, delete "or" and insert -- of --, therefor.

Column 158
Line 18, in Claim 21, delete "thereof" and insert -- thereof; --, therefor.

Signed and Sealed this

Tenth Day of June, 2008

JON W. DUDAS
*Director of the United States Patent and Trademark Office*